(12) United States Patent
Lee et al.

(10) Patent No.: US 11,219,530 B2
(45) Date of Patent: Jan. 11, 2022

(54) IMPLANTS AND METHODS OF USE AND ASSEMBLY

(71) Applicant: Paragon 28, Inc., Englewood, CO (US)

(72) Inventors: Daniel Lee, Denver, CO (US); Albert Dacosta, Lone Tree, CO (US); Frank Barmes, Parker, CO (US); Joseph Dogué, Aurora, CO (US); Richard Obert, Poway, CA (US); Robert David Paxson, Lakeland, TN (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 16/949,310

(22) Filed: Oct. 24, 2020

(65) Prior Publication Data
US 2021/0038402 A1    Feb. 11, 2021

Related U.S. Application Data

(63) Continuation-in-part of application No. PCT/US2019/029009, filed on Apr. 24, 2019.
(Continued)

(51) Int. Cl.
*A61F 2/42* (2006.01)
*A61F 2/30* (2006.01)

(52) U.S. Cl.
CPC ...... *A61F 2/4202* (2013.01); *A61F 2002/305* (2013.01); *A61F 2002/30112* (2013.01); *A61F 2002/30164* (2013.01); *A61F 2002/30199* (2013.01); *A61F 2002/30317* (2013.01); *A61F 2002/30387* (2013.01);
(Continued)

(58) Field of Classification Search
CPC .. A61F 2/42; A61F 2/4202; A61F 2002/4205; A61F 2002/4207
See application file for complete search history.

(56) References Cited

U.S. PATENT DOCUMENTS

| 3,975,778 A | 8/1976 | Newton, III |
| 4,021,864 A | 5/1977 | Waugh |

(Continued)

FOREIGN PATENT DOCUMENTS

| EP | 1097680 | 9/2005 |
| EP | 1489999 | 9/2005 |

(Continued)

OTHER PUBLICATIONS

Schweitzer et al., Total Ankle Arthroplasty with a Modern Fixed-Bearing System: The Salto Talaris Prosthesis, JBJS Essential Surgical Techniques, retrieved from the internet at https://www.ncbi.nlm.nih.gov/pmc/articles/PMC6407948/pdf/jbjsest-3-e18.pdf, 9 pages, 2013.

(Continued)

*Primary Examiner* — Marcia L Watkins
(74) *Attorney, Agent, or Firm* — Heslin Rothenberg Farley & Mesiti P.C.; Jacquelyn A. Graff, Esq.

(57) ABSTRACT

Implants, devices, and methods for maintaining, correcting and/or fusing joint deformities are disclosed. The implant a first member, a second member, and an insert with a top surface and a bottom surface. The top surface couples to the first member and the bottom surface engages the second member. Kits and methods of using the implants for maintaining, correcting and/or fusing joint deformities are also disclosed.

34 Claims, 68 Drawing Sheets

Related U.S. Application Data

(60) Provisional application No. 62/661,945, filed on Apr. 24, 2018.

(52) U.S. Cl.
CPC ............ *A61F 2002/30401* (2013.01); *A61F 2002/30616* (2013.01); *A61F 2002/30688* (2013.01); *A61F 2002/30878* (2013.01); *A61F 2002/4205* (2013.01); *A61F 2002/4207* (2013.01)

(56) References Cited

U.S. PATENT DOCUMENTS

| | | | |
|---|---|---|---|
| 4,069,518 A | 1/1978 | Groth et al. | |
| 5,326,365 A | 7/1994 | Alvine | |
| 5,702,464 A | 12/1997 | Lackey | |
| 6,409,767 B1 | 6/2002 | Perice et al. | |
| 6,863,691 B2 | 3/2005 | Short et al. | |
| 6,926,739 B1 | 8/2005 | O'Connor et al. | |
| 7,025,790 B2 | 4/2006 | Parks et al. | |
| 7,323,012 B1 | 1/2008 | Stone et al. | |
| 7,534,270 B2 | 5/2009 | Ball | |
| 7,615,082 B2 | 11/2009 | Naegerl et al. | |
| 7,625,409 B2 | 12/2009 | Saltzman et al. | |
| 8,114,091 B2 | 2/2012 | Ratron | |
| 8,147,557 B2 | 4/2012 | Lee | |
| 8,530,057 B2 | 9/2013 | Muratoglu et al. | |
| 8,546,460 B2 | 10/2013 | Brunner et al. | |
| 8,591,595 B2 | 11/2013 | Kofoed et al. | |
| 8,591,596 B2 | 11/2013 | Long | |
| 8,888,859 B2 | 11/2014 | Muratoglu et al. | |
| 9,320,609 B2 | 4/2016 | Schon et al. | |
| 9,421,104 B2 | 8/2016 | Schroeder et al. | |
| 9,579,210 B2 | 2/2017 | Wong | |
| 9,610,168 B2 | 4/2017 | Terrill et al. | |
| 9,681,958 B2 | 6/2017 | Kofoed et al. | |
| 9,700,651 B2 | 7/2017 | Kyomoto et al. | |
| 9,750,613 B2 | 9/2017 | Petteys | |
| 9,757,244 B2 | 9/2017 | Sander | |
| 9,877,839 B2 | 1/2018 | Dhillon et al. | |
| 9,918,724 B2 | 3/2018 | Luna et al. | |
| 9,925,054 B2 | 3/2018 | Siegler et al. | |
| 9,951,190 B2 | 4/2018 | He et al. | |
| 10,123,878 B2 | 11/2018 | Impero et al. | |
| 10,136,998 B2 | 11/2018 | Dhillon et al. | |
| 10,166,110 B2 | 1/2019 | Terrill et al. | |
| 10,182,832 B1 * | 1/2019 | Saltzman | A61B 17/1682 |
| 10,314,713 B2 | 6/2019 | Hintermann | |
| 10,327,905 B2 | 6/2019 | Rouyer et al. | |
| 10,327,906 B2 | 6/2019 | Dhillon et al. | |
| 10,350,079 B2 | 7/2019 | Michel et al. | |
| 10,398,561 B2 | 9/2019 | Long | |
| 10,398,562 B2 | 9/2019 | Valderrabano et al. | |
| 10,413,417 B2 | 9/2019 | Petteys | |
| 10,433,970 B2 | 10/2019 | Siegler et al. | |
| 10,456,265 B2 | 10/2019 | Harris, Jr. | |
| 10,485,561 B2 | 11/2019 | Saltzman et al. | |
| 10,653,528 B2 | 5/2020 | Terrill et al. | |
| 10,799,364 B2 | 10/2020 | Sander | |
| 2003/0100953 A1 | 5/2003 | Rosa | |
| 2004/0167631 A1 | 8/2004 | Luchesi et al. | |
| 2004/0186585 A1 | 9/2004 | Feiwell | |
| 2005/0194723 A1 | 9/2005 | Muratoglu et al. | |
| 2005/0288792 A1 | 12/2005 | Landes | |
| 2006/0020345 A1 | 1/2006 | O'Connor et al. | |
| 2006/0142870 A1 | 6/2006 | Robinson et al. | |
| 2006/0149372 A1 * | 7/2006 | Paxson | A61F 2/4425 623/17.11 |
| 2006/0229730 A1 | 10/2006 | Railey | |
| 2006/0247788 A1 | 11/2006 | Ross | |
| 2007/0112431 A1 | 5/2007 | Kofoed | |
| 2008/0287976 A1 | 11/2008 | Weaner | |
| 2010/0057216 A1 * | 3/2010 | Gannoe | A61F 2/4684 623/21.18 |
| 2011/0029093 A1 * | 2/2011 | Bojarski | A61F 2/3859 623/20.35 |
| 2011/0035019 A1 | 2/2011 | Goswami et al. | |
| 2011/0040387 A1 | 2/2011 | Ries | |
| 2012/0267819 A1 | 10/2012 | Freedman | |
| 2013/0085499 A1 | 4/2013 | Lian | |
| 2013/0116797 A1 | 5/2013 | Coulange et al. | |
| 2014/0257506 A1 * | 9/2014 | Sanford | A61F 2/389 623/20.33 |
| 2015/0157339 A1 | 6/2015 | McGinley et al. | |
| 2015/0305753 A1 | 10/2015 | McGinley et al. | |
| 2015/0313727 A1 | 11/2015 | Waite, II | |
| 2015/0320567 A1 * | 11/2015 | Terrill | A61F 2/4202 623/21.18 |
| 2016/0008139 A1 * | 1/2016 | Siegler | A61F 2/4202 623/21.18 |
| 2016/0235543 A1 | 8/2016 | Hwa | |
| 2016/0262903 A1 | 9/2016 | West | |
| 2016/0367269 A9 | 12/2016 | McGinley et al. | |
| 2017/0056188 A1 | 3/2017 | Dhillon | |
| 2017/0125221 A1 | 5/2017 | Wong | |
| 2017/0367837 A1 | 12/2017 | Harris, Jr. | |
| 2018/0008425 A1 | 1/2018 | Petteys | |
| 2018/0042730 A1 | 2/2018 | Nachtrab | |
| 2018/0098858 A1 | 4/2018 | Valderrabano et al. | |
| 2018/0110625 A1 | 4/2018 | Dhillon et al. | |
| 2018/0125663 A1 | 5/2018 | Huxel et al. | |
| 2018/0243023 A1 | 8/2018 | Stemniski et al. | |
| 2018/0256349 A1 | 9/2018 | Siegler et al. | |
| 2019/0029838 A1 | 1/2019 | Terrill et al. | |
| 2019/0059917 A1 | 2/2019 | Saltzman et al. | |
| 2019/0070012 A1 | 3/2019 | Thibaut et al. | |
| 2019/0083268 A1 | 3/2019 | Sander | |
| 2019/0083273 A1 | 3/2019 | Luna | |
| 2019/0091032 A1 | 3/2019 | Pak et al. | |
| 2019/0262138 A1 | 8/2019 | Dhillon et al. | |
| 2019/0350717 A1 | 11/2019 | Tuttle | |
| 2019/0358047 A1 | 11/2019 | Petteys | |
| 2019/0388230 A1 | 12/2019 | Tsai et al. | |
| 2020/0060835 A1 | 2/2020 | Valderrabano et al. | |
| 2020/0085584 A1 | 3/2020 | Rouyer et al. | |
| 2020/0085585 A1 | 3/2020 | Siegler | |
| 2020/0093605 A1 | 3/2020 | Sander et al. | |
| 2020/0093606 A1 | 3/2020 | Hintermann | |
| 2020/0188126 A1 | 6/2020 | Lee et al. | |
| 2020/0197187 A1 | 6/2020 | Lee et al. | |
| 2020/0246154 A1 | 8/2020 | Nachtrab | |
| 2020/0268520 A1 | 8/2020 | Pak et al. | |
| 2020/0276025 A1 | 9/2020 | Terrill et al. | |
| 2020/0289283 A1 | 9/2020 | Sander et al. | |

FOREIGN PATENT DOCUMENTS

| | | |
|---|---|---|
| EP | 1180989 | 4/2006 |
| EP | 1658023 | 3/2007 |
| EP | 1675531 | 12/2008 |
| EP | 1677709 | 2/2012 |
| EP | 2124832 | 8/2012 |
| EP | 2664299 | 11/2013 |
| EP | 2671538 | 12/2013 |
| EP | 2575690 | 1/2014 |
| EP | 2334263 | 1/2015 |
| EP | 2832321 | 2/2015 |
| EP | 3135252 | 3/2017 |
| EP | 2856978 | 11/2017 |
| EP | 2913030 | 3/2018 |
| EP | 3142609 | 3/2018 |
| EP | 3354233 | 8/2018 |
| EP | 3135251 | 11/2018 |
| EP | 3049028 | 12/2018 |
| EP | 3290005 | 1/2019 |
| EP | 3449876 | 3/2019 |
| EP | 3449877 | 3/2019 |
| EP | 3459501 | 3/2019 |
| EP | 3512468 | 7/2019 |
| EP | 3354233 | 10/2019 |
| EP | 3375412 | 10/2019 |
| EP | 3449877 | 10/2019 |

(56) References Cited

FOREIGN PATENT DOCUMENTS

| | | |
|---|---|---|
| EP | 3551138 | 10/2019 |
| EP | 3242636 | 11/2019 |
| EP | 3193757 | 12/2019 |
| EP | 3283017 | 1/2020 |
| EP | 3586800 | 1/2020 |
| EP | 3215066 | 2/2020 |
| EP | 3603579 | 2/2020 |
| EP | 3488823 | 4/2020 |
| EP | 3636187 | 4/2020 |
| EP | 3649990 | 5/2020 |
| EP | 3659555 | 6/2020 |
| EP | 3672535 | 7/2020 |
| EP | 3679901 | 7/2020 |
| EP | 3687455 | 8/2020 |
| EP | 3698761 | 8/2020 |
| EP | 3459501 | 9/2020 |
| FR | 2700462 | 7/1994 |
| WO | 2000069373 | 11/2000 |
| WO | 2003079938 | 10/2003 |
| WO | 2004084773 | 10/2004 |
| WO | 2005030098 | 4/2005 |
| WO | 2005037135 | 4/2005 |
| WO | 2005041823 | 5/2005 |
| WO | 2006023824 | 3/2006 |
| WO | 2006136940 | 12/2006 |
| WO | 2008078082 | 7/2008 |
| WO | 2009032909 | 3/2009 |
| WO | 2010039026 | 4/2010 |
| WO | 2011150148 | 12/2011 |
| WO | 2013180228 | 12/2013 |
| WO | 2014149952 | 9/2014 |
| WO | 2015014695 | 2/2015 |
| WO | 2015044373 | 4/2015 |
| WO | 2015175560 | 11/2015 |
| WO | 2016039762 | 3/2016 |
| WO | 2016073001 | 5/2016 |
| WO | 2016112092 | 7/2016 |
| WO | 2016114751 | 7/2016 |
| WO | 2016167792 | 10/2016 |
| WO | 2017127067 | 7/2017 |
| WO | 2018203991 | 11/2018 |
| WO | 2019040865 | 2/2019 |
| WO | 2019045411 | 3/2019 |
| WO | 2019063807 | 4/2019 |
| WO | 2019090022 | 5/2019 |
| WO | 2019220048 | 11/2019 |
| WO | 2020013901 | 1/2020 |
| WO | 2020060602 | 3/2020 |
| WO | 2020130986 | 6/2020 |
| WO | 2020185299 | 9/2020 |

OTHER PUBLICATIONS

Wright Medical Iechnology, Inc., Prophecy Infinity Preoperative Navigation Guides, Surgical Technique, https://www.wightemedia.com/ProductFiles/Files/PDFs/011940_EN_LR_LE.pdf, 39 pages, Feb. 8, 2018 (retrieved from the internet on Mar. 16, 2020).

International Search Report and Written Opinion of the International Searching Authority for PCT/US2019/029009, dated Feb. 18, 2020, 14 pages.

* cited by examiner

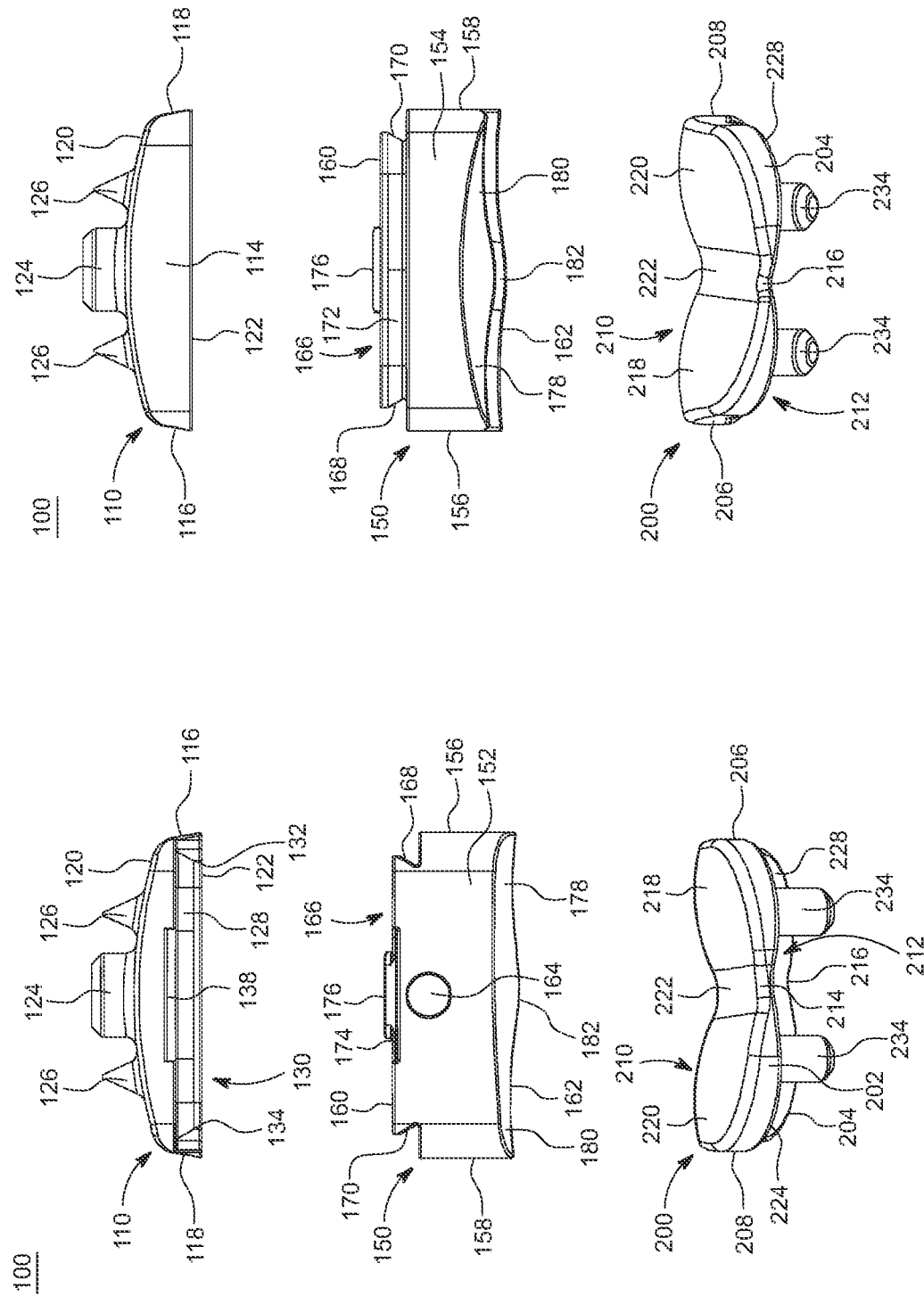

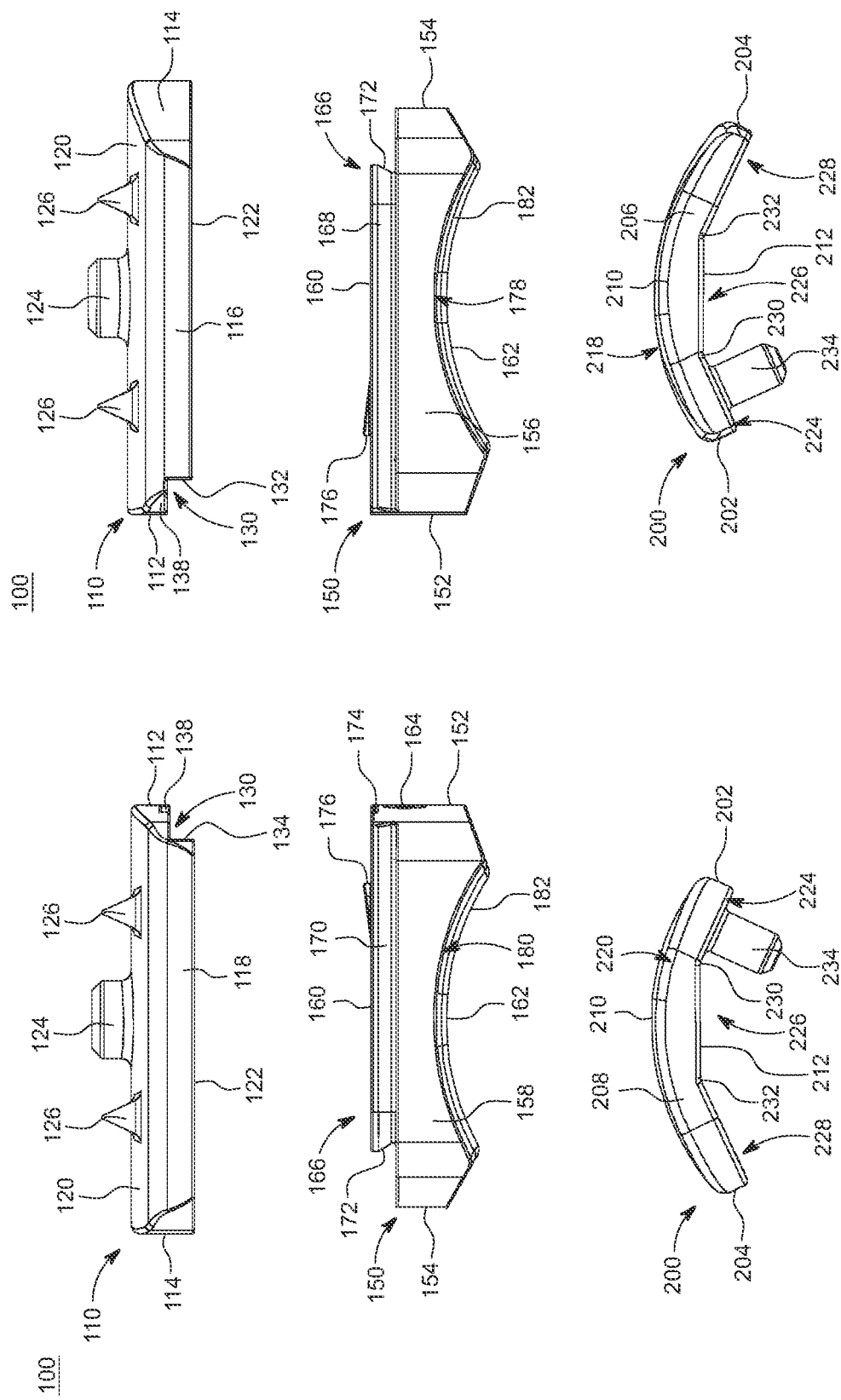

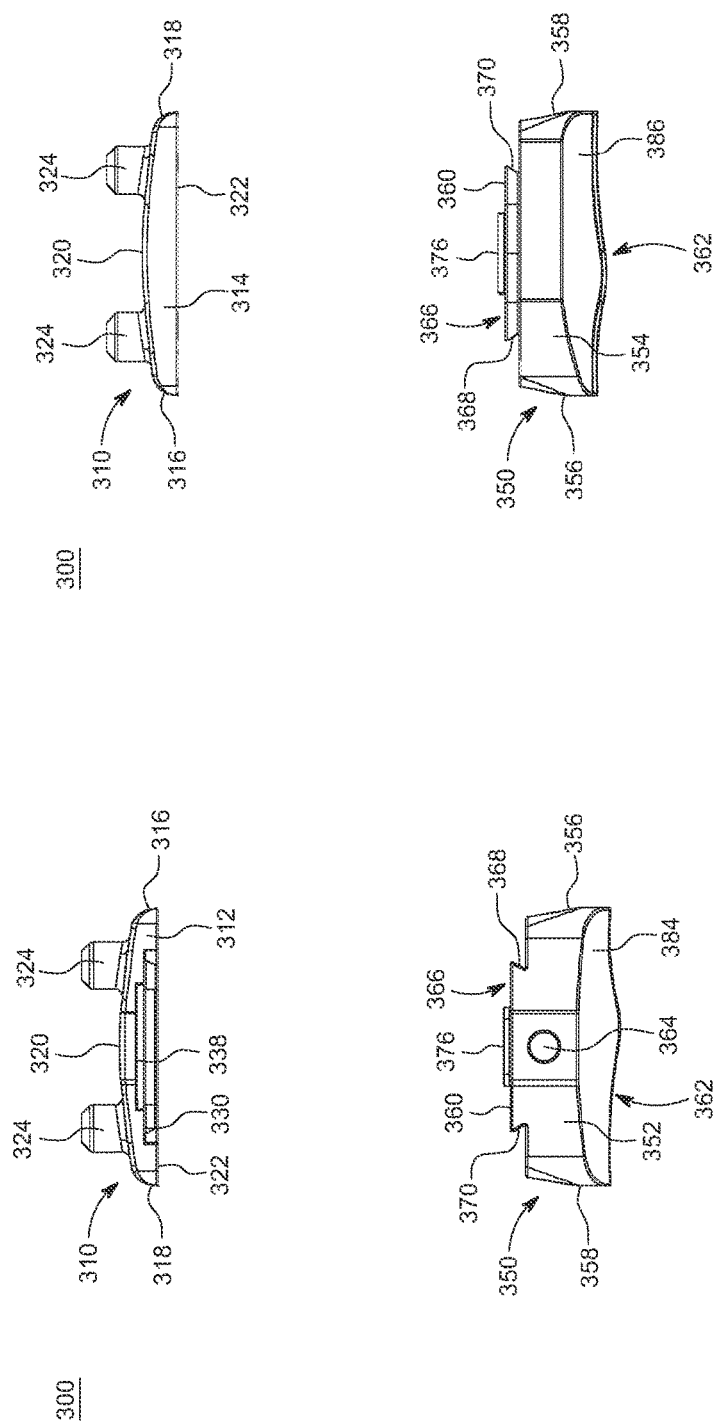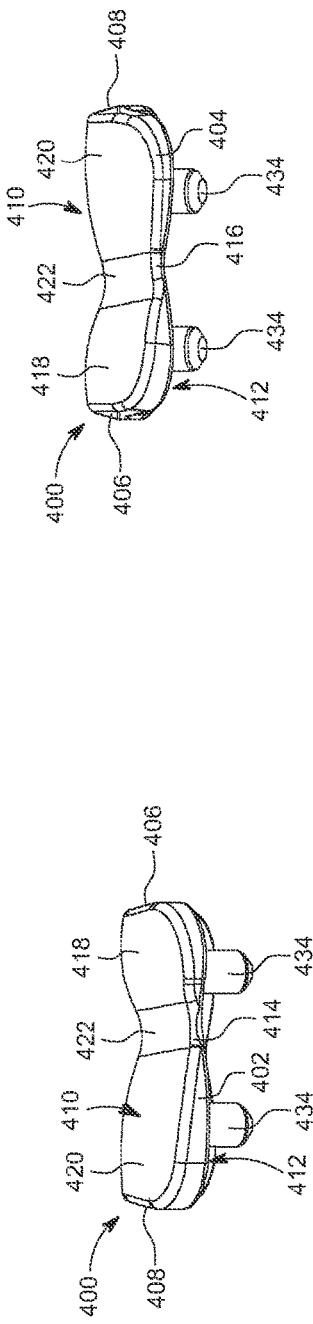
FIG. 28
FIG. 29

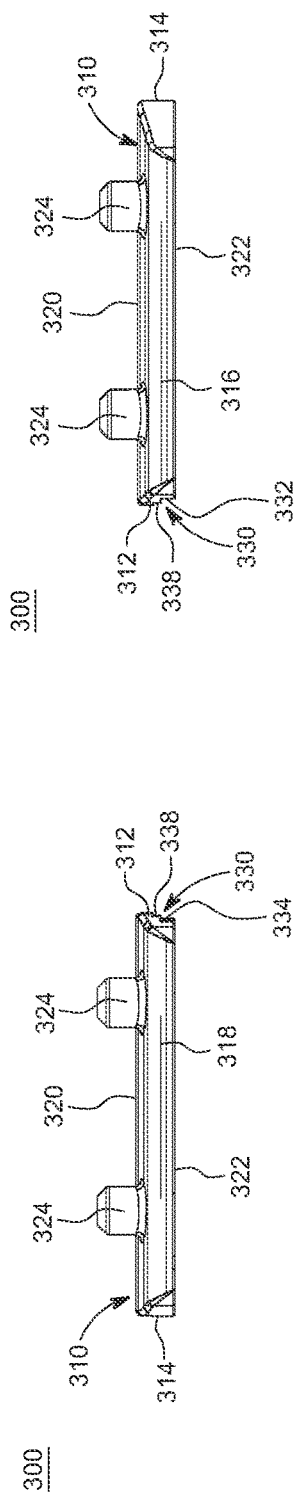

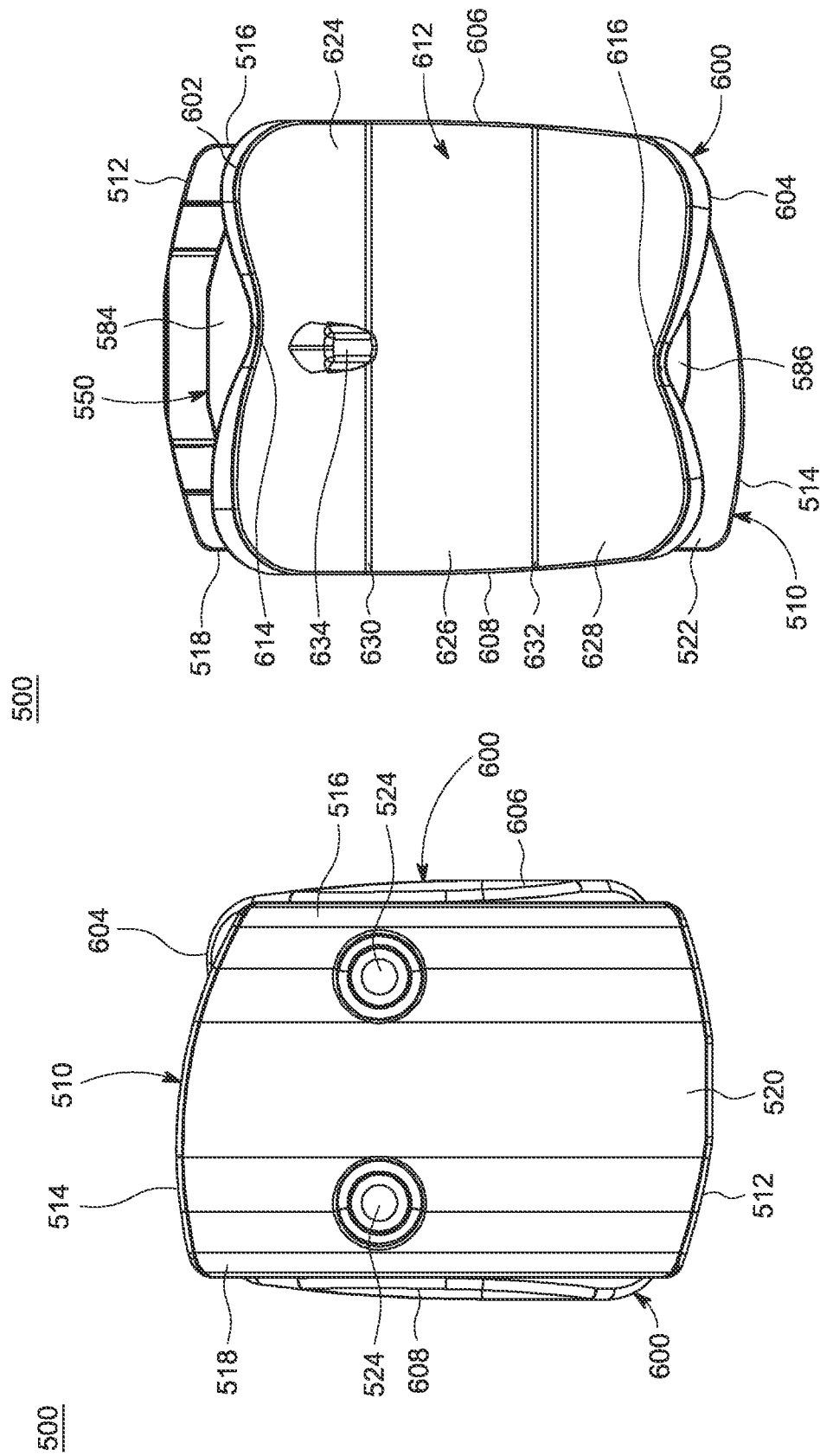

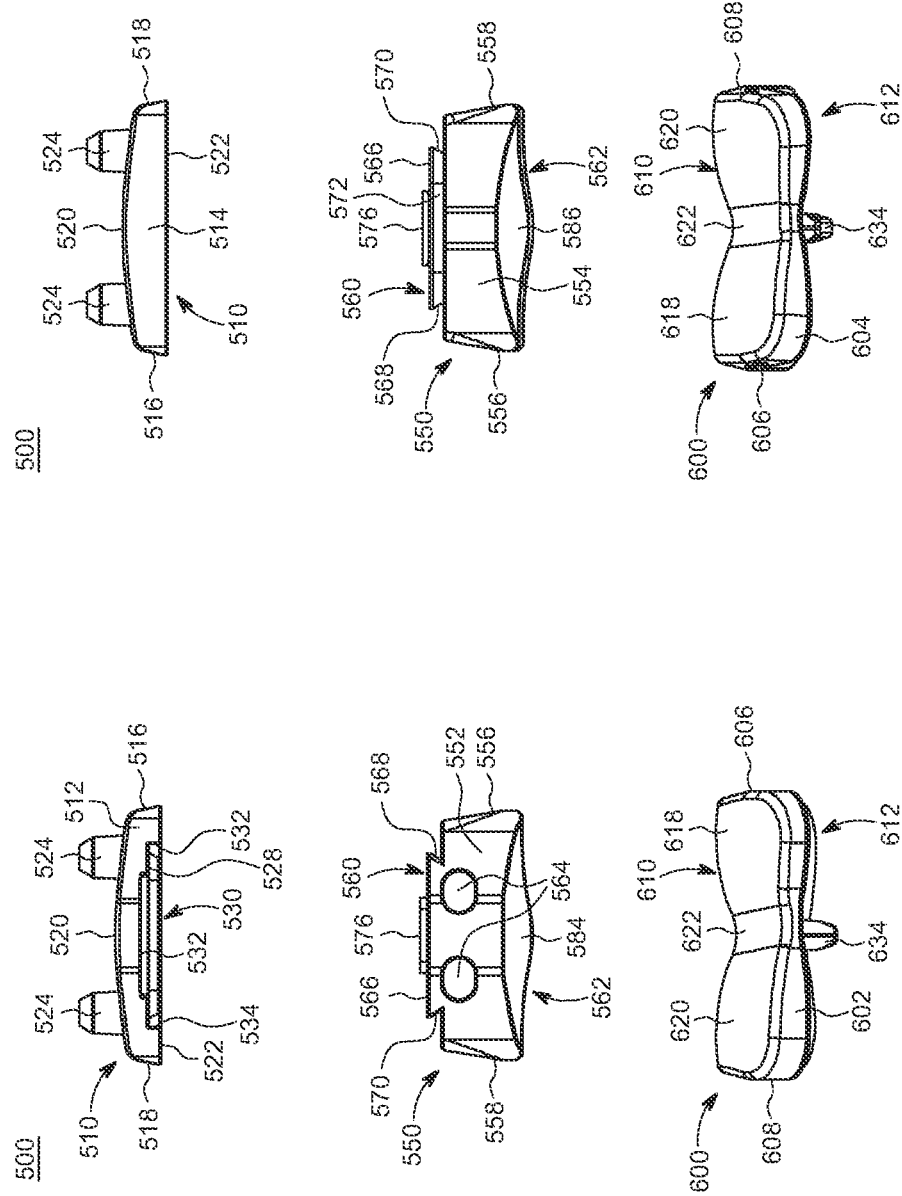

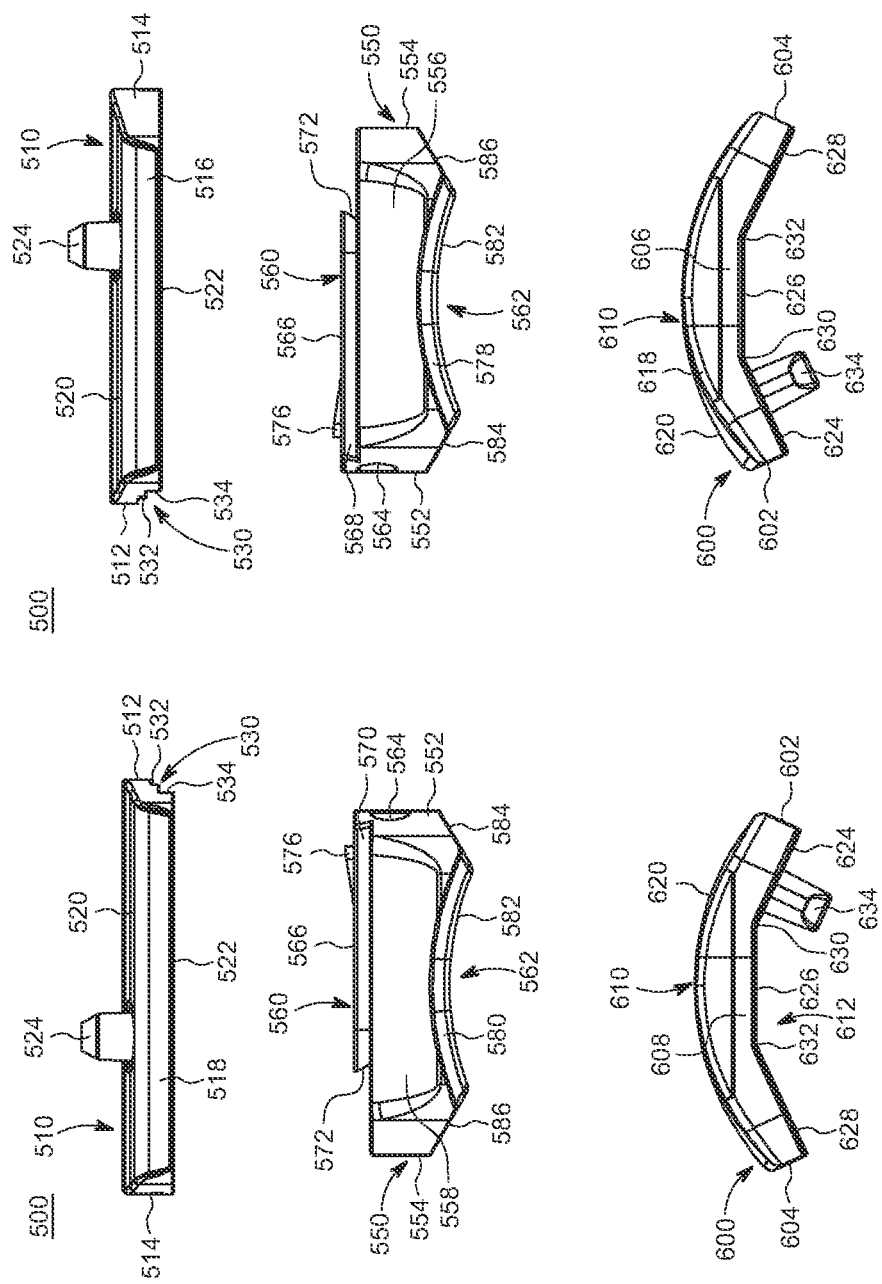

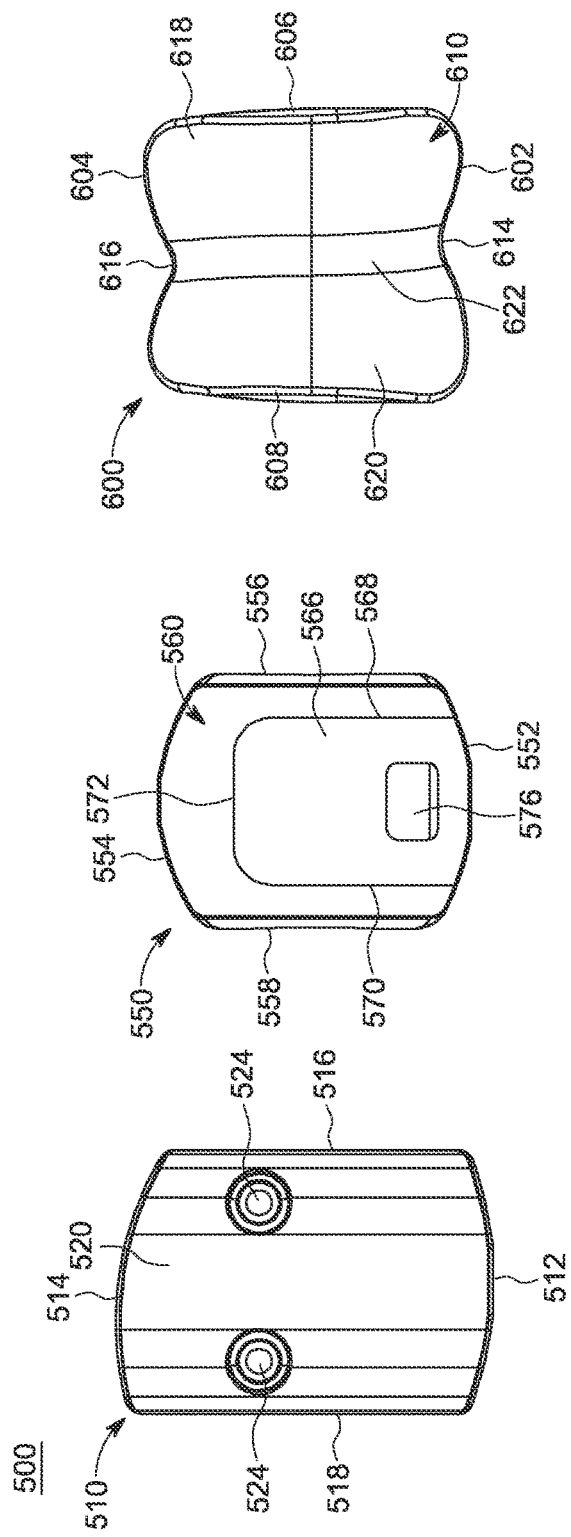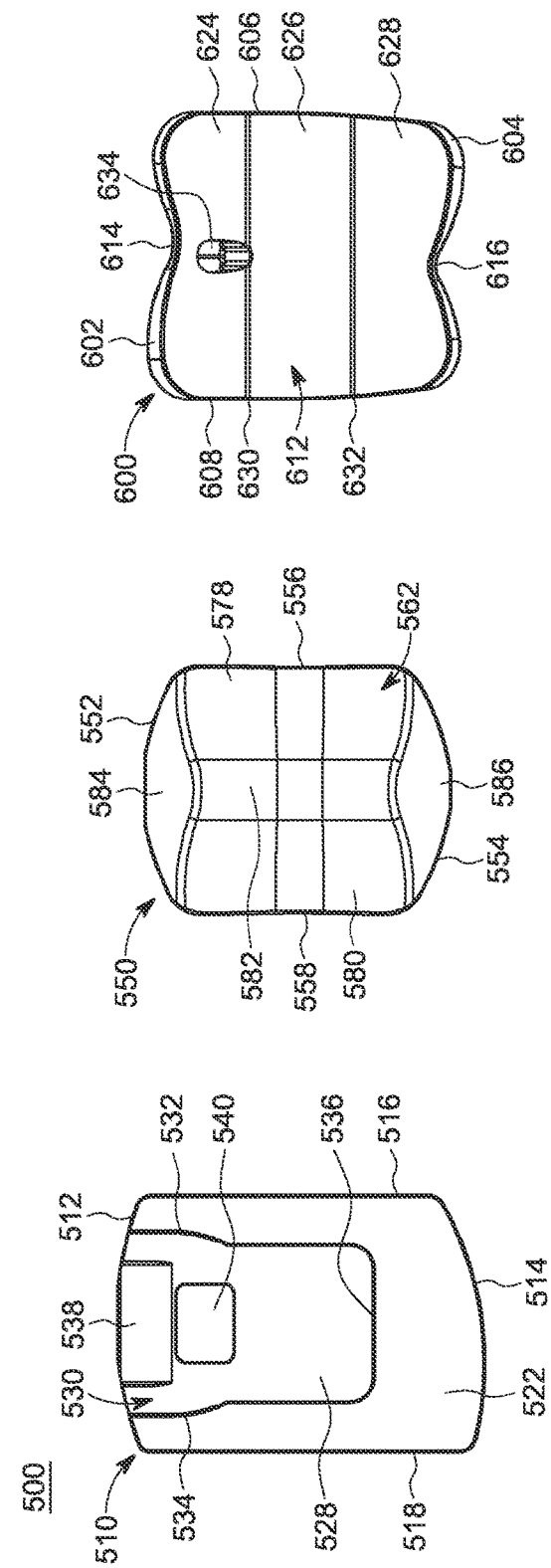

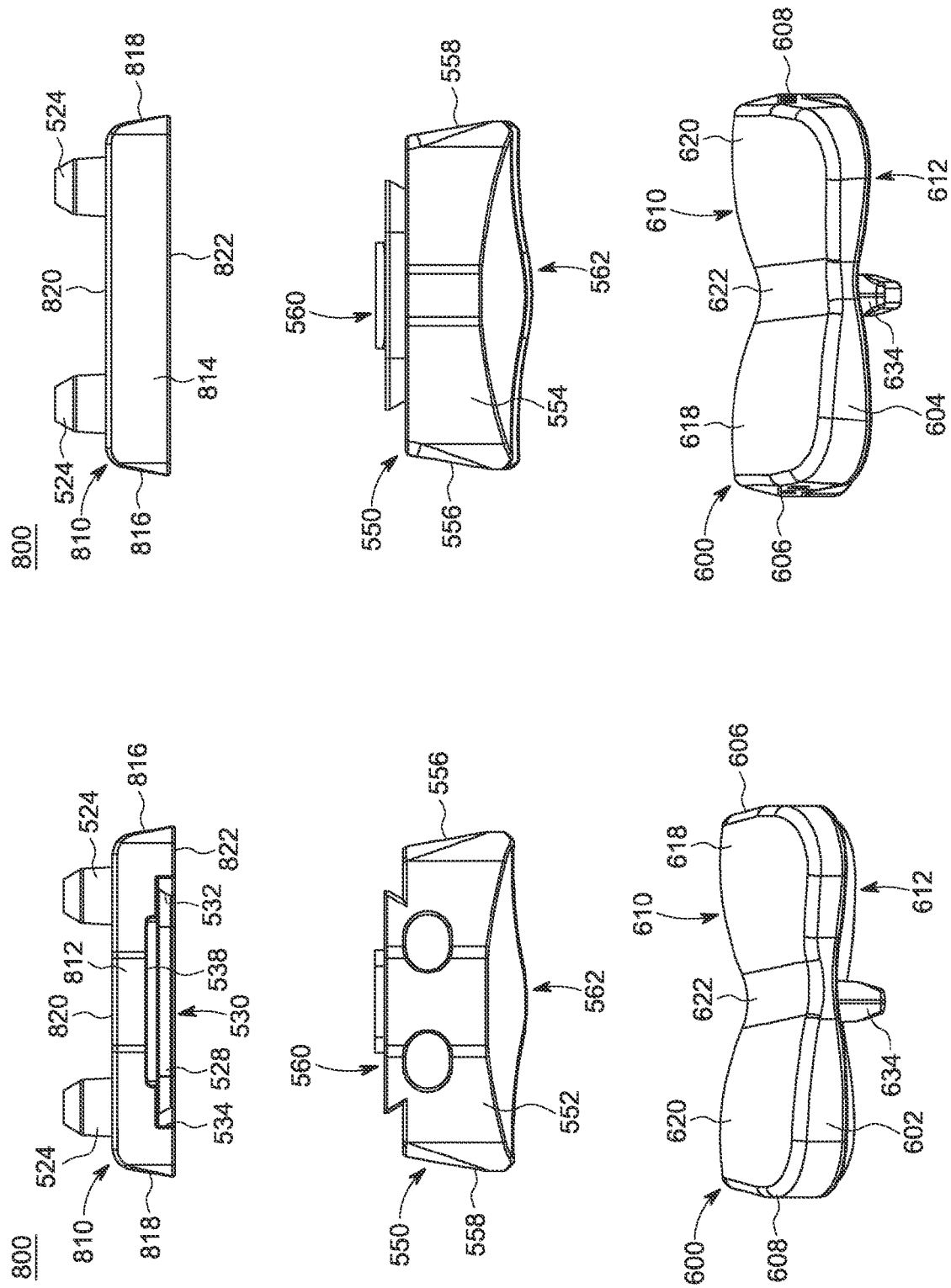

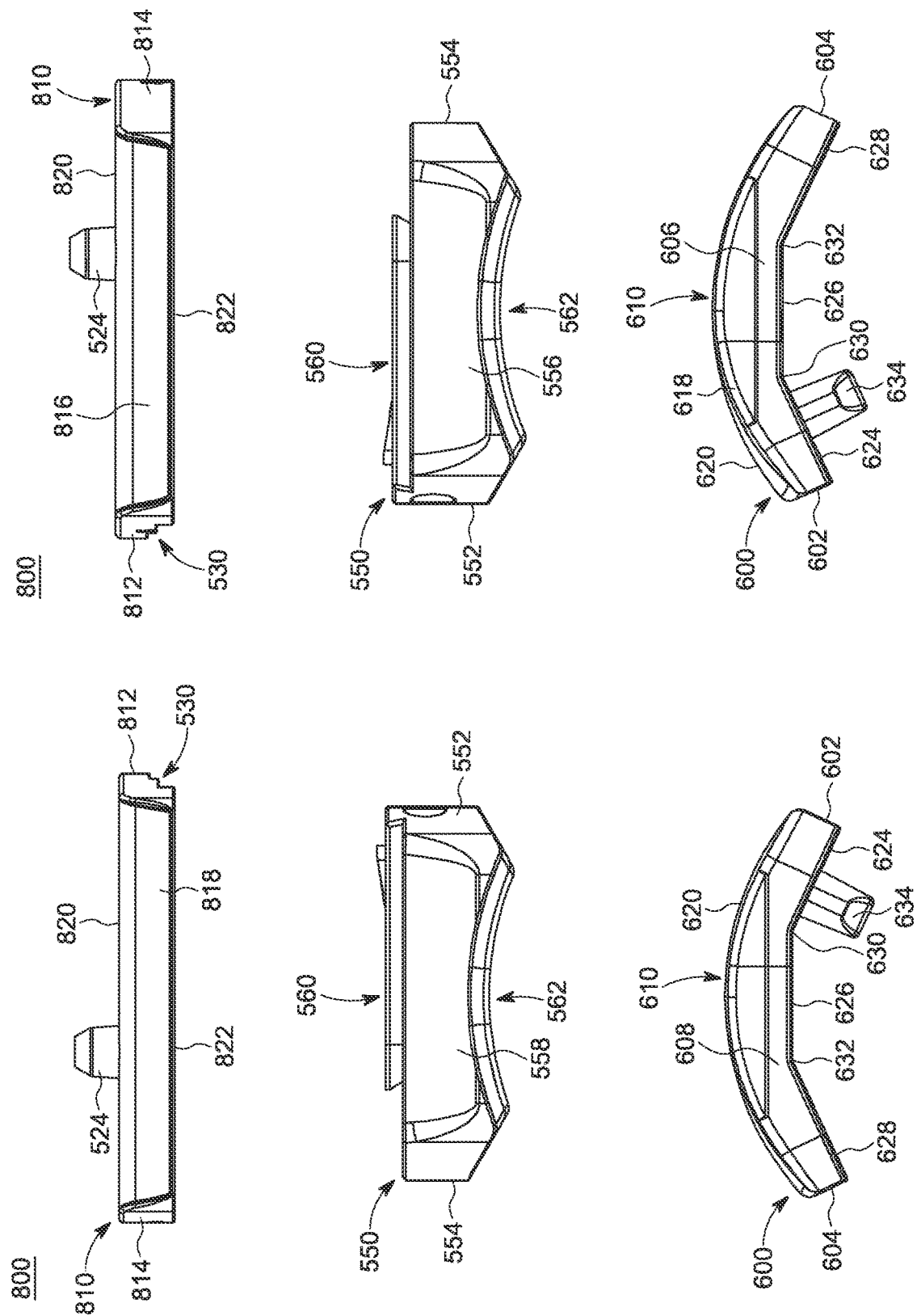

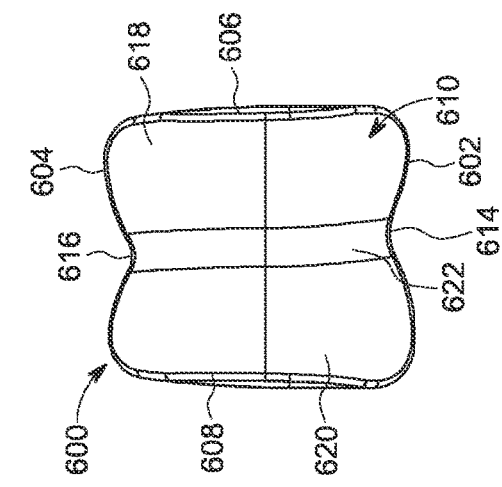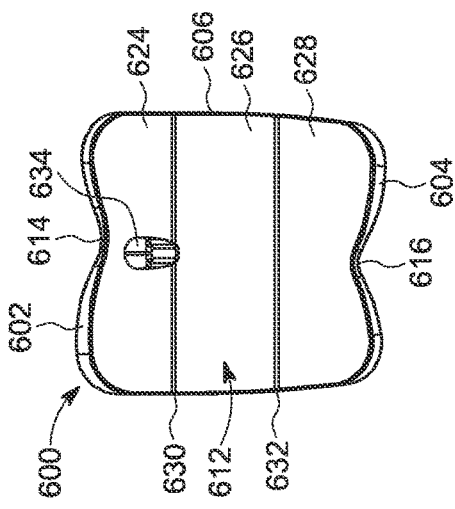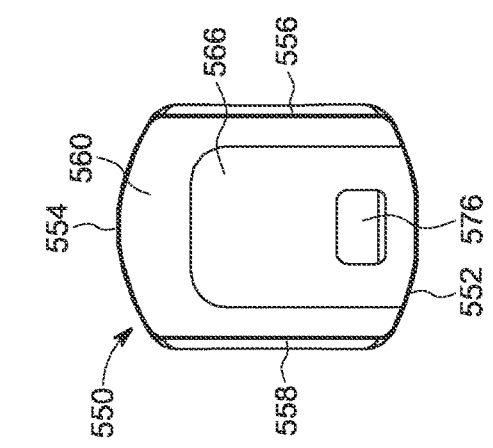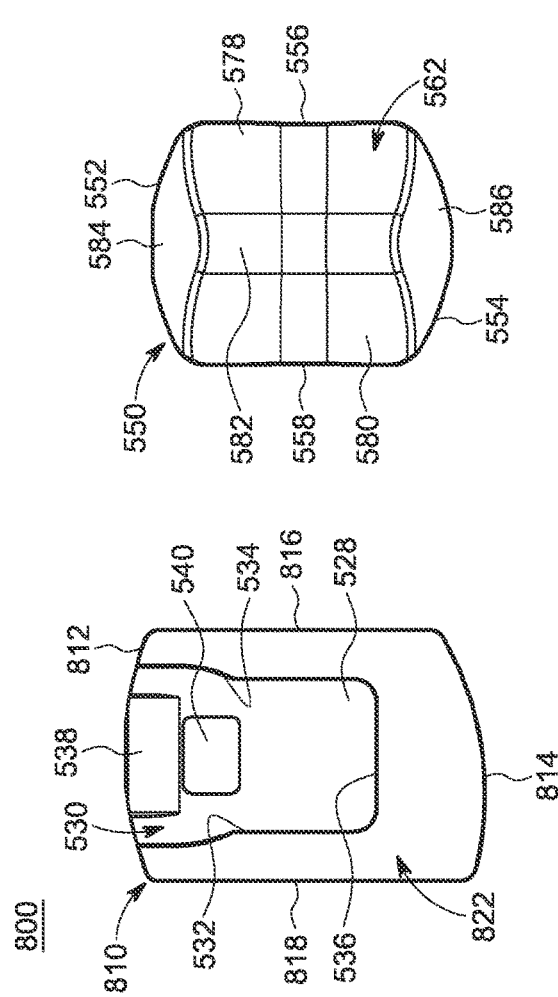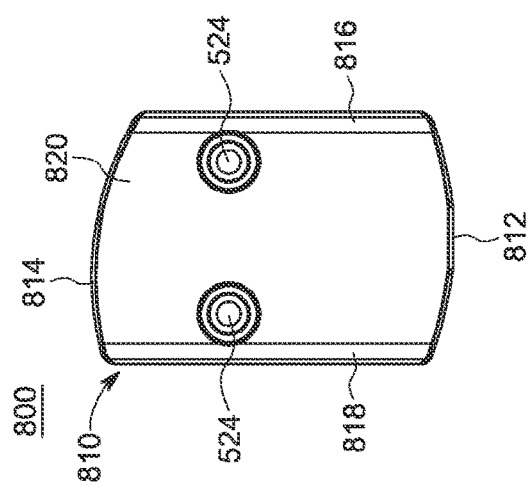
FIG. 90
FIG. 91

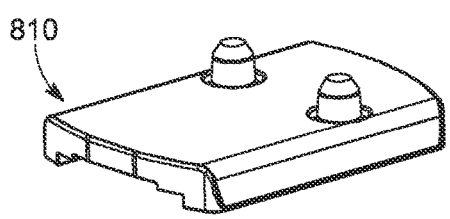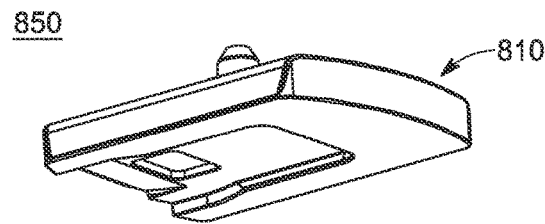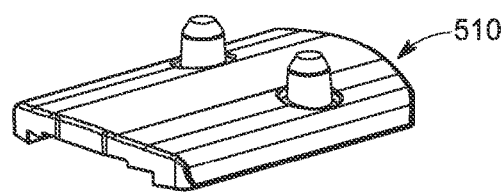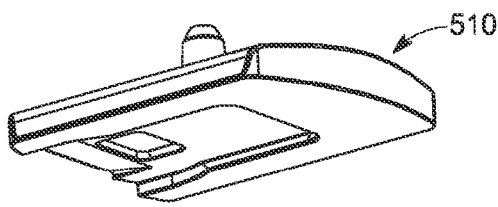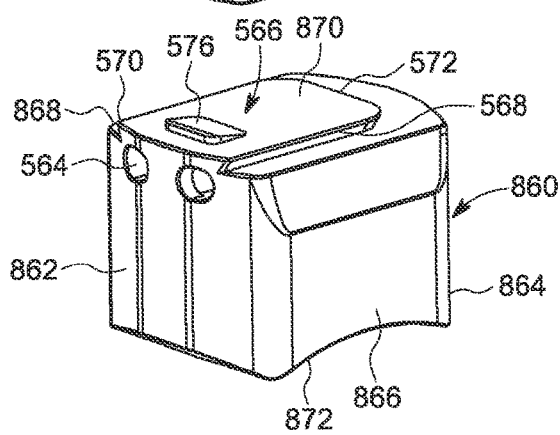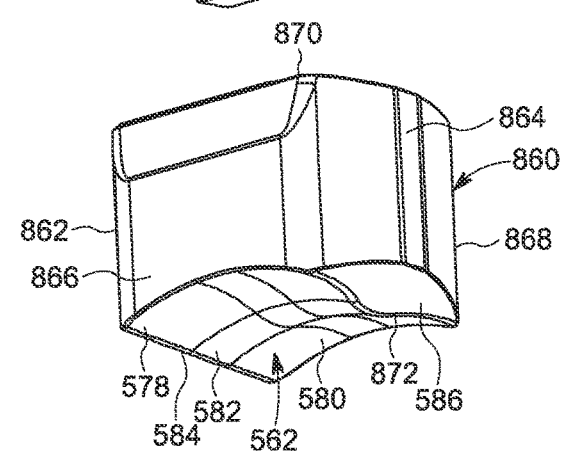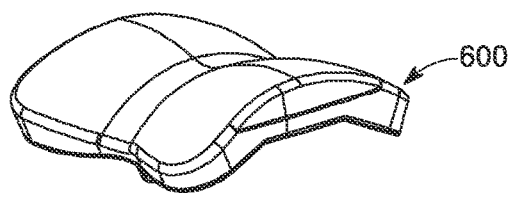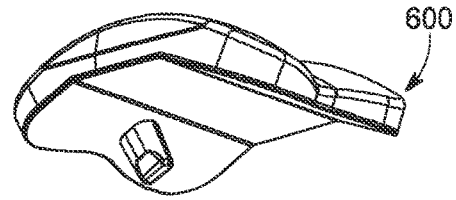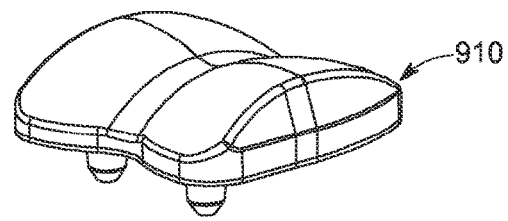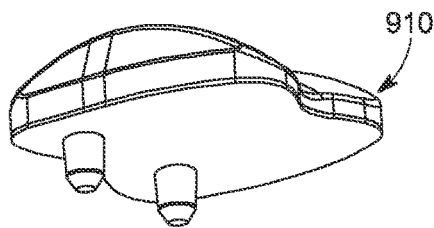
FIG. 92　　　　　　FIG. 93

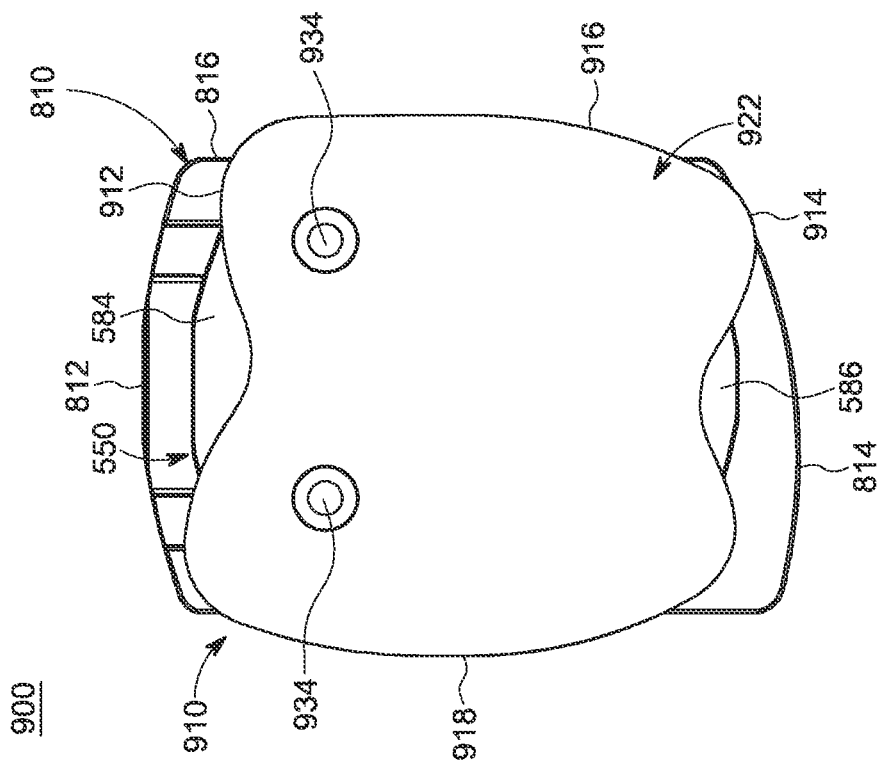
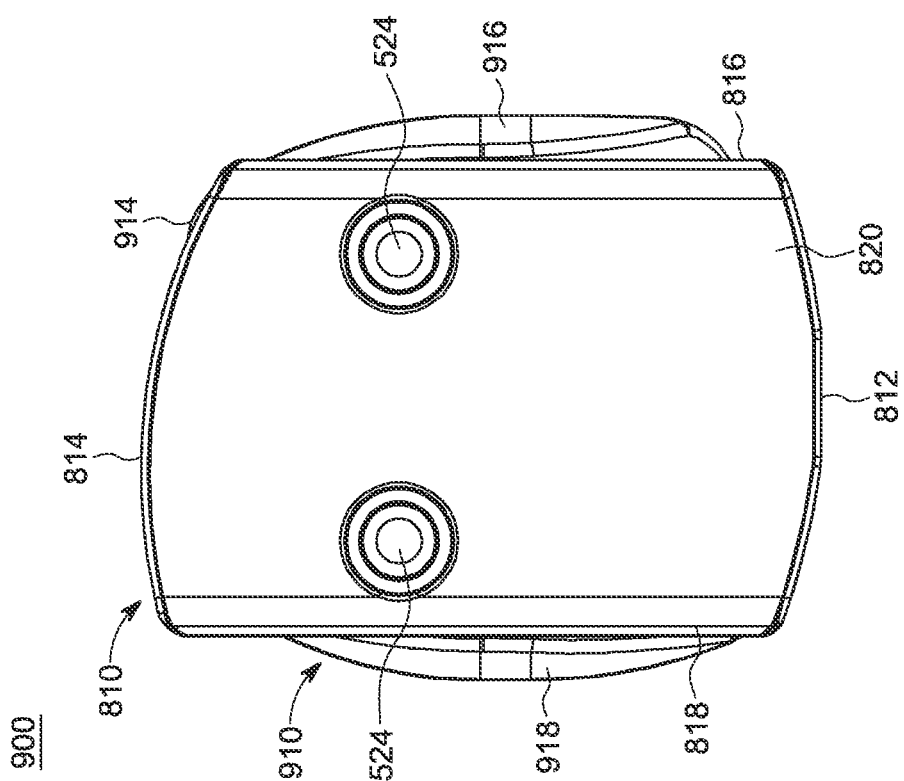
FIG. 101
FIG. 100

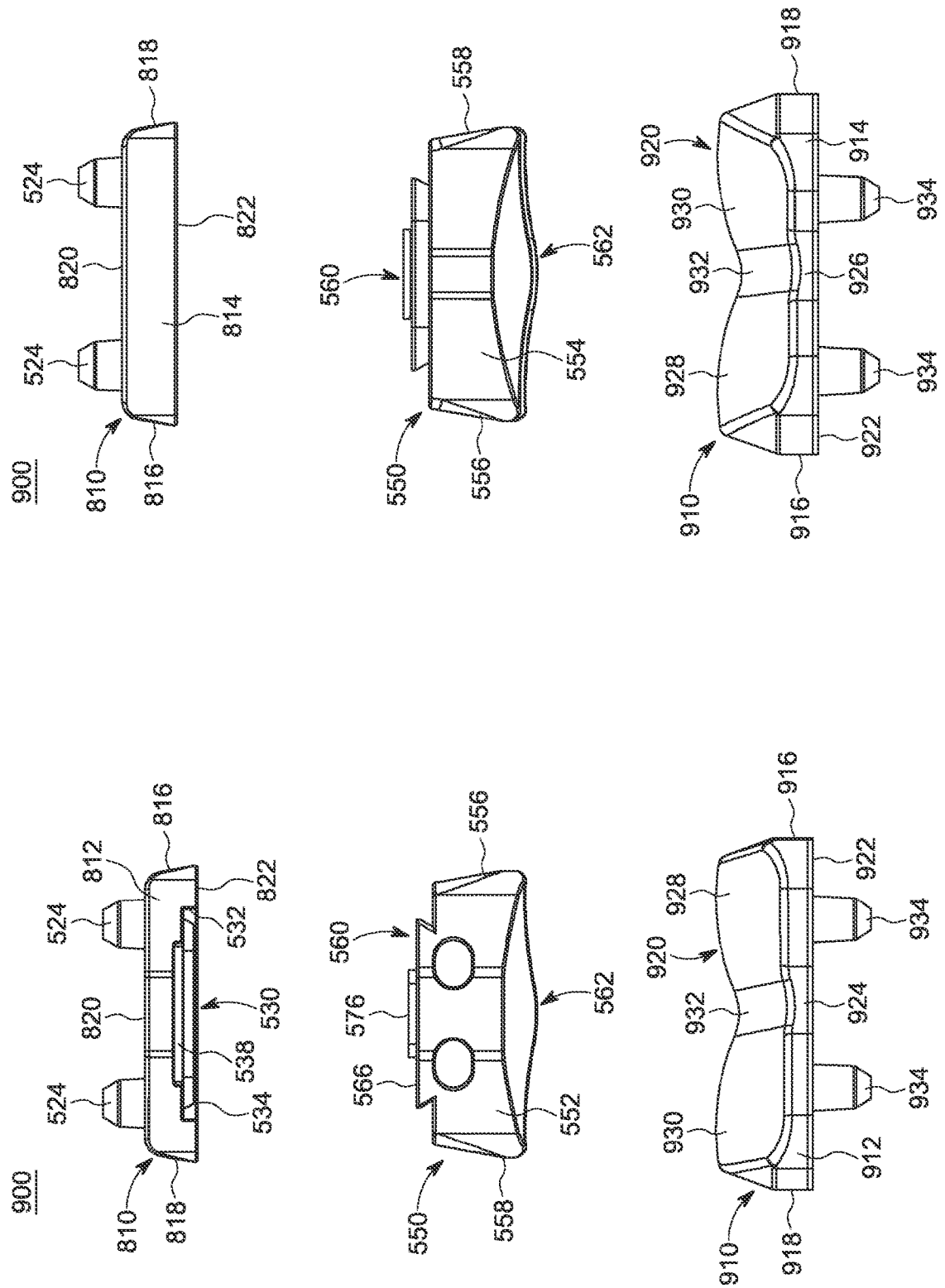

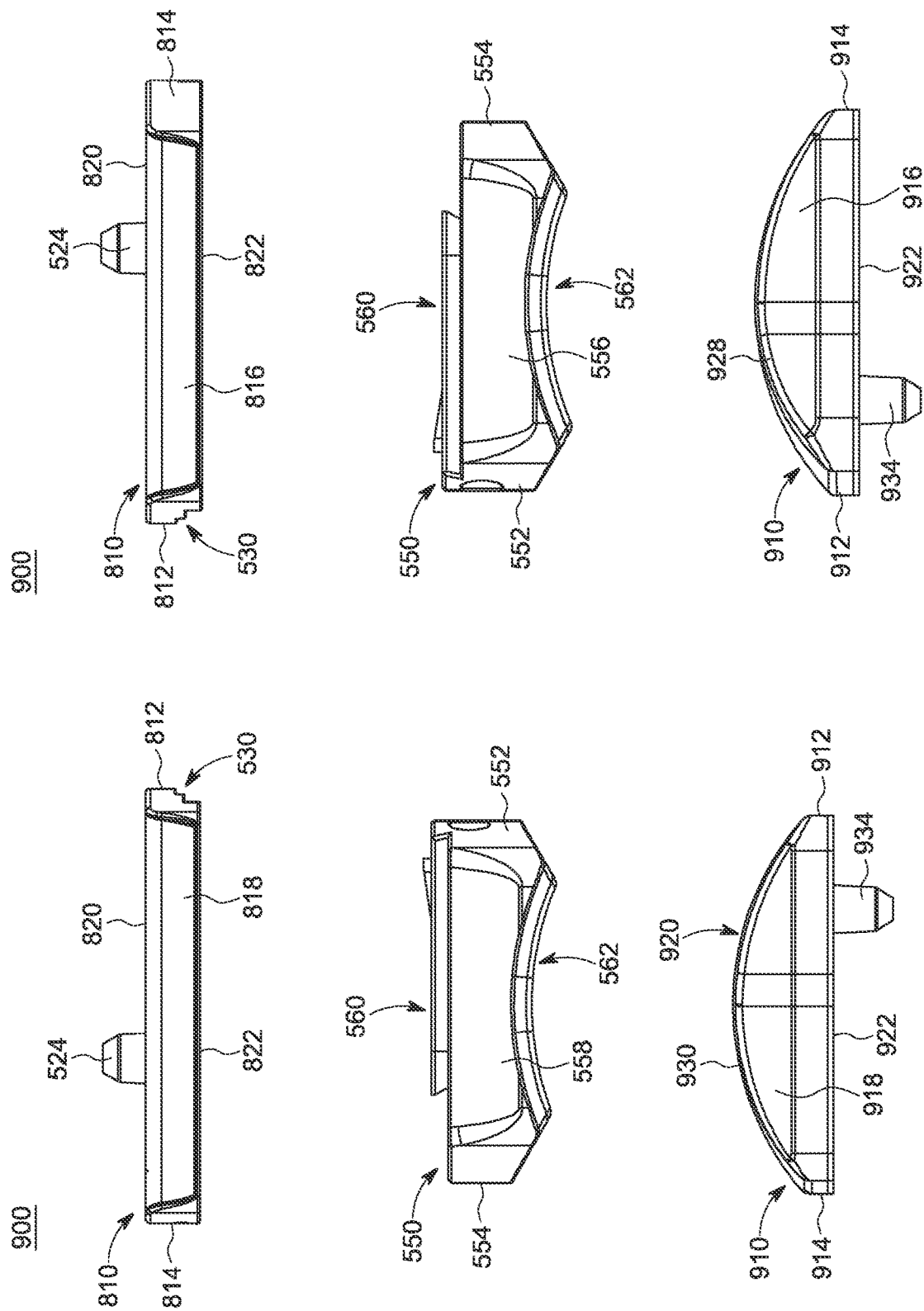

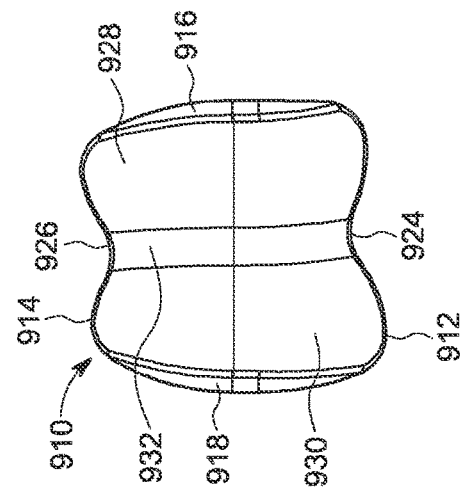
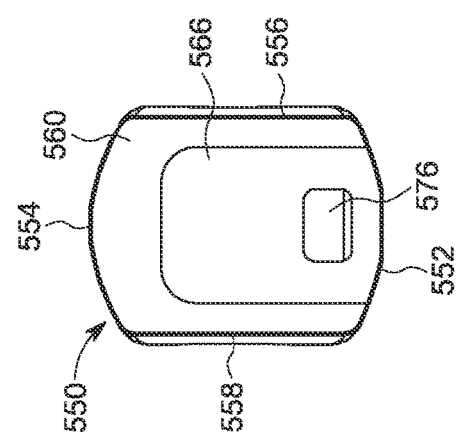
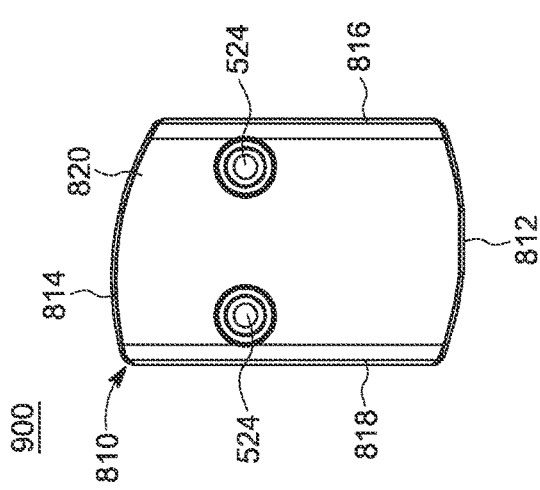
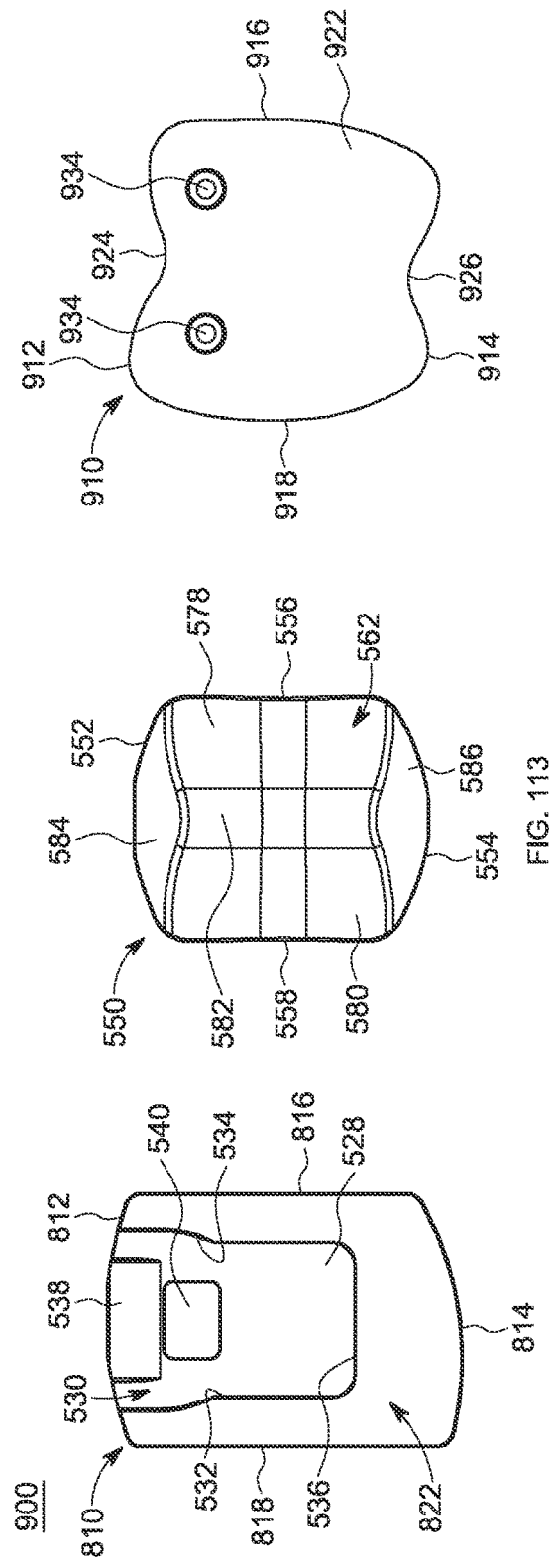
FIG. 112
FIG. 113

IMPLANTS AND METHODS OF USE AND ASSEMBLY

CROSS REFERENCE TO RELATED APPLICATION

This application is a continuation of PCT/US2019/029009 filed on Apr. 24, 2019 and entitled Implants and Methods of Use and Assembly, which claims priority benefit under 35 U.S.C. § 119(e) to U.S. provisional application No. 62/661,945 filed on Apr. 24, 2018 and entitled Implants and Methods of Use and Assembly, which are incorporated herein by reference in their entireties.

TECHNICAL FIELD

The present disclosure relates generally to general, podiatric, and orthopaedic surgery related to joint deformities. More specifically, but not exclusively, the present disclosure relates to implants, devices, and methods for maintaining, correcting and/or resurfacing joint surfaces.

BACKGROUND OF THE INVENTION

Currently available implants for total ankle replacement may experience loosening of the tibial component. In addition, some currently available implants for total ankle replacement may cause stress concentrations in the medial malleolus. In other currently available implants for total ankle replacement, the sizing of the talus component lacks proper bone coverage. Finally, some currently available implants for total ankle replacement lack vertical stabilization features on the tibia.

Accordingly, it is an object of the present invention to overcome one or more of the above-described drawbacks and/or disadvantages of the currently used implants. For example, in view of the deficiencies of the current implants, it would be desirable to develop implants, devices, and/or systems which avoid loosening of the tibial component, remove the stress concentration from the medial malleolus, provide proper coverage of the talus bone, and provide features for vertical stabilization of the tibia.

SUMMARY OF THE INVENTION

The present disclosure is directed toward implants, devices and methods for use in maintaining, correcting and/or resurfacing joint surfaces.

In one aspect of the present disclosure provided herein, is an implant. The implant including a first member, a second member, and an insert with a top surface and a bottom surface, wherein the top surface couples to the first member and the bottom surface engages the second member.

In another aspect of the present disclosure provided herein, is method for using the implant. The method includes obtaining an implant. The implant includes a first member, a second member, and an insert with a top surface and a bottom surface. The top surface of the insert couples to the first member and the bottom surface of the insert engages the second member. The method also includes making an incision to expose a joint with a first bone and a second bone and preparing the bones for receiving the implant. The method further includes coupling the first member to the first bone and the second member to the second bone. In addition, the method includes inserting a second end of the insert into a first end of the first member. Then, the method includes closing the incision.

In yet another aspect of the present disclosure provided herein, is a kit. The kit including a plurality of first members of an implant, wherein the first members include a top surface and a bottom surface, a plurality of second members of the implant, wherein the second members include a top surface and a bottom surface, and a plurality of inserts of the implant, wherein the plurality of inserts include a top surface and a bottom surface. The top surface of each of the plurality of first members includes a radius and the radius is the same for each of the first members and the bottom surface of each of the plurality of second members has the same dimensions for each of the second members.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 11 is an exploded, first end view of the implant of FIG. 1, in accordance with an aspect of the present disclosure;

FIG. 12 is an exploded, second end view of the implant of FIG. 1, in accordance with an aspect of the present disclosure;

FIG. 13 is an exploded, first side view of the implant of FIG. 1, in accordance with an aspect of the present disclosure;

FIG. 14 is an exploded, second side view of the implant of FIG. 1, in accordance with an aspect of the present disclosure;

FIG. 28 is an exploded, first end view of the implant of FIG. 18, in accordance with an aspect of the present disclosure;

FIG. 29 is an exploded, second end view of the implant of FIG. 18, in accordance with an aspect of the present disclosure;

FIG. 30 is an exploded, first side view of the implant of FIG. 18, in accordance with an aspect of the present disclosure;

FIG. 31 is an exploded, second side view of the implant of FIG. 18, in accordance with an aspect of the present disclosure;

FIG. 38 is a top view of the implant of FIG. 36, in accordance with an aspect of the present disclosure;

FIG. 39 is a bottom view of the implant of FIG. 36, in accordance with an aspect of the present disclosure;

FIG. 46 is an exploded, first end view of the implant of FIG. 36, in accordance with an aspect of the present disclosure;

FIG. 47 is an exploded, second end view of the implant of FIG. 36, in accordance with an aspect of the present disclosure;

FIG. 48 is an exploded, first side view of the implant of FIG. 36, in accordance with an aspect of the present disclosure;

FIG. 49 is an exploded, second side view of the implant of FIG. 36, in accordance with an aspect of the present disclosure;

FIG. 50 is an exploded, top view of the implant of FIG. 36, in accordance with an aspect of the present disclosure;

FIG. 51 is an exploded, bottom view of the implant of FIG. 36, in accordance with an aspect of the present disclosure;

FIG. 86 is an exploded, first end view of the implant of FIG. 76, in accordance with an aspect of the present disclosure;

FIG. 87 is an exploded, second end view of the implant of FIG. 76, in accordance with an aspect of the present disclosure;

FIG. 88 is an exploded, first side view of the implant of FIG. 76, in accordance with an aspect of the present disclosure;

FIG. 89 is an exploded, second view of the implant of FIG. 76, in accordance with an aspect of the present disclosure;

FIG. 90 is an exploded, top view of the implant of FIG. 76, in accordance with an aspect of the present disclosure;

FIG. 91 is an exploded, bottom view of the implant of FIG. 76, in accordance with an aspect of the present disclosure;

FIG. 92 is an exploded, first perspective view of an implant kit, in accordance with an aspect of the present disclosure;

FIG. 93 is an exploded, second perspective view of the implant kit of FIG. 92, in accordance with an aspect of the present disclosure;

FIG. 100 is a top view of the implant of FIG. 98, in accordance with an aspect of the present disclosure;

FIG. 101 is a bottom view of the implant of FIG. 98, in accordance with an aspect of the present disclosure;

FIG. 108 is an exploded, first end view of the implant of FIG. 98, in accordance with an aspect of the present disclosure;

FIG. 109 is an exploded, second end view of the implant of FIG. 98, in accordance with an aspect of the present disclosure;

FIG. 110 is an exploded, first side view of the implant of FIG. 98, in accordance with an aspect of the present disclosure;

FIG. 111 is an exploded, second side view of the implant of FIG. 98, in accordance with an aspect of the present disclosure;

FIG. 112 is an exploded, top view of the implant of FIG. 98, in accordance with an aspect of the present disclosure;

FIG. 113 is an exploded, bottom view of the implant of FIG. 98, in accordance with an aspect of the present disclosure;

FIG. 119 is a first side view of the second member of FIG. 117, in accordance with an aspect of the present disclosure;

FIG. 120 is a second side view of the second member of FIG. 117, in accordance with an aspect of the present disclosure;

FIG. 121 is a first end view of the second member of FIG. 117, in accordance with an aspect of the present disclosure;

FIG. 122 is a second end view of the second member of FIG. 117, in accordance with an aspect of the present disclosure;

FIG. 123 is a perspective view of the first member of the implant of FIG. 36, in accordance with an aspect of the present disclosure; and FIG. 124 is a cross-sectional side view of the first member of FIG. 123 taken along line 124-124, in accordance with an aspect of the present disclosure.

DETAILED DESCRIPTION FOR CARRYING OUT THE INVENTION

Figure 1:
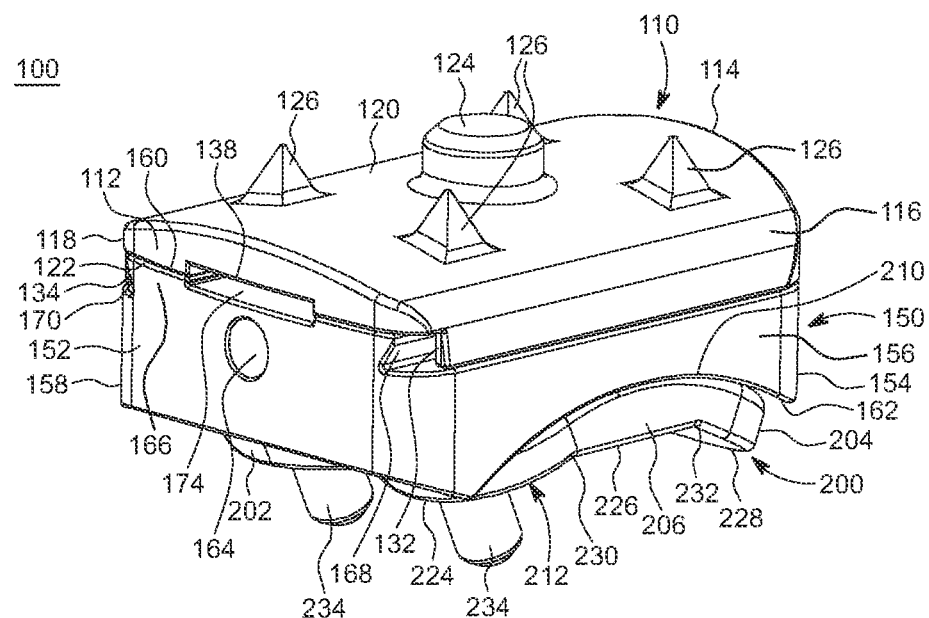
FIG. 1 is a first perspective view of one embodiment of an implant, in accordance with an aspect of the present disclosure.
Figure 2:
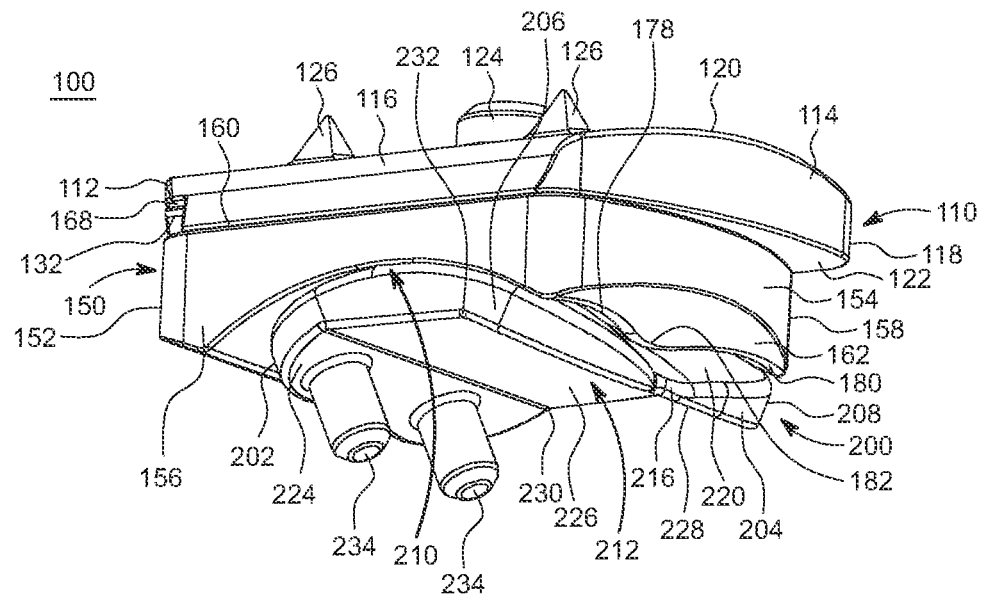
FIG. 2 is a second perspective view of the implant of FIG. 1, in accordance with an aspect of the present disclosure.
Figure 3:
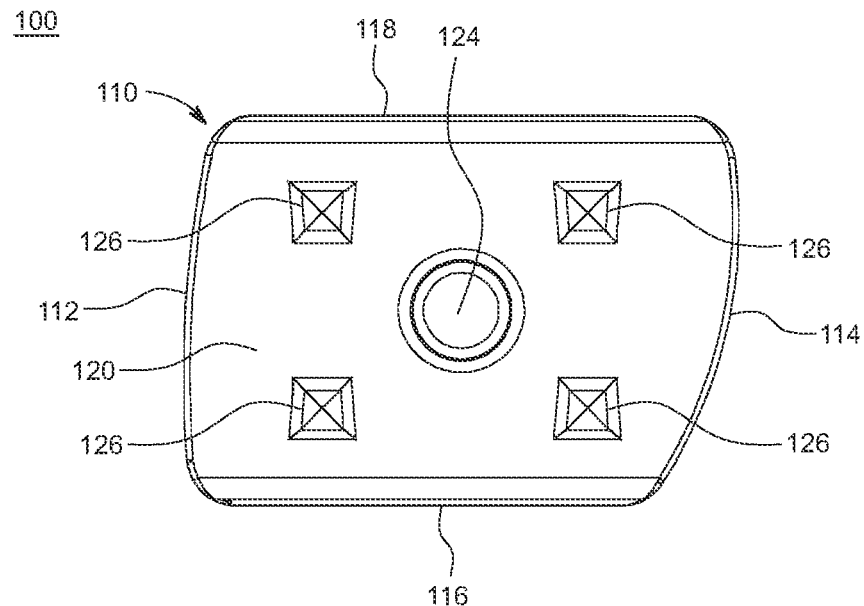
FIG. 3 is a top view of the implant of FIG. 1, in accordance with an aspect of the present disclosure.
Figure 4:
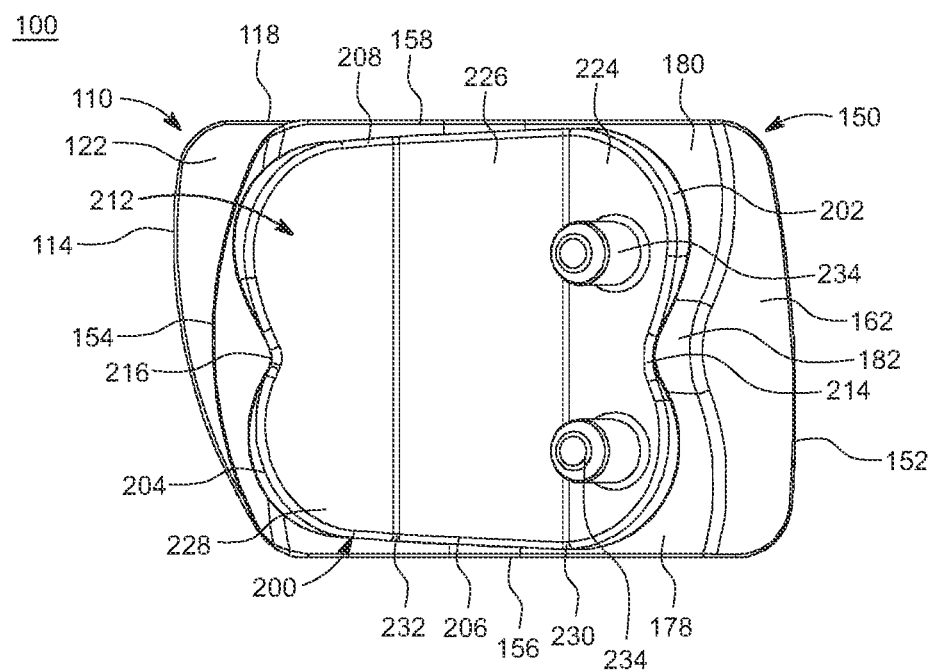
FIG. 4 is a bottom view of the implant of FIG. 1, in accordance with an aspect of the present disclosure.
Figure 5:
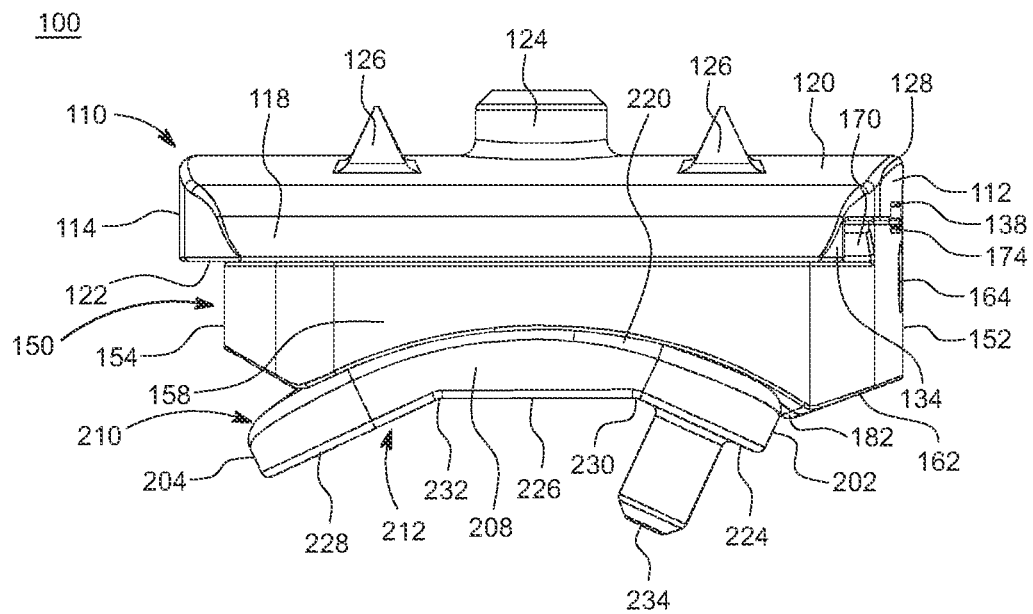
FIG. 5 is a first side view of the implant of FIG. 1, in accordance with an aspect of the present disclosure.
Figure 6:
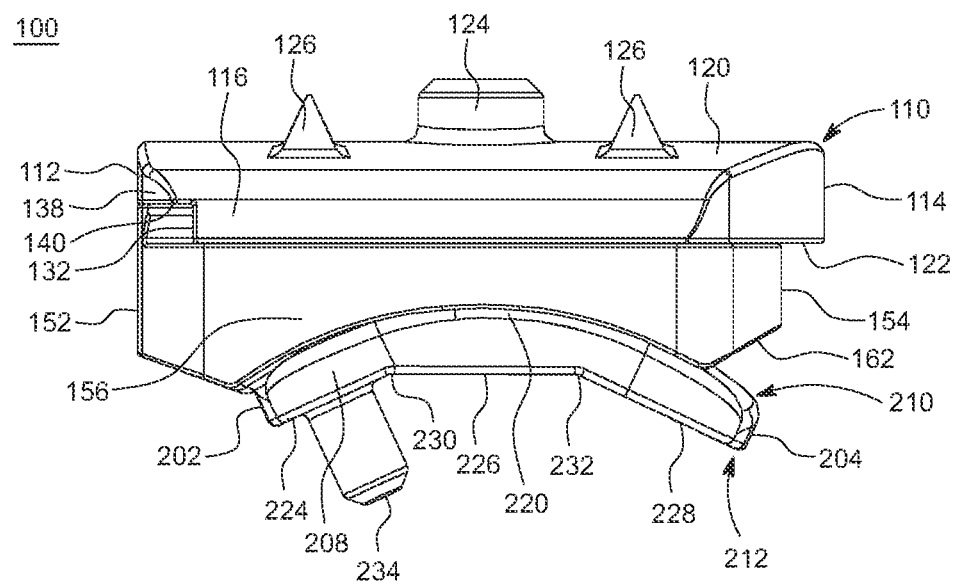
FIG. 6 is a second side view of the implant of FIG. 1, in accordance with an aspect of the present disclosure.
Figure 7:
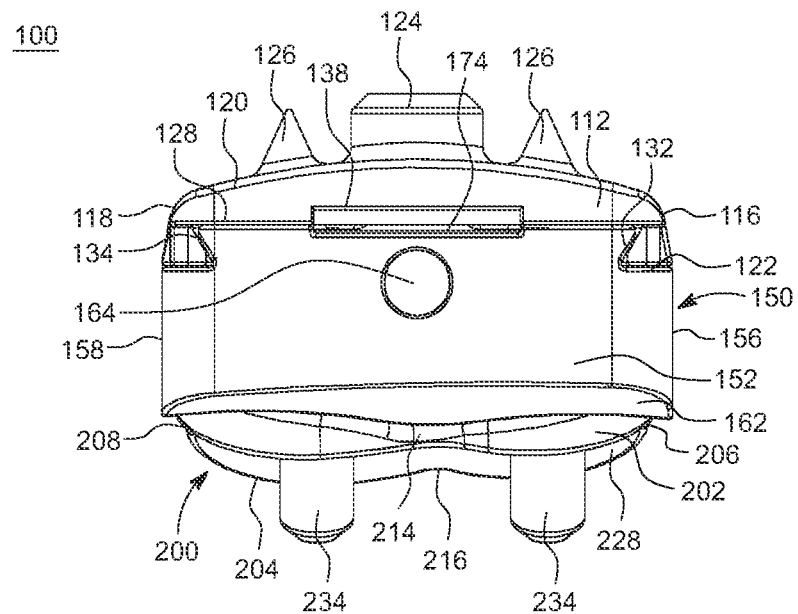
FIG. 7 is a first end view of the implant of FIG. 1, in accordance with an aspect of the present disclosure.
Figure 8:
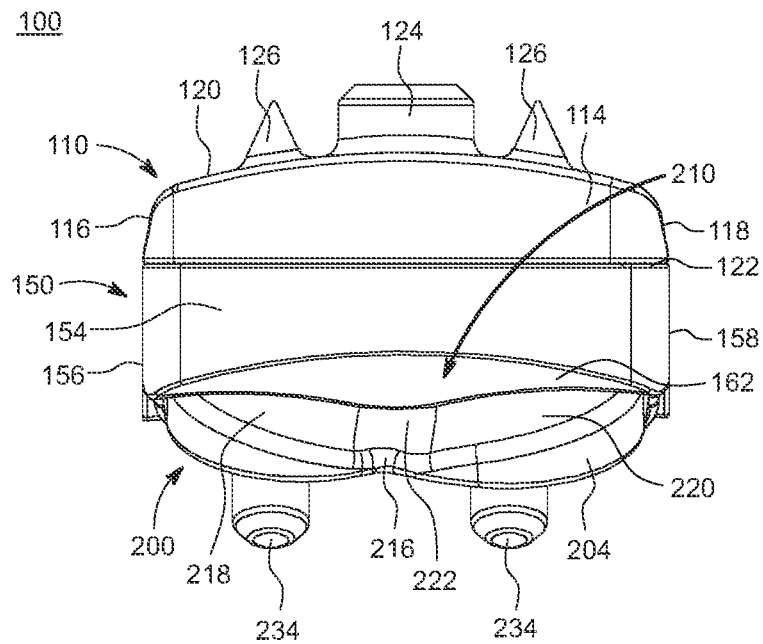
FIG. 8 is a second end view of the implant of FIG. 1, in accordance with an aspect of the present disclosure.
Figure 9:
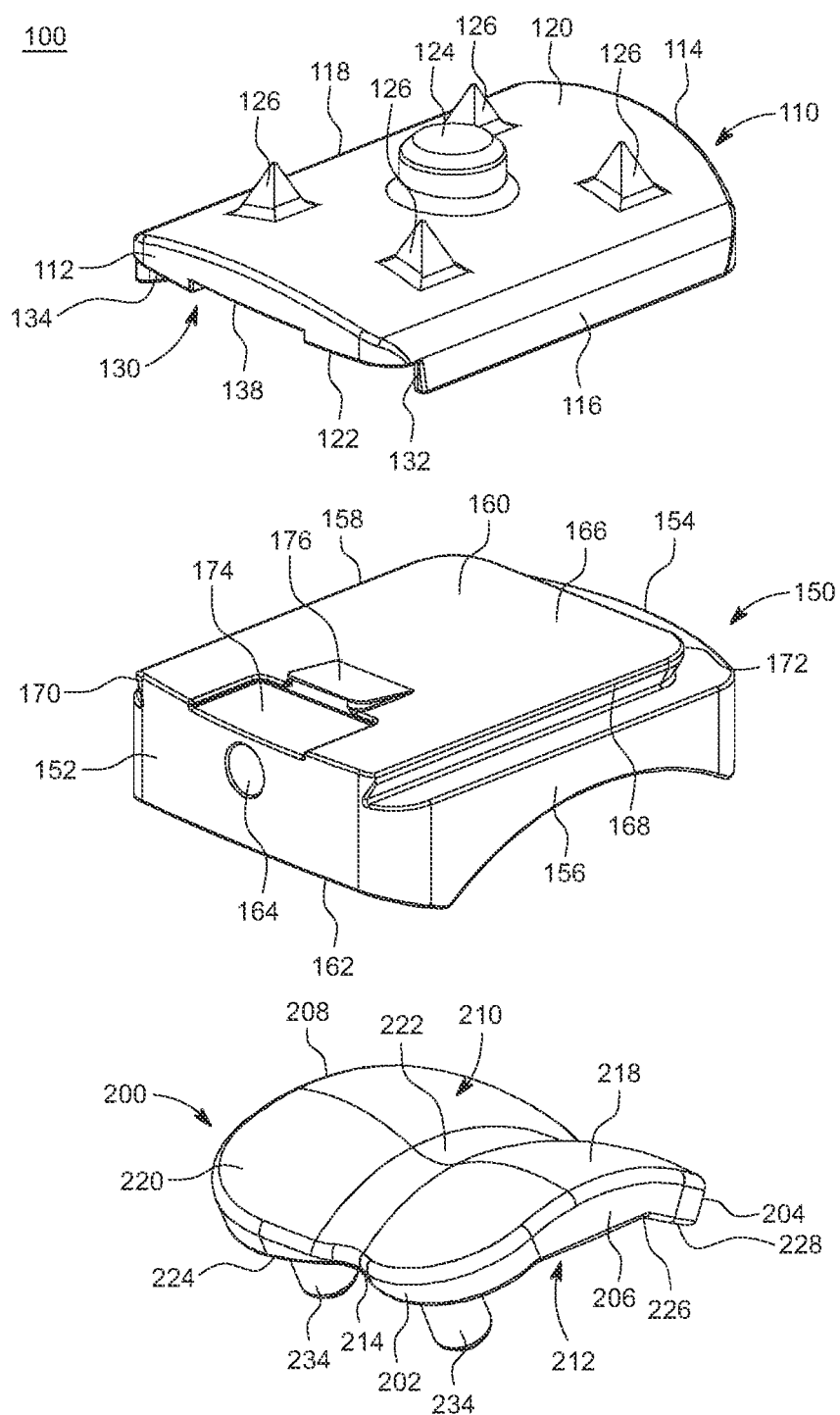
FIG. 9 is a first exploded, perspective view of the implant of FIG. 1, in accordance with an aspect of the present disclosure.

Generally stated, disclosed herein are devices, systems, and methods for maintaining, correcting and/or resurfacing joint surfaces. Further, methods for using the implants, devices, and methods for maintaining, correcting and/or resurfacing joint surfaces are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers to the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the ankle for brevity purposes, but it should be understood that the devices, systems, instrumentation and methods may be used with other bones of the body having similar structures.

Referring to the drawings, wherein like reference numerals are used to indicate like or analogous components throughout the several views, and with particular reference to FIGS. 1-16, there is illustrated an implant 100. The implant 100 includes a first member or tibia base 110, an insert 150, and a second member, talus component, or articulating member 200. The insert 150 includes a top surface 160 and a bottom surface 162. The top surface 160 of the insert 150 couples to the first member 110 and the bottom surface 162 engages the second member 200.

As shown in FIGS. 9-16, the first member 110 includes a first end or anterior end 112 opposite a second end or posterior end 114. The first member 110 also includes a first side or medial side 116 opposite a second side or lateral side 118. In addition, the first member 110 includes a top surface 120 opposite a bottom surface 122. The top surface 120 may include, for example, an arc shape or curvature extending between the first side 116 and the second side 118, as shown in FIGS. 7, 8, 11 and 12. The curvature may have, for example, an arc radius ranging from approximately 35 mm to 70 mm. In an alternative embodiment, the top surface 120 of the first member 110 may be, for example, flat as the top surface 120 extends between the first side 116 and the second side 118.

With continued reference to FIGS. 7, 8, 11, and 12, the top surface 120 of the first member 110 may also include, for example, sloped, tapered, or angled sides on the first side 116 and the second side 118 of the first member 110. The angle of the sides of the top surface 120 at the first and second sides 116, 118 may be, for example, approximately 8° to 15° from vertical and more specifically approximately 10° from vertical. The edges of the first and second sides 116, 118 of the first member 110 may be, for example, rounded or curved. The rounded edges may have, for example, a radii of approximately 1.25 mm to 2.4 mm and more specifically approximately 1.75 mm to 2.4 mm. The first member 110 may have an outer perimeter shape that may be, for example, a quadrilateral shape, such as, a generally trapezoidal shape from a top or bottom view, as shown in FIGS. 3, 4, 15, and 16. The first and second sides 116, 118 may be generally parallel and the first end 112 and second end 114 may be, for example, angled or curved as they extend from the first side 116 to the second side 118. In an embodiment, the length of the first or medial side 116 may be, for example, shorter than the length of the second or lateral side 118. The angle of the first end 112 may be, for example, smaller than the angle of the second end 114. The top surface 120, first side 116 and second side 118 may be, for example, textured or coated to provide a friction-stabilization surface and to allow for bone on-growth. The textured surface may be, for example, plasma sprayed biocompatible material, such as, commercially-pure titanium, or another biocompatible material as known by one of ordinary skill in the art.

With continued reference to FIGS. 9-16, the top surface 120 of the first member 110 includes at least one peg or vertical peg 124 extending away from the top surface 120. The top surface 120 of the first member 110 also includes at least one protrusion, spike, pyramid, or cone 126 extending away from the top surface 120. The at least one protrusion 126 may be, for example, spaced from the at least one peg 124. The at least one protrusion 126 may be, for example, four protrusions 126, although alternative numbers of protrusions 126 are also contemplated. The protrusions 126 may be, for example, positioned equally spaced around the at least one peg 124. The at least one peg 124 and at least one protrusion 126 may not be, for example, textured, rather the at least one peg 124 and at least one protrusion 126 may be smooth to decrease bone resorption at the resection level.

Figure 10:
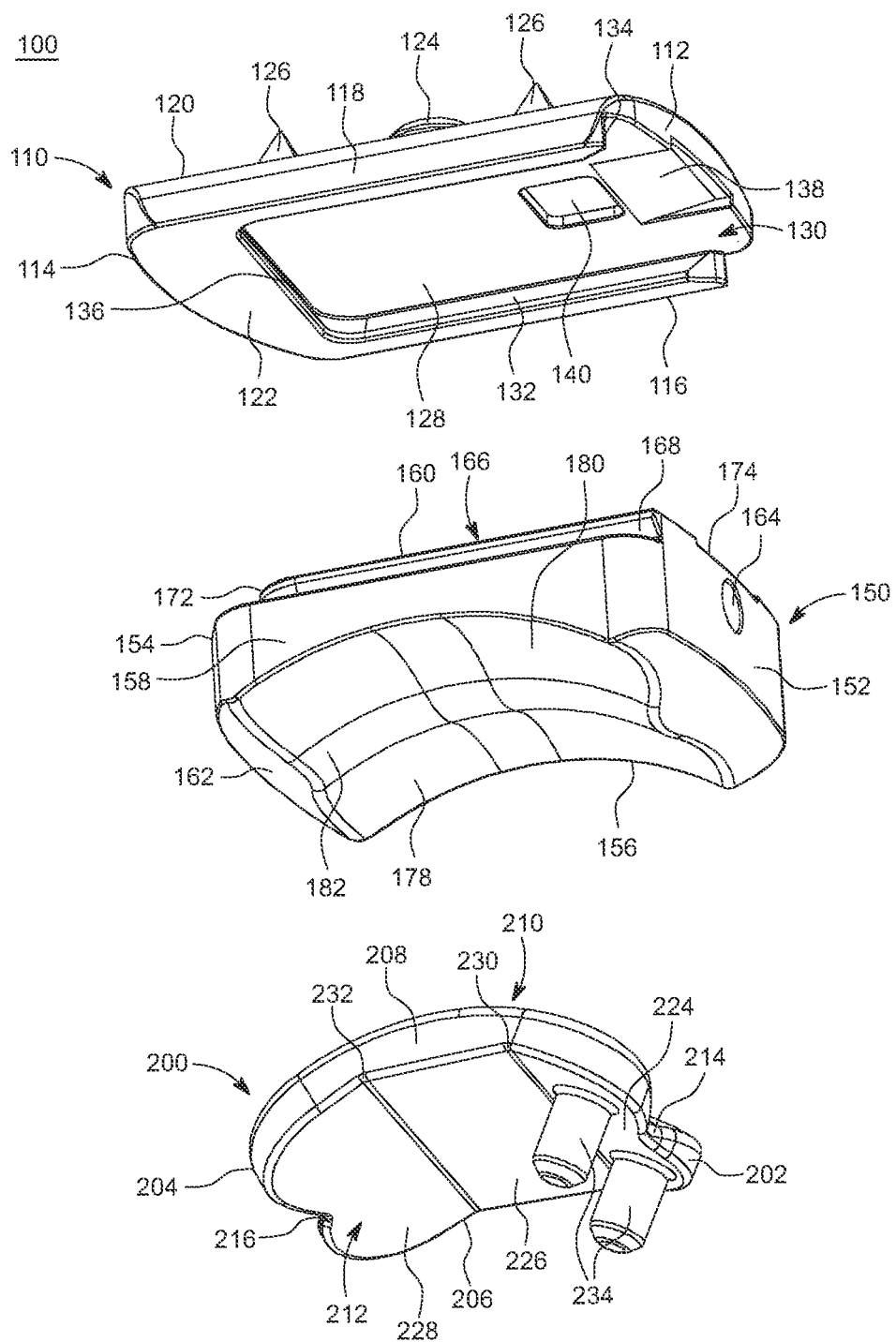
FIG. 10 is a second exploded, perspective view of the implant of FIG. 1, in accordance with an aspect of the present disclosure.
Figure 16:
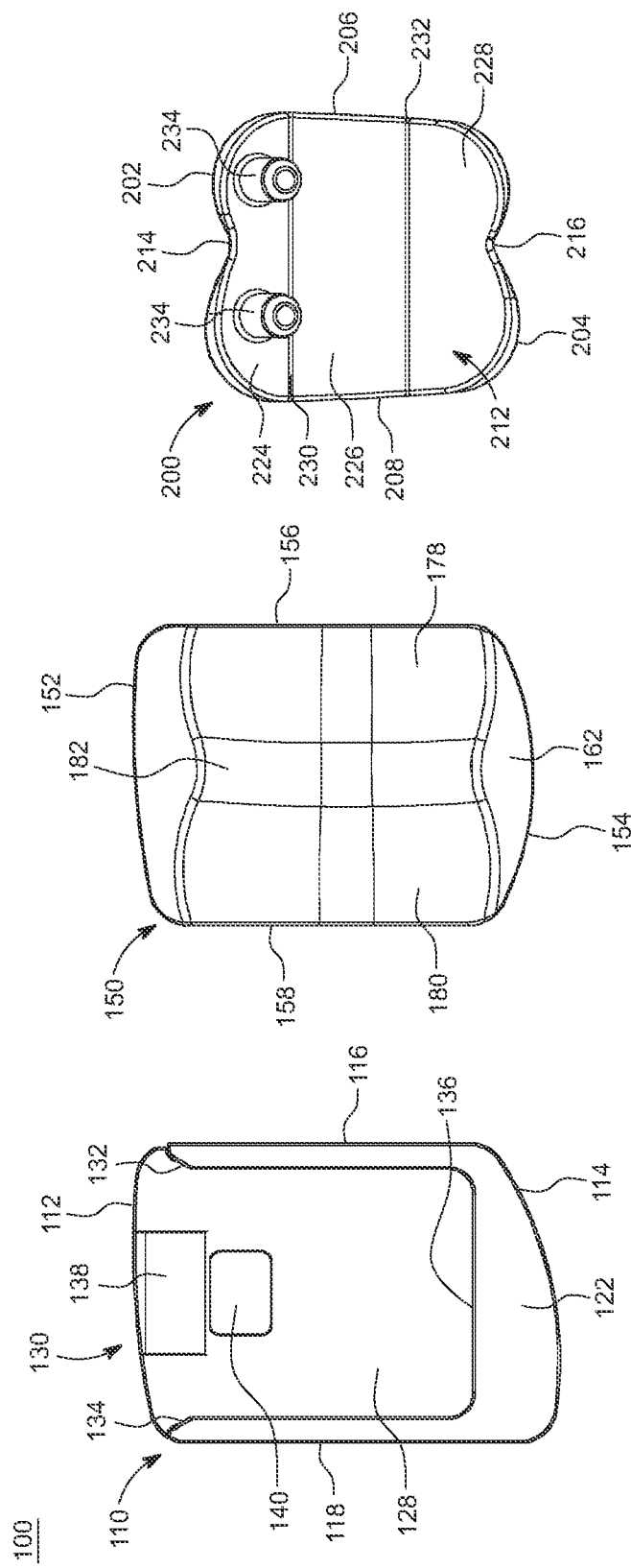
FIG. 16 is an exploded, bottom of the implant of FIG. 1, in accordance with an aspect of the present disclosure.

Referring now to FIGS. 10 and 16, the bottom surface 122 of the first member 110 is shown. The bottom surface 122 includes a recessed region or engagement region 128 extending into the first member 110 from the bottom surface 122 toward the top surface 120. The first member 110 may come in multiple sizes for use with patient's having different size tibia bones and the recessed region 128 of each of the first members 110 will be, for example, sized and shaped the same to allow for replacement of the first member 110 as needed. The bottom surface 122 also includes an engagement channel 130 extending from the first end 112 into the recessed region 128. In addition, the bottom surface 122 of the first member 110 includes a first engagement feature or first female dovetail portion 132 extending from the first side 116 into the recessed region 128, a second engagement feature or second female dovetail portion 134 extending from the second side 118 into the recessed region 128, and a third engagement feature or third female dovetail portion 136 extending from a position near the second end 114 into the recessed region 128. The bottom surface 122 of the first member 110 also includes a slot or removal engagement feature 138 and a locking groove 140 positioned adjacent to the slot 138. The slot 138 may be, for example, angled as the slot 138 extends from the first end 112 toward the locking groove 140.

Figure 15:
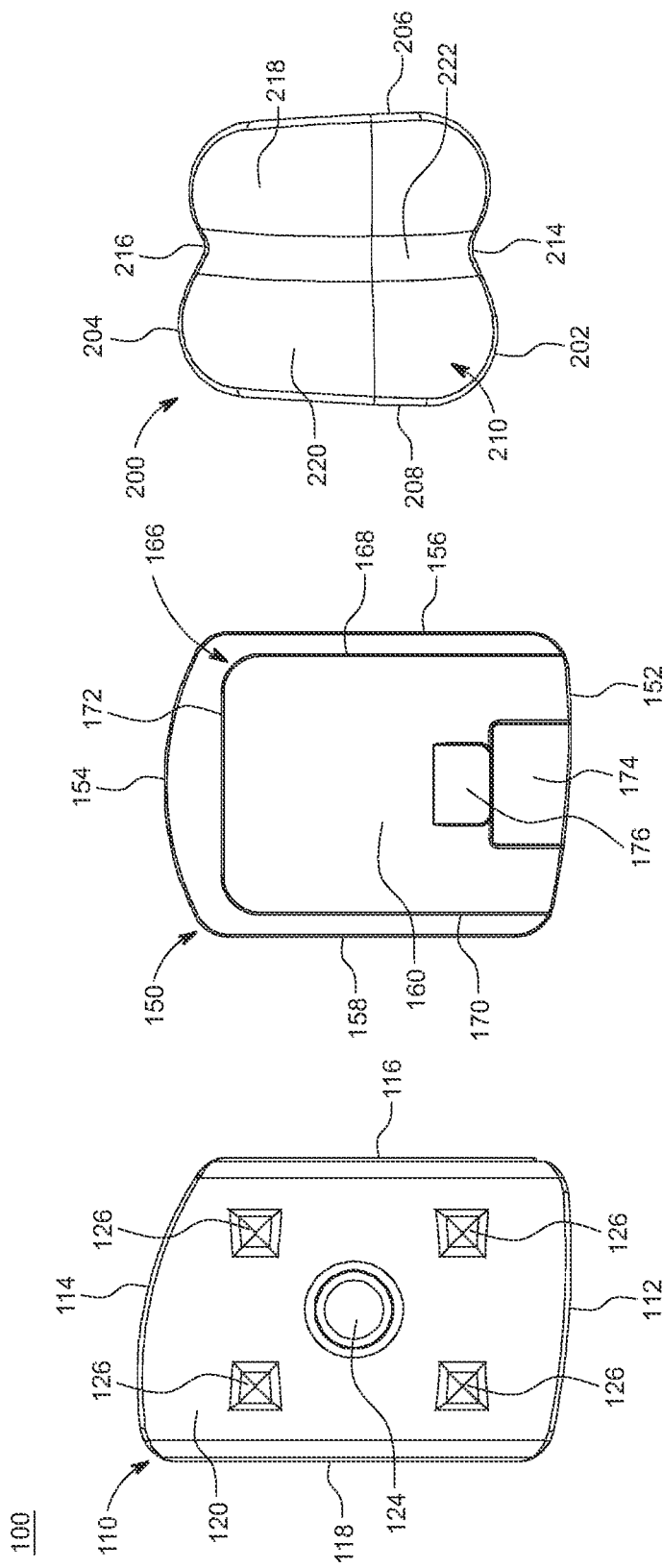
FIG. 15 is an exploded, top view of the implant of FIG. 1, in accordance with an aspect of the present disclosure.

Referring now to FIGS. 1-16, the second member, talus component or articulating member 200 has a first end or anterior end 202 opposite a second end or posterior end 204. The second member 200 also has a first side or medial side 206 opposite a second side or lateral side 208. In addition, the second member 200 has a top surface or articulating surface 210 opposite a bottom surface or bone engagement surface 212. The second member 200 may have, for example, a trapezium shape, as shown in FIGS. 15 and 16. The first and second sides 206, 208 may be, for example, angled as the sides 206, 208 extend from the first end 202 to the second end 204. The sides 206, 208 may be angled, for example, approximately 5° to 12°, and more preferably approximately 10°, as they extend away from the first end 202. The first side 206 may be, for example, shorter than the second side 208. The second member 200 includes an anterior recess 214 extending into the first end 202. The anterior recess 214 may be, for example, positioned near a midpoint of a lateral axis of the second member 200 or, alternatively may be medially biased. The second member 200 also includes a posterior recess 216 extending into the second end 204. The posterior recess 216 may be, for example, positioned near a midpoint of the lateral axis of the second member 200 or, alternatively may be medially biased.

As shown in FIGS. 9 and 11-15, the top surface 210 of the second member 200 includes a medial articulating surface 218 extending from the first side 206 of the second member 200 toward the second side 208. The top surface 210 may also include a lateral articulating surface 220 extending from the second side 208 of the second member 200 toward the first side 206. In addition, the top surface 210 also includes a central articulating portion 222 positioned at a point where the medial articulating surface 218 contacts the lateral articulating surface 220. The medial articulating surface 218 may include at least one first curvature along a longitudinal axis and at least one second curvature perpendicular to the longitudinal axis, as shown in FIG. 14. The lateral articulating surface 220 has at least one third curvature along the longitudinal axis and at least one fourth curvature perpendicular to the longitudinal axis. In addition, the central articulating portion 222 may have a concave curvature on the top surface 210 of the second member 200 and the medial and lateral articulating surfaces 218, 220 may have convex curvatures on the top surface 210 of the second member 200. The articulating surface 210 of the second member 200 may include, for example, a coronal radii and the coronal radii may have, for example, a range of approximately 12 mm to 26 mm for a size 1 second member 200, a range of approximately 14 mm to 30 mm for a size 3 second member 200, and a range of approximately 17 mm to 34 mm for a size 5 second member 200. The articulating surface 210 of the second member 200 may include, for example, a sagittal radii and the sagittal radii may have, for example, a range of approximately 18 mm to 25 mm for a size 1 second member 200, a range of approximately 20 mm to 28 mm for a size 3 second member 200, and a range of approximately 21 mm to 30 mm for a size 5 second member 200.

Referring now to FIGS. 2, 4-6, 10, 13, 14, and 16, the bottom surface 212 of the second member 200 may include a first portion 224, a second portion 226, and a third portion 228. The first portion 224, the second portion 226, and the third portion 228 may each have, for example, planar surfaces. The second portion 226 may be positioned between the first portion 224 and the third portion 228. The first portion 224 may extend, for example, from the first end 202 to a first transition point 230. The second portion 226 may extend, for example, from the first transition point 230 to a second transition point 232. The third portion 228 may extend, for example, from the second transition point 232 to the second end 204. The first portion 224 may extend away from the second portion 226 at a first angle and the third portion 228 may extend away from the second portion 226 at a second angle. The first angle may be, for example, approximately 25° to 35°, and the second angle may be, for example, approximately 25° to 35°. The bottom surface 212 of the second member 200 may be, for example, coated or textured with a biocompatible material. The texture or coating may be, for example, a plasma sprayed material, such as, a commercially-pure titanium or other biocompatible material, as known by one of ordinary skill in the art.

The bottom surface 212 of the second member 200 may also include at least one stem or peg 234 extending away from the first portion 224 of the bottom surface 212, as shown in FIGS. 1, 2, 4-14 and 16. The at least one stem 234 may be, for example, two stems 234, although other numbers of stems 234 are also contemplated. As depicted, the first stem 234 is positioned on the first portion 224 between the anterior recess 214 and the first side 206 and the second stem 234 is positioned on the first portion 224 between the anterior recess 214 and the second side 208, as shown in FIGS. 10 and 16. The stems 234 may be, for example, positioned slightly medially biased and may be offset, for example, approximately 1 mm from a midpoint of the second member 200. The at least one stem 234 may not be, for example, textured or coated, rather the at least one stem 234 may be smooth to decrease bone resorption at the resection level. The at least one stem 234 may have, for example, a cylindrical, pyramidal, or another quadrilateral prism shape.

Referring to FIGS. 1-16, the insert, polyethylene insert or articulating insert 150 is shown. The insert 150 includes a first end or anterior end 152 opposite a second end or posterior end 154. The insert 150 also includes a first side or medial side 156 opposite a second side or lateral side 158. In addition, the insert 150 includes a top surface 160 opposite a bottom surface 162. The first end 152 of the insert 150 includes an opening or cylinder 164 extending into the insert 150 from the first end 152 toward the second end 154. The opening 164 may be sized and shaped or configured to receive an instrument, for example, a self-tapping screw to engage the insert 150 and remove the insert 150 from the first member 110.

With continued reference to FIGS. 9 and 11-15, the top surface 160 of the insert 150 includes an engagement member or protrusion 166. The engagement member 166 includes a first engagement feature or first male dovetail 168 on the first side 156, a second engagement feature or second male dovetail 170 on the second side 158, and a third engagement feature or third male dovetail 172 on the second end 154. When the insert 150 is coupled to the first member 110, the first engagement feature 168 of the insert 150 may be configured or sized and shaped to engage the first engagement feature 132 of the first member 110, the second engagement feature 170 of the insert 150 may be configured or sized and shaped to engage the second engagement feature 134 of the first member 110, and the third engagement feature 172 of the insert 150 may be configured or sized and shaped to engage the third engagement feature 136 of the first member 110. The top surface 160 also may include a slot or removal engagement feature 174 and a locking tab or protrusion 176. The slot 174 may be, for example, positioned near and open to the first end 152. The locking tab 176 may be, for example, positioned adjacent to the slot 174 and extend away from the top surface 160 of the insert 150. The locking tab 176 may be configured or sized and shaped to engage the locking groove 140 of the bottom surface 122 of the first member 110.

Referring now to FIGS. 10-14 and 16, the bottom surface 162 of the insert 150 includes a first contact surface or medial contact surface 178, a second contact surface or lateral contact surface 180, and a central contact surface 182. The first contact surface 178 extends from the first side 156 of the insert 150 toward the second side 158. The second contact surface 180 extends from the second side 158 of the insert 150 toward the first side 156. The central contact surface or central sulcus 182 is positioned between the first contact surface 178 and the second contact surface 180. The first and second contact surfaces 178, 180 form a bi-condylar surface, as shown in FIGS. 7, 8, and 10-12. The centers of the radii of the bi-condylar surface may be, for example, spaced between approximately 18 mm and 26 mm for all sizes of the insert 150. More specifically, the centers of radii of the bi-condylar surface may be, for example, approximately 20 mm for a size 1 insert 150, approximately 22 mm for a size 3 insert 150, and approximately 24 mm for a size 5 insert 150. The first contact surface 178 includes at least one first curvature along a longitudinal axis and at least one second curvature along a lateral axis. The second contact surface 180 includes at least one third curvature along a longitudinal axis and at least one fourth curvature along a lateral axis. The central contact surface 182 includes at least one curvature. The curvatures of the first and second contact surfaces 178, 180 may be, for example, concave curvatures and the at least one curvature of the central contact surface 182 may be, for example, a convex curvature. The central contact surface 182 may provide, for example, stability in a medial-lateral direction. The central contact surface 182 may have, for example, a height ranging from approximately 1.5 mm and 2 mm. The insert 150 may also have a coronal radii and the coronal radii may be, for example, approximately 1.10× the coronal radii of the talus. In addition, the insert 150 may have at least one sagittal radii. The at least one sagittal radii of the insert 150 may be, for example, multiple tangent and/or continuous radii, which may include varying levels of conformity with the sagittal radii of the second member 200. The sagittal radii may have, for example, a range of approximately 25 mm to 34 mm for all sizes of the insert 150. More specifically, the sagittal radii may be, for example, approximately 25 mm to 26 mm for the size 1 insert 150 and approximately 33 mm to 34 mm for the size 5 insert 150. In an embodiment the sagittal radii may be, for example, 37.6 mm for size 1 and 32.4 for size 5.

As shown in FIGS. 1-8, when assembled and/or implanted, the top surface 160 of the insert 150 couples to a bottom surface 122 of the first member 110. In addition, the top surface 210 of the second member 200 is configured or sized and shaped to articulate with the bottom surface 162 of the insert 150. Specifically, the medial articulating surface 218 of the second member 200 is configured to articulate with the first contact surface 178 of the insert 150, the lateral articulating surface 220 of the second member 200 is configured to articulate with the second contact surface 180 of the insert 150, and the central portion 222 of the second member 200 is configured to articulate with the third contact surface 182 of the insert 150.

Figure 17:
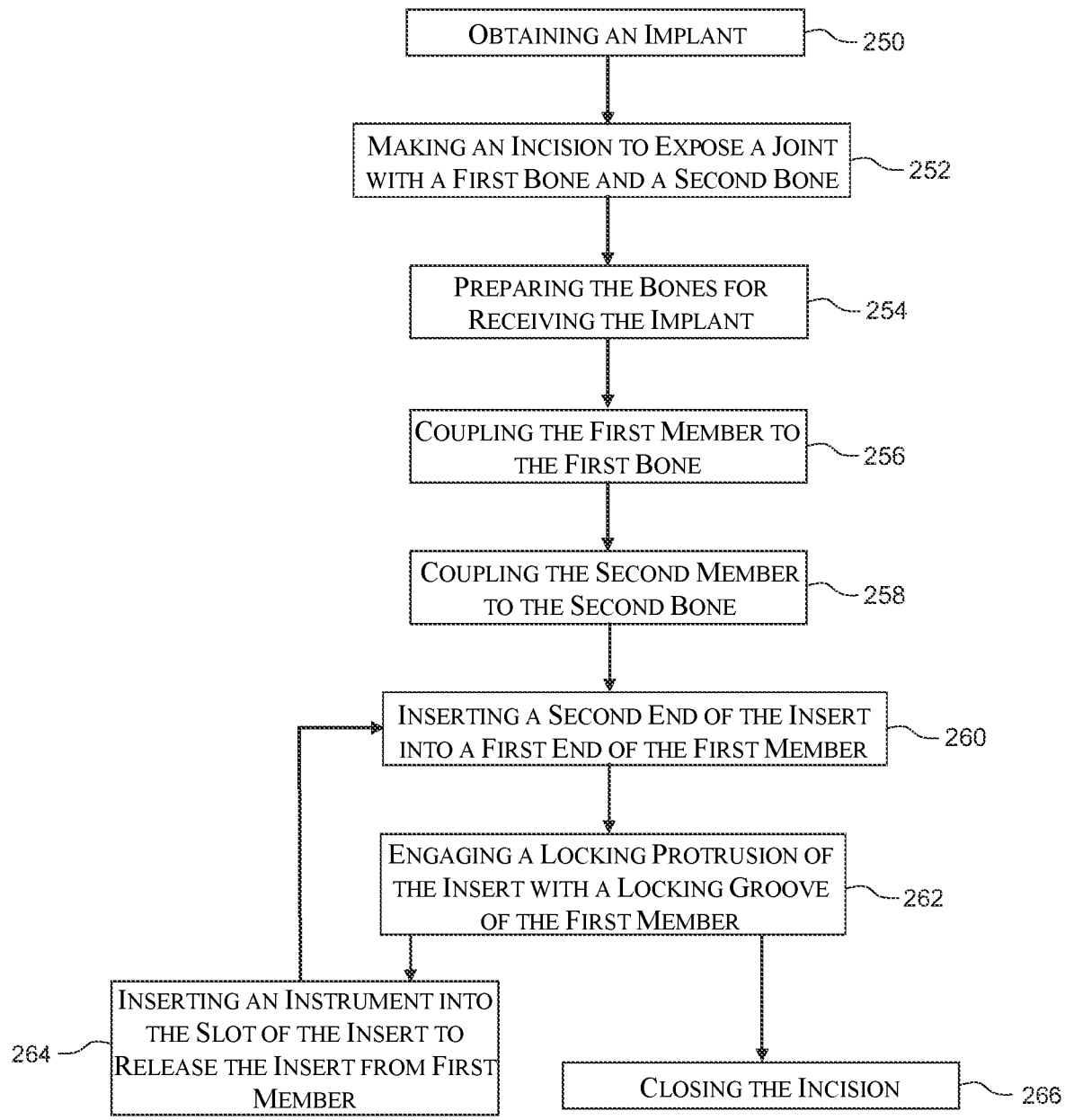
FIG. 17 depicts a method of inserting the implant of FIG. 1 into a joint, in accordance with an aspect of the present invention.
Figure 18:
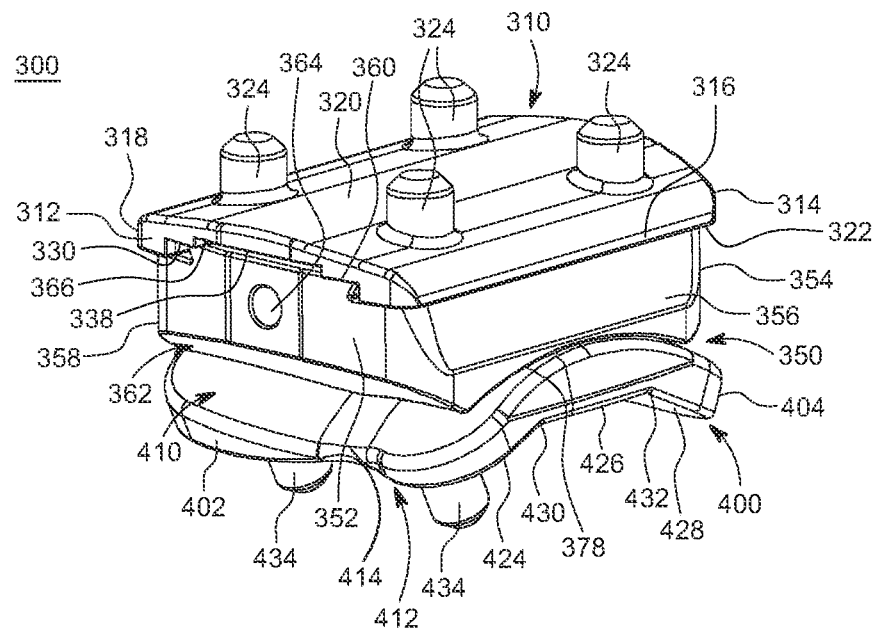
FIG. 18 is a first perspective view of an embodiment of an implant, in accordance with an aspect of the present disclosure.
Figure 19:
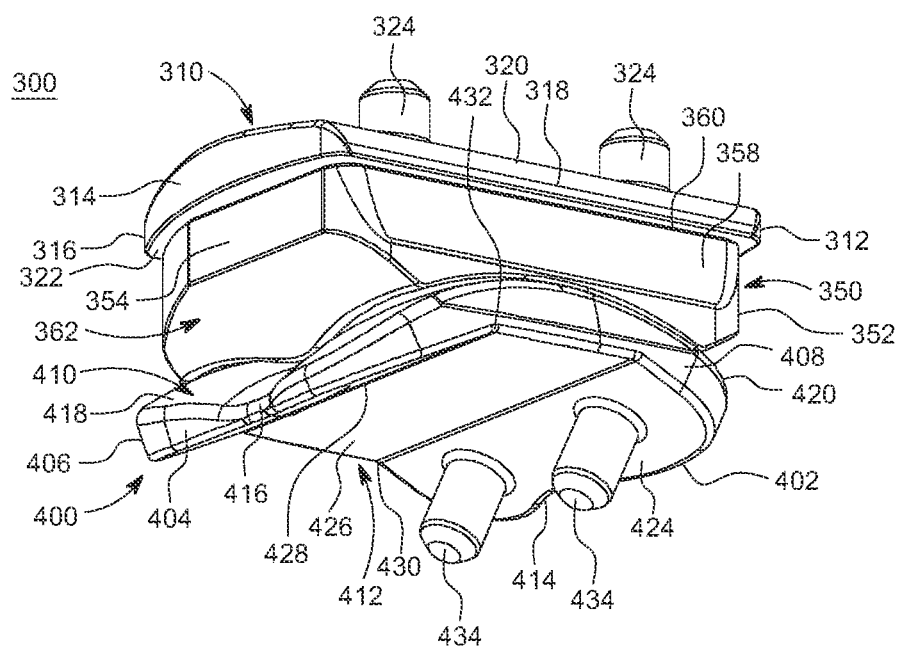
FIG. 19 is a second perspective view of the implant of FIG. 18, in accordance with an aspect of the present disclosure.

A method of inserting an implant 100 is shown in FIG. 17. The method may include, for example, obtaining an implant 250 and making an incision to expose a joint with a first bone and a second bone 252. The implant may be, for example, an implant 100 as described in greater detail above with reference to FIGS. 1-16 and which will not be described again here for brevity sake. The method may also include preparing the bones for receiving the implant 254. Next, the method may include coupling the first member to the first bone 256 and coupling the second member to the second bone 258. Then, the method may include inserting a second end of the insert into a first end of the first member 260. In addition, the method may include engaging a locking tab of the insert with a locking groove of the first member 262. In an embodiment, if the insert needs to be removed or replaced, for example, for a different size or due to wear or failure, an instrument may be inserted into the slot of the insert to release the locking tab of the insert from the locking groove of the first member 264. If the insert is removed, a second end of another insert may be inserted into a first end of the first member 260 and a locking tab of the new insert may be engaged with the locking groove of the first member 262. Finally, once the desired insert is installed, the method may include closing the incision 266.

Referring now to FIGS. 18-35, another implant 300 is shown. The implant 300 includes a first member or tibia base 310, an insert 350, and a second member, talus component, or articulating member 400. The insert 350 includes a top surface 360 and a bottom surface 362. The top surface 360 of the insert 350 couples to the first member 310 and the bottom surface 362 engages the second member 400.

Figure 32:
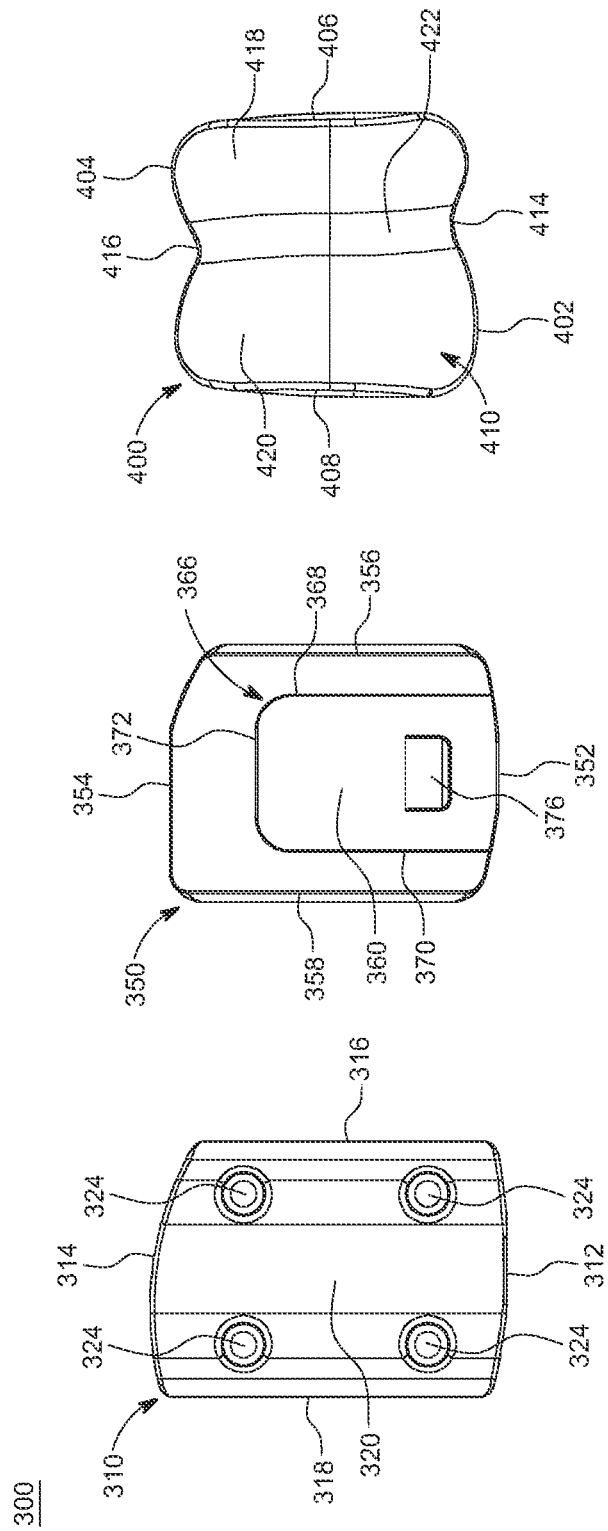
FIG. 32 is an exploded, top view of the implant of FIG. 18, in accordance with an aspect of the present disclosure.
Figure 33:
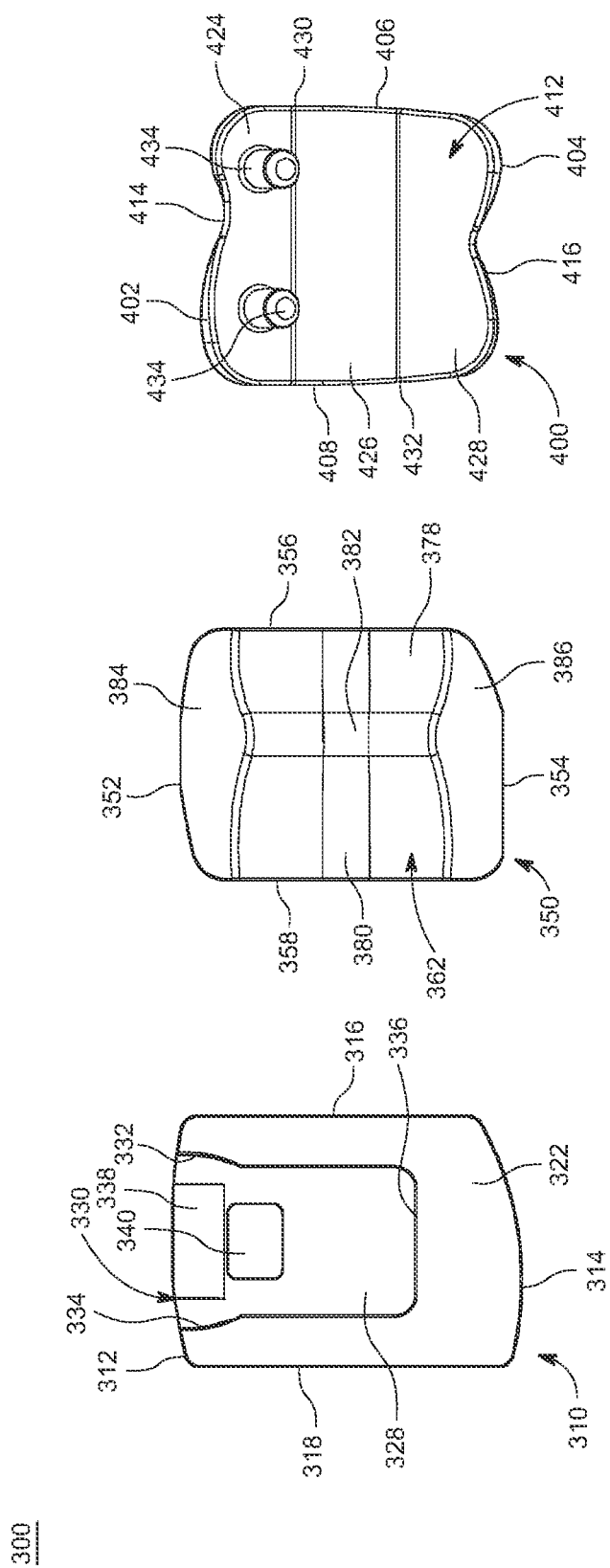
FIG. 33 is an exploded, bottom view of the implant of FIG. 18, in accordance with an aspect of the present disclosure.
Figure 34:
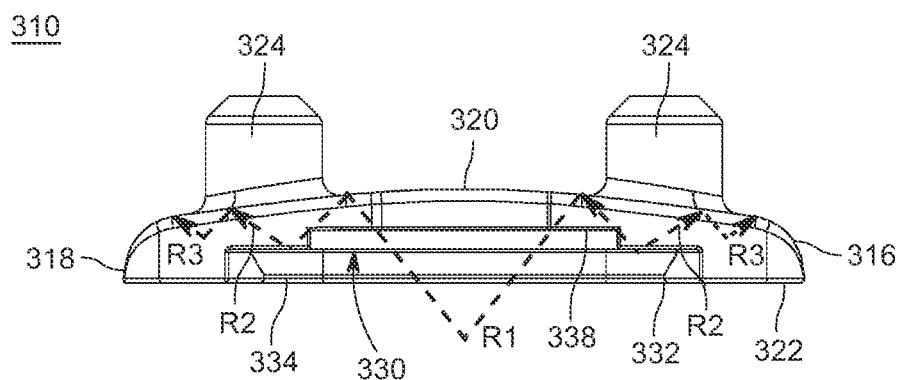
FIG. 34 is a first end view of a first member of the implant of FIG. 18, in accordance with an aspect of the present disclosure.

As shown in FIGS. 26-35, the first member 310 includes a first end or anterior end 312 opposite a second end or posterior end 314. The first member 310 also includes a first side or medial side 316 opposite a second side or lateral side 318. In addition, the first member 310 includes a top surface 320 opposite a bottom surface 322. The top surface 320 may include, for example, an arc shape or curvature extending between the first side 316 and the second side 318, as shown in FIGS. 24, 25, 28 and 29. The curvature may have, for example, multiple arc radii, such as, a first arc radius R1, a second arc radius R2, and a third arc radius R3, as shown in FIG. 34. The first arc radius R1 may be, for example, positioned near a middle portion of the top surface 320 of the first member 310. The second arc radii R2 may be, for example, positioned adjacent to the first arc radius R1 on both sides, such that a second arc radius R2 may be positioned adjacent to the first arc radius R1 on the first side 316 and a second arc radius R2 may be positioned adjacent to the first arc radius R1 on the second side 318. Finally, the third arc radii R3 may be, for example, positioned adjacent to one of the second arc radii R2 on each side of the first member 310, such that a third arc radius R3 is positioned between one of the second arc radii R2 and the first side 316 and a third arc radius R3 is positioned between the other second arc radius R2 and the second side 318. In one embodiment, the first arc radius R1 may be, for example, approximately 45 mm to 55 mm and more specifically, approximately 50 mm. The second arc radius R2 may be, for example, approximately 140 mm to 160 mm and more specifically approximately 150 mm. The third arc radius R3 may be, for example, approximately 190 mm to 210 mm and more specifically 200 mm. Although not shown, it is also contemplated that the top surface 320 of the first member 310 may be, for example, flat as the top surface 320 extends between the first side 316 and the second side 318. The top surface 320 of the first member 310 may also include, for example, sloped, tapered, or angled sides on the first side 316 and the second side 318 of the first member 310. The angle of the first and second sides 316, 318 as they extend away from the top surface 320 may be, for example, approximately 8° to 15° from vertical and more specifically approximately 10° from vertical. The edges of the first and second sides 316, 318 of the first member 310 may be, for example, rounded or curved.

Figure 35:
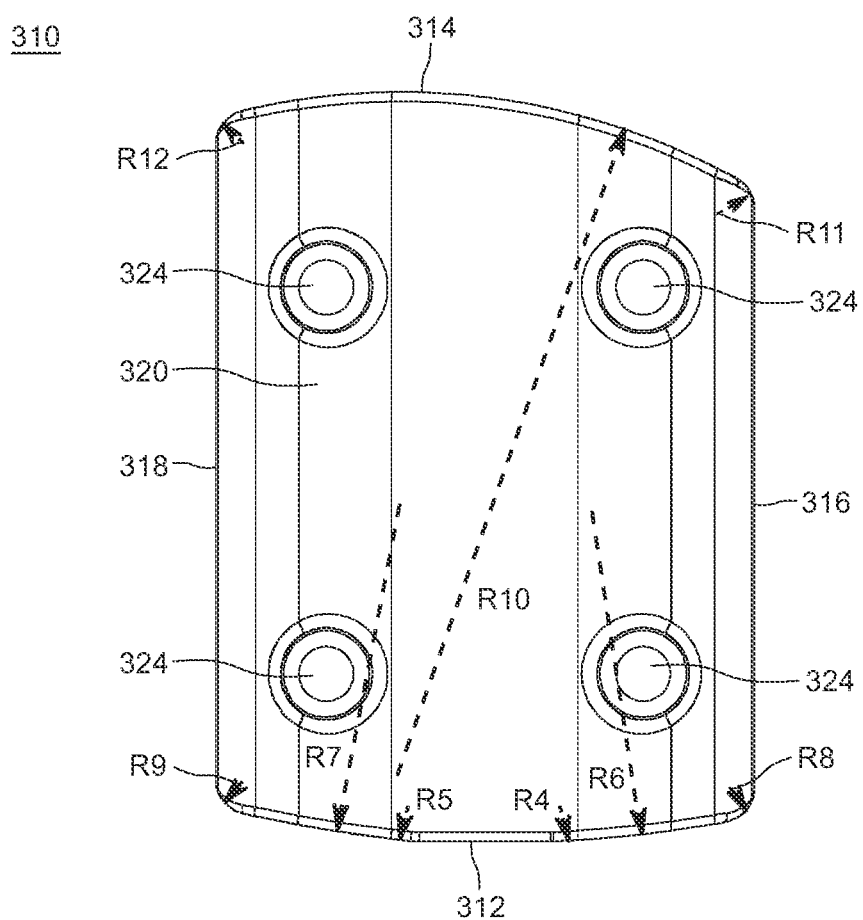
FIG. 35 is a top view of the first member of the implant of FIG. 18, in accordance with an aspect of the present disclosure.
Figure 36:
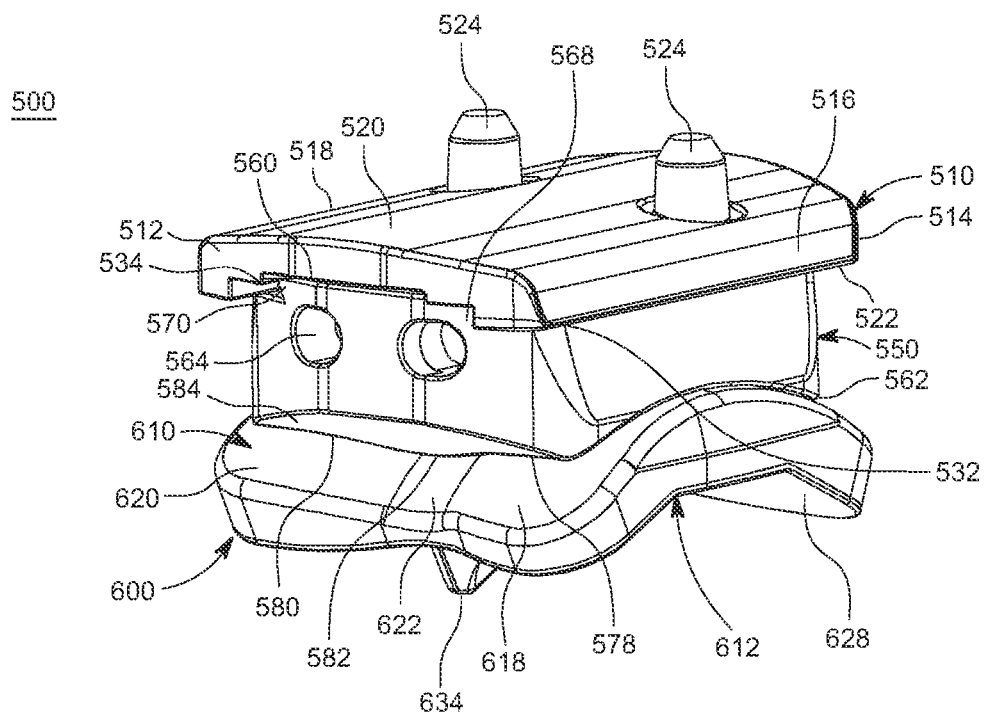
FIG. 36 is a first perspective view of an embodiment of an implant, in accordance with an aspect of the present disclosure.
Figure 37:
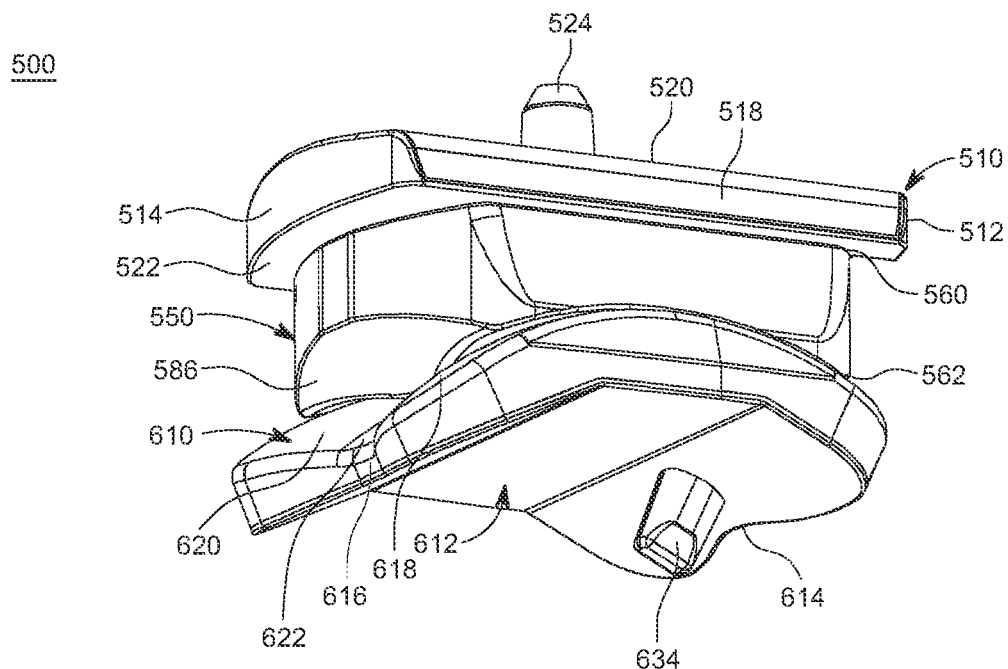
FIG. 37 is a second perspective view of the implant of FIG. 36, in accordance with an aspect of the present disclosure.

As shown in the top view of FIG. 35, the first and second ends 312, 314 may include, for example, multiple arc radii as the first and second ends 312, 314 extends between the first side 316 and the second side 318. The first end 312 may include multiple arc radii, for example, a fourth arc radius R4, a fifth arc radius R5, a sixth arc radius R6, a seventh arc radius R7, an eighth arc radius R8, and a ninth arc radius R9. The apex of the first end 312 may be, for example, offset medially from a longitudinal axis of the first member 310. The fourth arc radius R4 may be positioned to the right of the flat or planar surface of the first end 312 and the fifth arc radius R5 may be positioned to the left of the flat or planar surface of the first end 312. The fourth and fifth arc radii R4, R5 may be, for example, approximately 3 mm to 5 mm, and more preferably approximately 4 mm. The sixth arc radius R6 may be positioned adjacent to the fourth arc radius R4 toward the first side 316 of the first member 310. The seventh arc radius R7 may be positioned adjacent to the fifth arc radius R5 toward the second side 318 of the first member 310. The fifth and sixth arc radii R5, R6 may be, for example, approximately 60 mm to 75 mm, and more preferably approximately 67 mm. The eighth arc radius R8 may be positioned adjacent to the sixth arc radius R6 and the eighth arc radius R8 extends to the first side 316 of the first member 310. The ninth arc radius R9 may be positioned adjacent to the seventh arc radius R7 and the ninth arc radius R9 extends to the second side 318 of the first member 310. The eighth and ninth arc radii R8, R9 may be, for example, approximately 1 mm to 3 mm, and more preferably approximately 2 mm.

The second end 314 may also include multiple arc radii, for example, a tenth arc radius R10, an eleventh arc radius R11, and a twelfth arc radius R12. The apex of the second end 314 may be, for example, offset laterally from a longitudinal axis of the first member 310. The tenth arc radius R10 may be positioned in the central portion of the second end 314 of the first member 310. The tenth arc radius R10 may be, for example, approximately 30 mm to 45 mm, and more preferably approximately 37 mm. The eleventh arc radius R11 may be positioned adjacent to the tenth arc radius R10 and the eleventh arc radius R11 extends to the first side 316 of the first member 310. The twelfth arc radius R12 may be positioned adjacent to the tenth arc radius R10 and the twelfth arc radius R12 extends to the second side 318 of the first member 310. The eleventh and twelfth arc radii R11, R12 may be, for example, approximately 1 mm to 3 mm, and more preferably approximately 2 mm.

Figure 20:
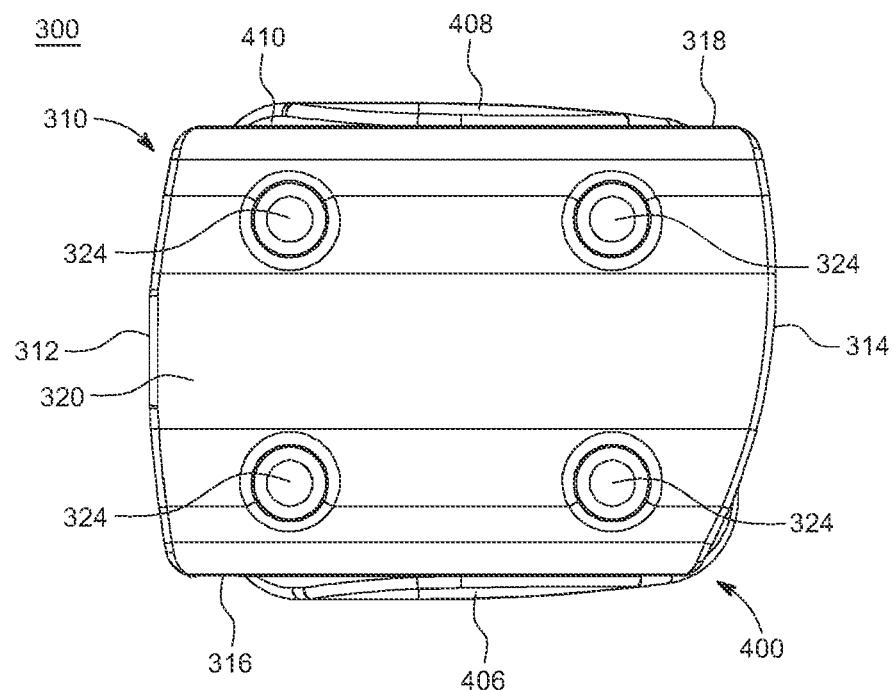
FIG. 20 is a top view of the implant of FIG. 18, in accordance with an aspect of the present disclosure.
Figure 21:
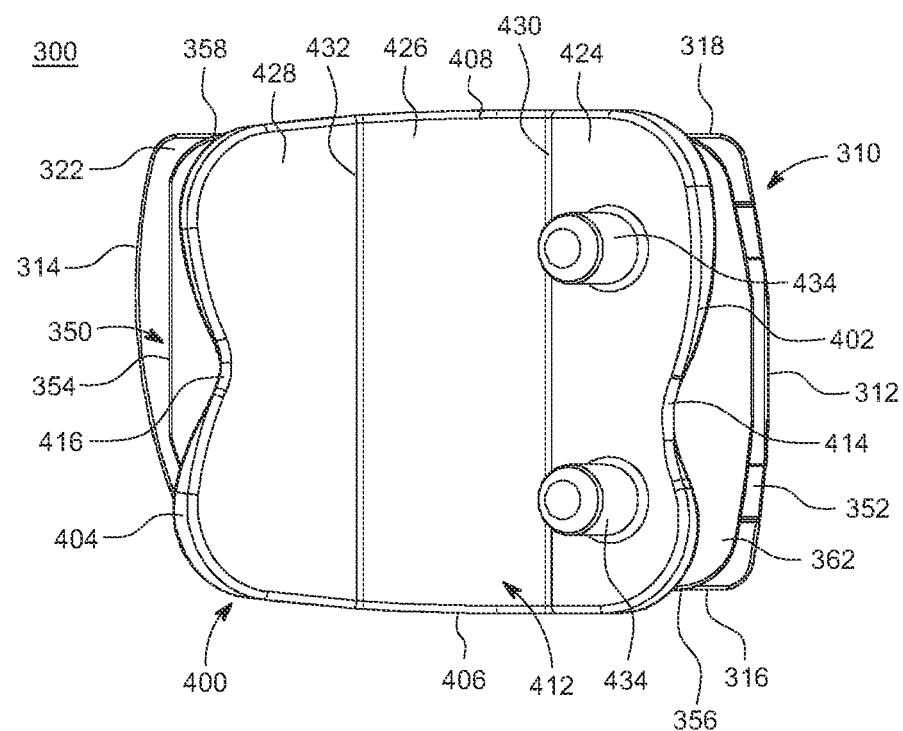
FIG. 21 is a bottom view of the implant of FIG. 18, in accordance with an aspect of the present disclosure.

The first member 310 may have an outer perimeter shape that may be, for example, a quadrilateral shape, such as, a generally trapezoidal from a top or bottom view, as shown in FIGS. 20, 32 and 33. The first and second sides 316, 318 may be generally parallel and the first end 312 and second end 314 may be, for example, angled or curved as they extend from the first side 316 to the second side 318. In an embodiment, the length of the first or medial side 316 may be, for example, shorter than the length of the second or lateral side 318. The angle or curvature of the first end 312 may be, for example, smaller than the angle of the second end 314. The top surface 320, first side 316 and second side 318 may be, for example, textured or coated to provide a friction-stabilization surface and to allow for bone on-growth. The textured surface may be, for example, plasma sprayed biocompatible material, such as, commercially-pure titanium, or another biocompatible material as known by one of ordinary skill in the art.

With continued reference to FIGS. 26-33, the top surface 320 of the first member 310 includes at least one peg or vertical peg 324 extending away from the top surface 320. The at least one peg 324 may be, for example, four pegs 324, although alternative numbers of pegs 324 are also contemplated. The pegs 324 may be, for example, positioned equally spaced around the top surface 320 forming, for example, the four points or corners of a quadrilateral, such as a square, rectangle, or diamond shape or alternatively, the four pegs 324 may be randomly positioned on the top surface 320. The at least one peg 324 may not be, for example, textured, rather the at least one peg 324 may be smooth to decrease bone resorption at the resection level.

Figure 27:
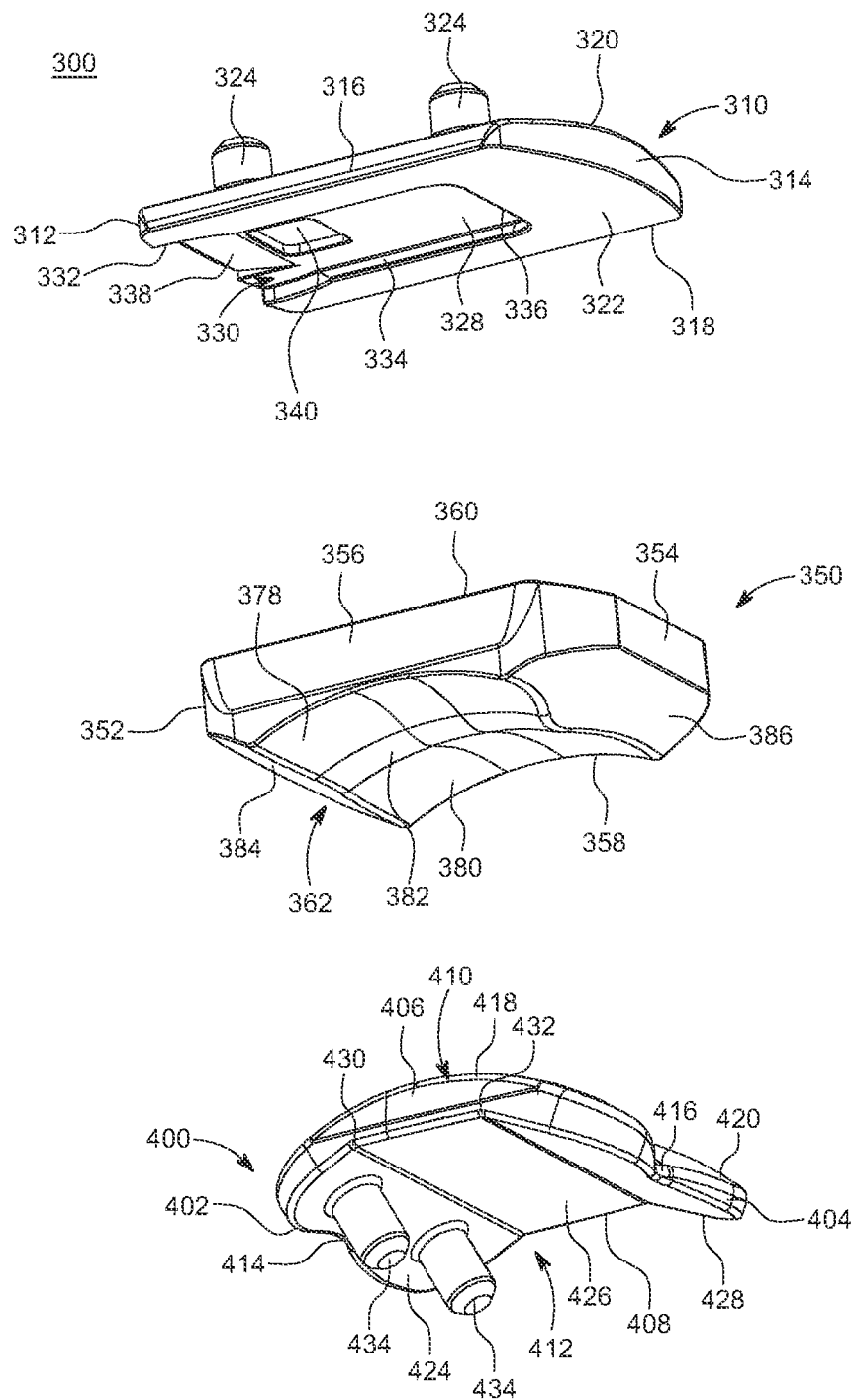
FIG. 27 is a second exploded, perspective view of the implant of FIG. 18, in accordance with an aspect of the present disclosure.

Referring now to FIGS. 27 and 33, the bottom surface 322 of the first member 310 is shown. The bottom surface 322 includes a recessed region or engagement region 328 extending into the first member 310 from the bottom surface 322 toward the top surface 320. The first member 310 may come in multiple sizes for use with patients having different size tibia bones and the recessed region 328 of each of the first members 310 will be, for example, sized and shaped the same to allow for replacement of the first member 310, as needed. The bottom surface 322 also includes an engagement channel 330 extending from the first end 312 into the recessed region 328. In addition, the bottom surface 322 of the first member 310 includes a first engagement feature or first female dovetail portion 332 extending from the first side 316 into the recessed region 328, a second engagement feature or second female dovetail portion 334 extending from the second side 318 into the recessed region 328, and a third engagement feature or third female dovetail portion 336 extending from a position near the second end 314 into the recessed region 328. The bottom surface 322 of the first member 310 also includes a slot or removal engagement feature 338 and a locking groove 340 positioned adjacent to the slot 338. The slot 338 may be, for example, angled as the slot 338 extends from the first end 312 toward the locking groove 340.

Figure 22:
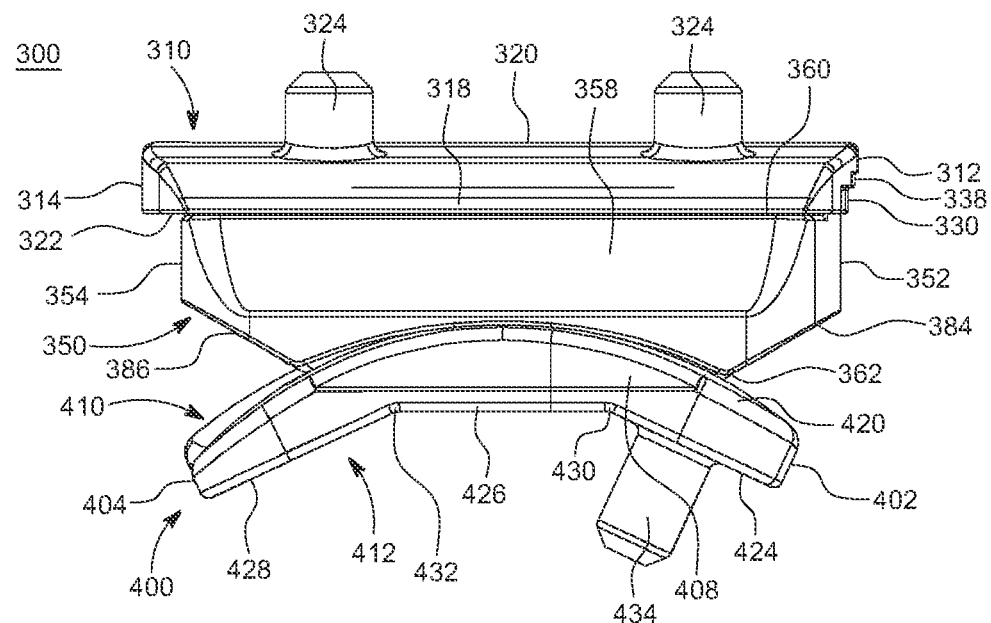
FIG. 22 is a first side view of the implant of FIG. 18, in accordance with an aspect of the present disclosure.
Figure 23:
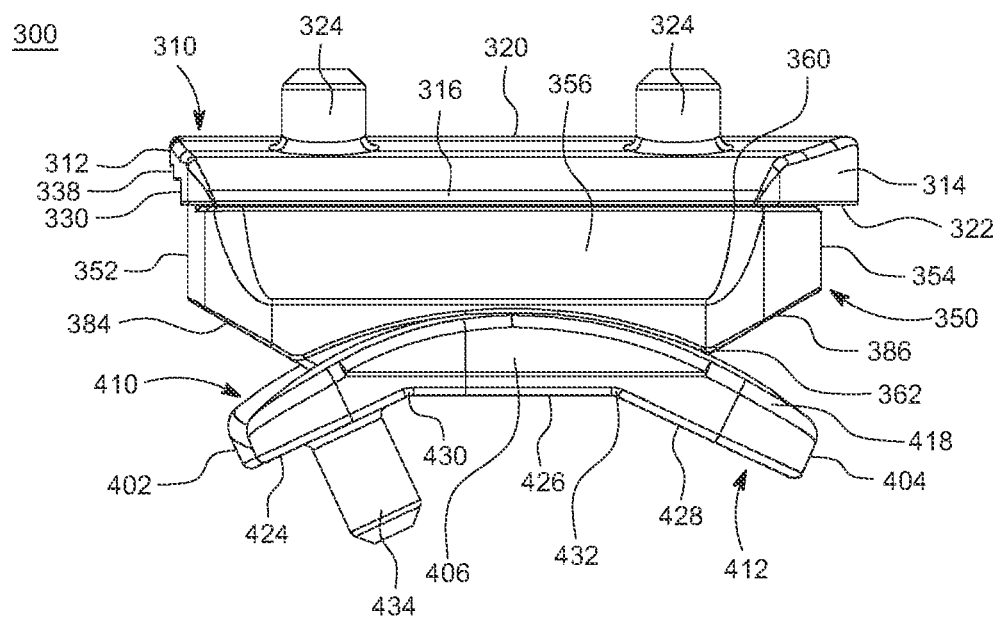
FIG. 23 is a second side view of the implant of FIG. 18, in accordance with an aspect of the present disclosure.
Figure 24:
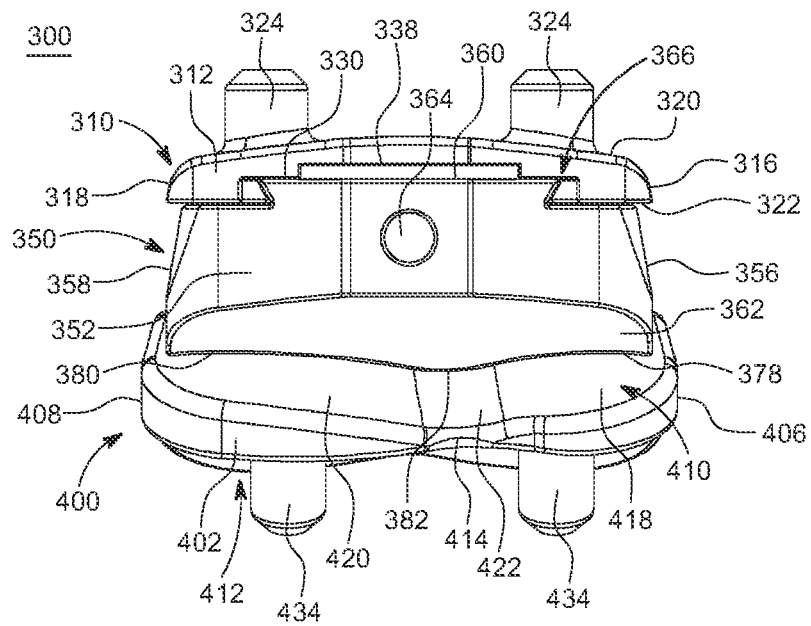
FIG. 24 is a first end view of the implant of FIG. 18, in accordance with an aspect of the present disclosure.
Figure 25:
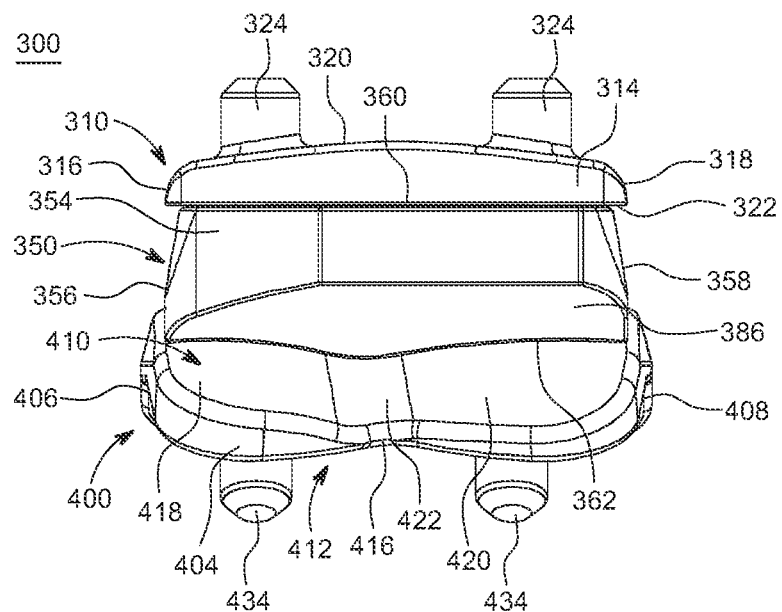
FIG. 25 is a second end view of the implant of FIG. 18, in accordance with an aspect of the present disclosure.
Figure 26:
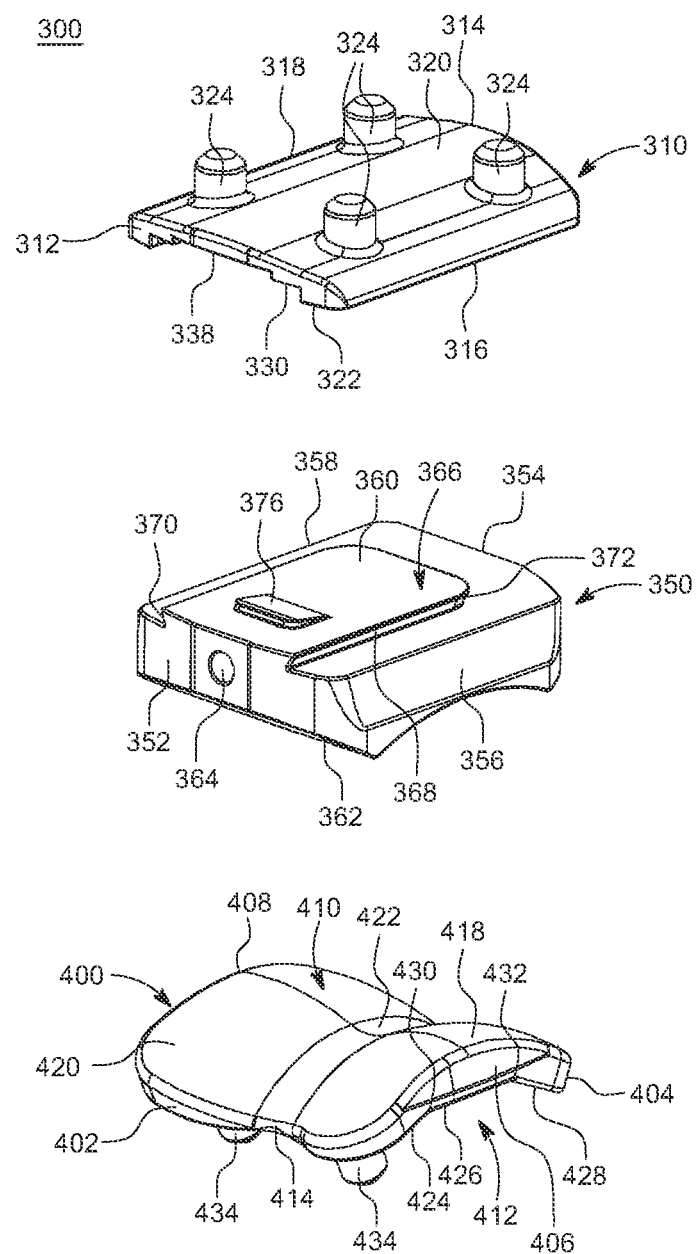
FIG. 26 is a first exploded, perspective view of the implant of FIG. 18, in accordance with an aspect of the present disclosure.

Referring now to FIGS. 18-33, the second member, talus component or articulating member 400 has a first end or anterior end 402 opposite a second end or posterior end 404. The second member 400 also has a first side or medial side 406 opposite a second side or lateral side 408. In addition, the second member 400 has a top surface or articulating surface 410 opposite a bottom surface or bone engagement surface 412. The second member 400 may have, for example, a trapezium shape, as shown in FIGS. 32 and 33. The first side 406 and second side 408 may be angled as they extend from the top surface 410 to the bottom surface 412 and the angle may be, for example, approximately 15° to 20° and more preferably approximately 10°. The first side 406 may be, for example, shorter than the second side 408. As shown in FIGS. 22, 23, and 25, at least a portion of the first and second sides 406, 408 may be, for example, angled or tapered from the top surface 410 toward the bottom surface 412. The second member 400 includes an anterior recess 414 extending into the first end 402. The anterior recess 414 may be, for example, positioned near a midpoint of a lateral axis of the second member 400 or, alternatively may be medially biased. The second member 400 also includes a posterior recess 416 extending into the second end 404. The posterior recess 416 may be, for example, positioned near a midpoint of the lateral axis of the second member 400 or, alternatively may be medially biased.

As shown in FIGS. 26 and 28-32, the top surface 410 of the second member 400 includes a medial articulating surface 418 extending from the first side 406 of the second member 400 toward the second side 408. The top surface 410 may also include a lateral articulating surface 420 extending from the second side 408 of the second member 400 toward the first side 406. In addition, the top surface 410 also includes a central articulating portion 422 positioned at a point where the medial articulating surface 418 contacts the lateral articulating surface 420.

The medial articulating surface 418 may include at least one first curvature along a longitudinal axis and at least one second curvature perpendicular to the longitudinal axis, as shown in FIG. 31. The lateral articulating surface 420 has at least one third curvature along the longitudinal axis and at least one fourth curvature perpendicular to the longitudinal axis. In addition, the central articulating portion 422 may have a concave curvature on the top surface 410 of the second member 400 and the medial and lateral articulating surfaces 418, 420 may have convex curvatures on the top surface 410 of the second member 400. The articulating surface 410 of the second member 400 may include, for example, at least one coronal radii and the at least one coronal radii may have, for example, a range of approximately 12 mm to 26 mm for a size 1 second member 400, a range of approximately 14 mm to 30 mm for a size 3 second member 200, and a range of approximately 17 mm to 34 mm for a size 5 second member 200. The articulating surface 410 of the second member 400 may include, for example, at least one sagittal radii and the at least one sagittal radii may have, for example, a range of approximately 18 mm to 25 mm for a size 1 second member 400, a range of approximately 20 mm to 28 mm for a size 3 second member 200, and a range of approximately 21 mm to 30 mm for a size 5 second member 200. In an embodiment, the anterior portion of the second member 400 may include a first sagittal radius of the lateral articulating surface 420 and a second sagittal radius of the medial articulating surface 418. The first sagittal radius may be, for example, larger than the second sagittal radius. In addition, the posterior portion of the second member 400 may include a third sagittal radius of the lateral articulating surface 420 and a fourth sagittal radius of the medial articulating surface 418. The third sagittal radius may be, for example, smaller than the fourth sagittal radius. A larger anterior lateral sagittal radius than anterior medial sagittal radius and a smaller posterior lateral sagittal radius than posterior medial sagittal radius allow for the joint axis of rotation to point distally and laterally during dorsiflexion and distally and medially during plantarflexion.

Referring now to FIGS. 19, 21-23, 27, 30, 31, and 33, the bottom surface 412 of the second member 400 may include a first portion 424, a second portion 426, and a third portion 428. The first portion 424, the second portion 426, and the third portion 428 may each have, for example, planar surfaces. The second portion 426 may be positioned between the first portion 424 and the third portion 428. The first portion 424 may extend, for example, from the first end 402 to a first transition point 430. The second portion 426 may extend, for example, from the first transition point 430 to a second transition point 432. The third portion 428 may extend, for example, from the second transition point 432 to the second end 404. The first portion 424 may extend away from the second portion 426 at a first angle and the third portion 428 may extend away from the second portion 426 at a second angle. The first angle may be, for example, approximately 25° to 35°, and the second angle may be, for example, approximately 25° to 35°. The bottom surface 412 of the second member 400 may be, for example, coated or textured with a biocompatible material. The texture or coating may be, for example, a plasma sprayed material, such as, a commercially-pure titanium or other biocompatible material, as known by one of ordinary skill in the art.

The bottom surface 412 of the second member 400 may also include at least one stem or peg 434 extending away from the first portion 424 of the bottom surface 412, as shown in FIGS. 18, 19, 21-31 and 33. The at least one stem 434 may be, for example, two stems 434, although other numbers of stems 434 are also contemplated. As depicted, the first stem 434 is positioned on the first portion 424 between the anterior recess 414 and the first side 406 and the second stem 434 is positioned on the first portion 424 between the anterior recess 414 and the second side 408, as shown in FIGS. 27 and 33. The stems 434 may be, for example, positioned slightly medially biased and may be offset, for example, approximately 1 mm from a midpoint of the second member 400. The at least one stem 434 may not be, for example, textured or coated, rather the at least one stem 434 may be smooth to decrease bone resorption at the resection level. The at least one stem 434 may have, for example, a cylindrical, pyramidal, or other quadrilateral prism shape.

Referring to FIGS. 18-33, the insert, bearing insert, polyethylene insert, or articulating insert 350 is shown. The insert 350 includes a first end or anterior end 352 opposite a second end or posterior end 354. The insert 350 also includes a first side or medial side 356 opposite a second side or lateral side 358. In addition, the insert 350 includes a top surface 360 opposite a bottom surface 362. The first end 352 of the insert 350 includes an opening or cylinder 364 extending into the insert 350 from the first end 352 toward the second end 354. The opening 364 may be sized and shaped or configured to receive an instrument or member, for example, a self-tapping screw to engage the insert 350 and remove the insert 350 from the first member 310. The first and second sides 356, 358 may be, for example, angled or tapered along at least a portion of the sides 356, 358 as the sides 356, 358 extend from the top surface 360 toward the bottom surface 362, as shown in FIGS. 24, 25, 28 and 29.

With continued reference to FIGS. 26 and 28-32, the top surface 360 of the insert 350 includes an engagement member or protrusion 366. The engagement member 366 includes a first engagement feature or first male dovetail 368 near the first side 356, a second engagement feature or second male dovetail 370 near the second side 358, and a third engagement feature or third male dovetail 372 near the second end 354. When the insert 350 is coupled to the first member 310, the first engagement feature 368 of the insert 350 may be configured or sized and shaped to engage the first engagement feature 332 of the first member 310, the second engagement feature 370 of the insert 350 may be configured or sized and shaped to engage the second engagement feature 334 of the first member 310, and the third engagement feature 372 of the insert 350 may be configured or sized and shaped to engage the third engagement feature 336 of the first member 310. The top surface 360 also includes a locking tab or protrusion 376. The locking tab 376 may, for example, extend away from the top surface 360 of the insert 350. The locking tab 376 may form, for example, a ramped portion extending from the top surface 360 of the insert 350 on the side positioned toward the second end 354 to a side positioned toward the first end 352. The side of the locking tab 376 positioned toward the first end 352 may have a height taller than the height of the side of the locking tab 376 positioned toward the second end 354. The locking tab 376 may be configured or sized and shaped to engage the locking groove 340 of the bottom surface 322 of the first member 310.

Referring now to FIGS. 27-31 and 33, the bottom surface 362 of the insert 350 includes a first contact surface or medial contact surface 378, a second contact surface or lateral contact surface 380, and a central contact surface 382. The first contact surface 378 extends along at least a portion of the bottom surface 362 in a medial-lateral direction from the first side 356 toward the second side 358. The first contact surface 378 also extends along at least a portion of the bottom surface 362 in an anterior-posterior direction from a position near the first end 352 toward a position near the second end 354. The second contact surface 380 extends along at least a portion of the bottom surface 362 from the second side 358 toward the first side 356. The second contact surface 380 also extends along at least a portion of the bottom surface 362 in an anterior-posterior direction from a position near the first end 352 toward a position near the second end 354. The central contact surface or central sulcus 382 is positioned between the first contact surface 378 and the second contact surface 380. The central contact surface 382 also extends along at least a portion of the bottom surface 362 in an anterior-posterior direction from a position near the first end 352 toward a position near the second end 354. The first and second contact surfaces 378, 380 form a bi-condylar surface, as shown in FIGS. 24, 25, and 27-29. The centers of the radii of the bi-condylar surface may be, for example, spaced between approximately 18 mm and 26 mm for all sizes of the insert 350. More specifically, the centers of radii of the bi-condylar surface may be, for example, approximately 20 mm for a size 1 insert 350, approximately 22 mm for a size 3 insert 350, and approximately 24 mm for a size 5 insert 350.

With continued reference to FIGS. 27-31 and 33, the first contact surface 378 includes at least one first curvature along a longitudinal axis and at least one second curvature along a lateral axis. The second contact surface 380 includes at least one third curvature along a longitudinal axis and at least one fourth curvature along a lateral axis. The central contact surface 382 includes at least one curvature. The curvatures of the first and second contact surfaces 378, 380 may be, for example, concave curvatures and the at least one curvature of the central contact surface 382 may be, for example, a convex curvature. The central contact surface 382 may provide, for example, stability in a medial-lateral direction. The central contact surface 382 may have, for example, a height ranging from approximately 1.5 mm and 2 mm. The insert 350 may also have a coronal radii and the coronal radii may be, for example, approximately 1.10 times the coronal radii of the talus. In addition, the insert 350 may have at least one sagittal radii. The at least one sagittal radii of the insert 350 may be, for example, multiple tangent and/or continuous radii, which may include varying levels of conformity with the sagittal radii of the second member 400. The sagittal radii may have, for example, a range of approximately 25 mm to 34 mm for all sizes of the insert 350. More specifically, the sagittal radii may be, for example, approximately 25 mm to 26 mm for the size 1 insert 350 and approximately 33 mm to 34 mm for the size 5 insert 350.

Referring now to FIGS. 19, 21-25, 27-31 and 33, the bottom surface 362 may also include, for example, a first angled or tapered portion 384 and a second angled or tapered portion 386. The first angled portion 384 may be, for example, positioned to extend from the first end 352 to the anterior portion of the contact surfaces 378, 380, 382 of the bottom surface 362 of the insert 350. The second angled portion 386 may be, for example, positioned to extend from the second end 354 to the posterior portion of the contact surfaces 378, 380, 382 of the bottom surface 362 of the insert 350.

As shown in FIGS. 18-25, when assembled and/or implanted, the top surface 360 of the insert 350 couples to a bottom surface 322 of the first member 310. In addition, the top surface 410 of the second member 400 is configured or sized and shaped to articulate with the bottom surface 362 of the insert 350. Specifically, the medial articulating surface 418 of the second member 400 is configured to articulate with the first contact surface 378 of the insert 350, the lateral articulating surface 420 of the second member 400 is configured to articulate with the second contact surface 380 of the insert 350, and the central portion 422 of the second member 400 is configured to articulate with the third contact surface 382 of the insert 350.

Referring now to FIGS. 36-51, another implant 500 is shown. The implant 500 includes a first member or tibia base 510, an insert 550, and a second member, talus component, or articulating member 600. The insert 550 includes a top surface 560 and a bottom surface 562. The top surface 560 of the insert 550 couples to the first member 510 and the bottom surface 562 engages the second member 600.

As shown in FIGS. 44-51, the first member 510 includes a first end or anterior end 512 opposite a second end or posterior end 514. The first member 510 also includes a first side or medial side 516 opposite a second side or lateral side 518. In addition, the first member 510 includes a top surface 520 opposite a bottom surface 522. The top surface 520 may include, for example, an arc shape or curvature extending between the first side 516 and the second side 518, as shown in FIGS. 42, 43, 46 and 47. The curvature may have, for example, multiple arc radii, which in an embodiment may be the same or similar to the arc radii described with reference to FIG. 34 in greater detail above and in other embodiments the multiple arc radii may be different than described above with reference to FIG. 34. The top surface 520 of the first member 510 may also include, for example, sloped, tapered, or angled sides on the first side 516 and the second side 518 of the first member 510. The angle of the first and second sides 516, 518 as they extend away from the top surface 520 may be, for example, approximately 8° to 15° from vertical and more specifically approximately 10° from vertical. The edges of the first and second sides 516, 518 of the first member 510 may be, for example, rounded or curved.

As shown in the top view of FIG. 50, the first and second ends 512, 514 may include, for example, multiple arc radii as the first and second ends 512, 514 extend between the first side 516 and the second side 518. In an embodiment, the multiple arc radii of the first member 510 may be as described in greater detail above with reference to FIG. 35, which will not be described again here for brevity sake. In other embodiments the multiple arc radii may be different as described with respect to FIG. 35.

Figure 52:
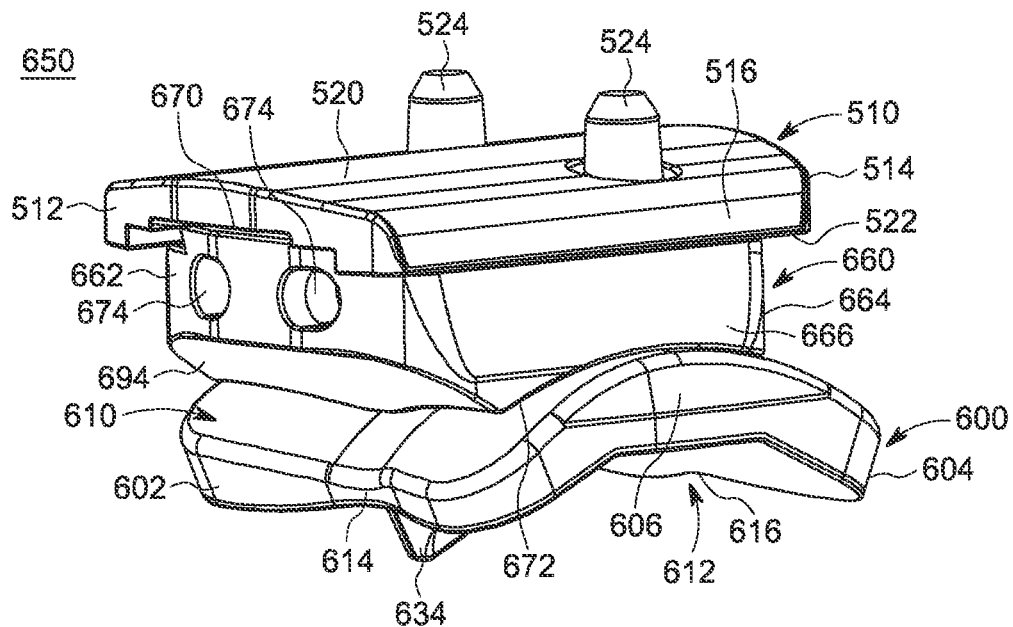
FIG. 52 is a first perspective view of an implant, in accordance with an aspect of the present disclosure.
Figure 53:
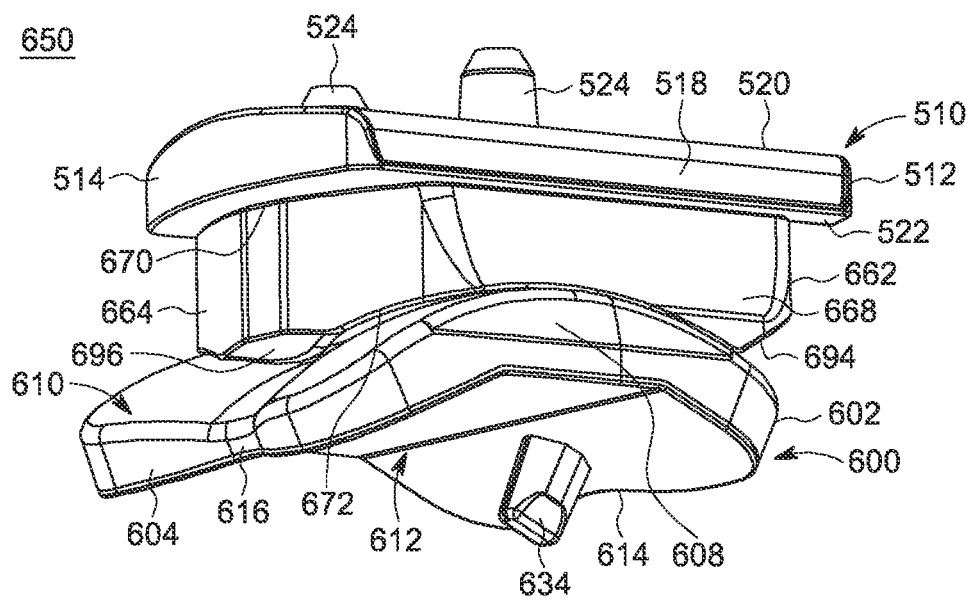
FIG. 53 is a second perspective view of the implant of FIG. 52, in accordance with an aspect of the present disclosure.

The first member 510 may have an outer perimeter shape that may be, for example, a quadrilateral shape, such as, a generally trapezoidal from a top or bottom view, as shown in FIGS. 38, 51 and 52. The first and second sides 516, 518 may be generally parallel and the first end 512 and second end 514 may be, for example, angled or curved as they extend from the first side 516 to the second side 518. In an embodiment, the length of the first or medial side 516 may be, for example, shorter than the length of the second or lateral side 518. The angle or curvature of the first end 512 may be, for example, smaller than the angle of the second end 514. The top surface 520, first side 516 and second side 518 may be, for example, textured or coated to provide a friction-stabilization surface and to allow for bone ongrowth. The textured surface may be, for example, plasma sprayed biocompatible material, such as, commercially-pure titanium, or another biocompatible material as known by one of ordinary skill in the art.

With continued reference to FIGS. 44-51, the top surface 520 of the first member 510 includes at least one peg or vertical peg 524 extending away from the top surface 520. The at least one peg 524 may be, for example, two pegs 524, although alternative numbers of pegs 524 are also contemplated. The pegs 524 may be, for example, positioned equally spaced apart on the top surface 520 or alternatively, the two pegs 524 may be randomly positioned on the top surface 520. The at least one peg 524 may not be, for example, textured, rather the at least one peg 524 may be smooth to decrease bone resorption at the resection level.

Figures 44, 45:
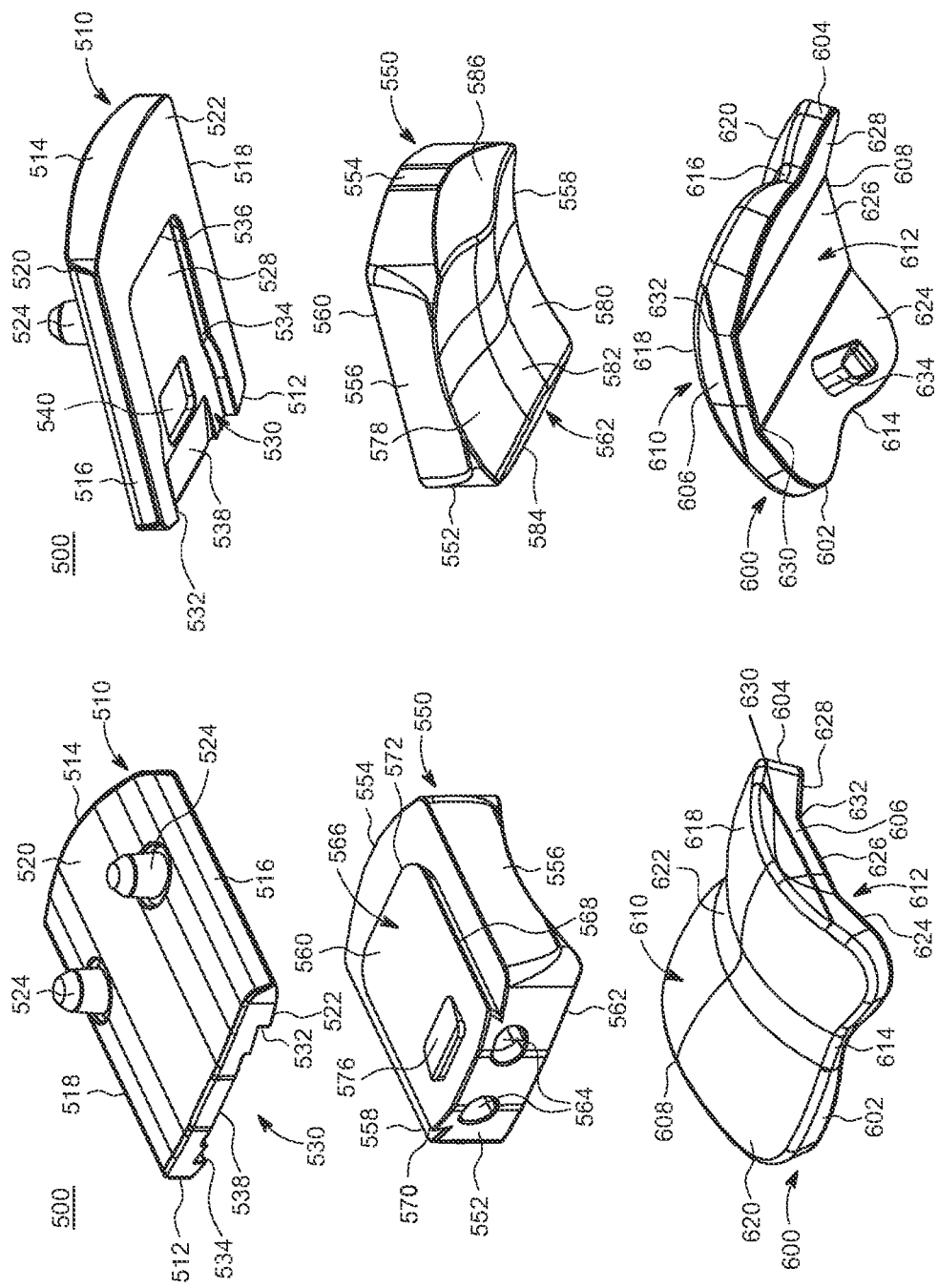
FIG. 44 is a first exploded, perspective view of the implant of FIG. 36, in accordance with an aspect of the present disclosure.
FIG. 45 is a second exploded, perspective view of the implant FIG. 36, in accordance with an aspect of the present disclosure.

Referring now to FIGS. 45 and 51, the bottom surface 522 of the first member 510 is shown. The bottom surface 522 includes a recessed region or engagement region 528 extending into the first member 510 from the bottom surface 522 toward the top surface 520. The first member 510 may come in multiple sizes for use with patients having different size tibia bones and the recessed region 528 of each of the first members 510 will be, for example, sized and shaped the same to allow for replacement of the first member 510, as needed. The bottom surface 522 also includes an engagement channel 530 extending from the first end 512 into the recessed region 528. In addition, the bottom surface 522 of the first member 510 includes a first engagement feature or first female dovetail portion 532 extending from the first side 516 into the recessed region 528, a second engagement feature or second female dovetail portion 534 extending from the second side 518 into the recessed region 528, and a third engagement feature or third female dovetail portion 536 extending from a position near the second end 514 into the recessed region 528. The bottom surface 522 of the first member 510 also includes a slot or removal engagement feature 538 and a locking groove 540 positioned adjacent to the slot 538. The slot 538 may be, for example, angled as the slot 538 extends from the first end 512 toward the locking groove 540. As shown in FIG. 51, the engagement channel 530 may have a first width at the opening at the first end 512 and a second width at the closed end near the second end 514. The first width may be, for example, wider than the second width. At least a portion of the first engagement feature 532 and at least a portion of the second engagement feature 534 may be, for example, tapered or curved between the first width at the opening of the first end 512 and the second width. The second width may extend from a position adjacent to the locking groove 540 to the closed end of the engagement channel 530.

Figure 123:
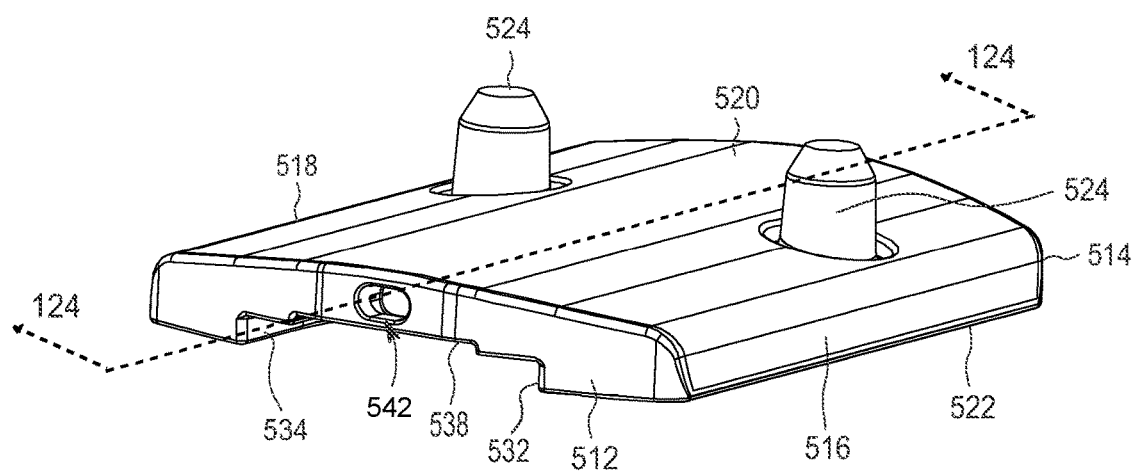
Figure 124:
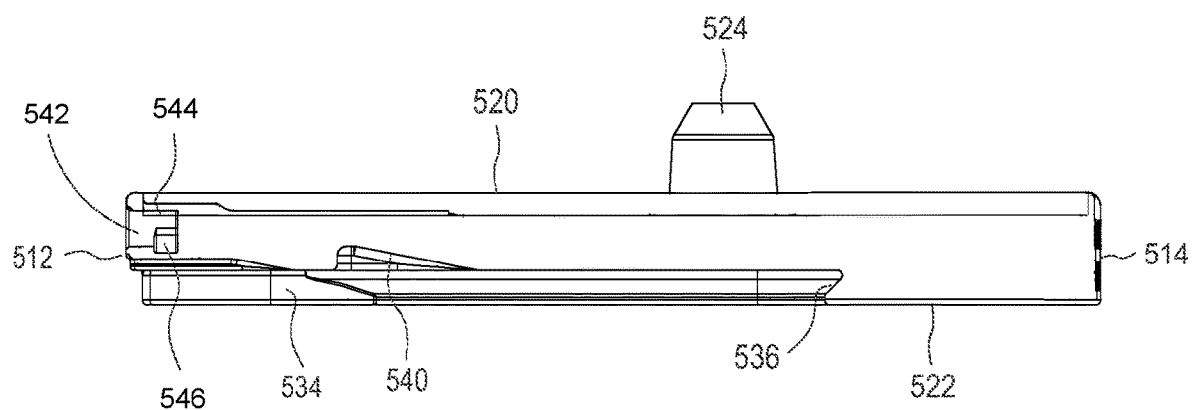

Referring now to FIGS. 123-124, another embodiment of the first member 510 is shown. The first member 510 of FIGS. 123-124 is the same or similar to the first member 510 shown in FIGS. 36-51 with the addition of an opening 542. The opening 542 may be, for example, positioned on the first end 512 of the first member 510. The opening 542 may extend from the first end 512 into the implant 510 toward the second end 514. The opening 542 may have, for example, an oval, rectangular, or like shape where the height of the opening 542 is smaller than the length. The height may, for example, extend between the top surface 520 and the bottom surface 522. The length may, for example, extend between the first side 516 and the second side 518. The opening 542 may include, for example, a first recess or groove 544 and a second recess or groove 546. The first recess 544 may be, for example, inset into a top surface of the opening 542. The first recess 544 may extend, for example, from the interior of the opening 542 toward the top surface 520 of the first member 510. The first recess 544 may be positioned, for example, on the top surface of the opening 542. The second recess 546 may be, for example, inset into a bottom surface of the opening 542. The second recess 546 may extend, for example, from the interior of the opening 542 toward the bottom surface 522 of the first member 510. The second recess 546 may be positioned, for example, on the bottom surface and a portion of each side surface of the opening 542, as shown in FIG. 124. In an embodiment, the second recess 546 may, for example, extend around a larger portion of the interior surface of the opening 542 than the first recess 544. At least one of the opening 542, first recess 544, and the second recess 546 may be configured to engage an insertion tool to, for example, assist with inserting the first member 510 into a patient or assist with positioning the first member 510 during insertion of other components of the implant 500.

Figure 40:
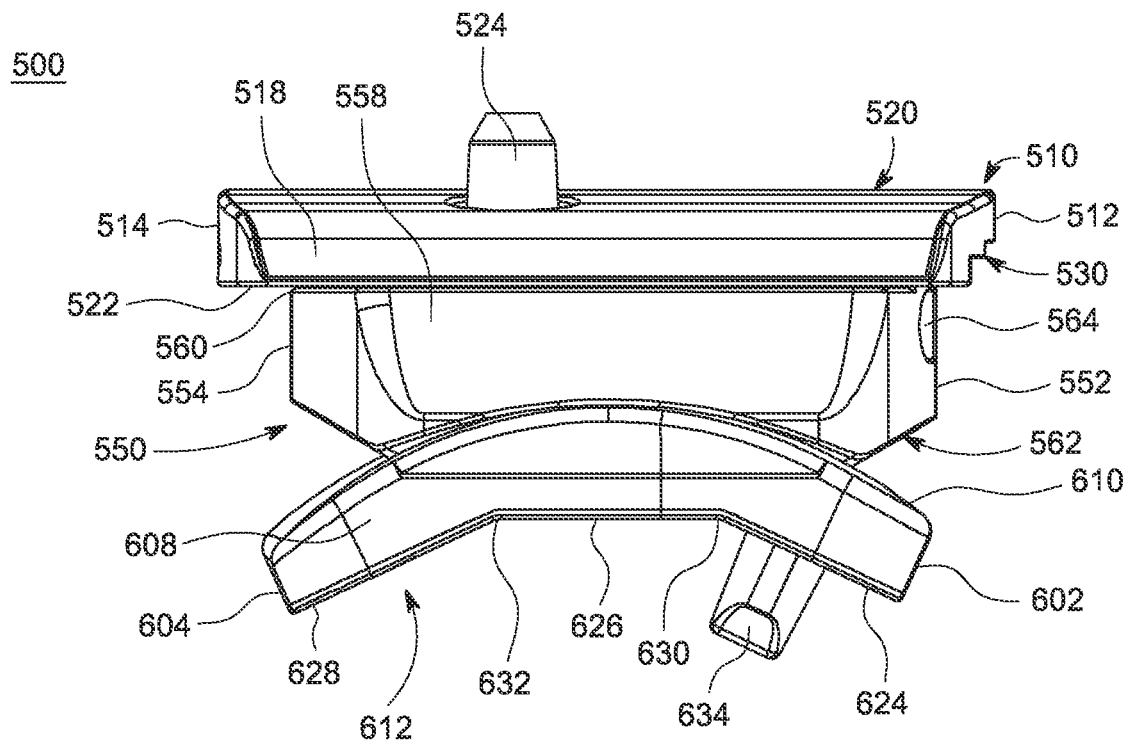
FIG. 40 is a first side view of the implant of the of FIG. 36, in accordance with an aspect of the present disclosure.
Figure 41:
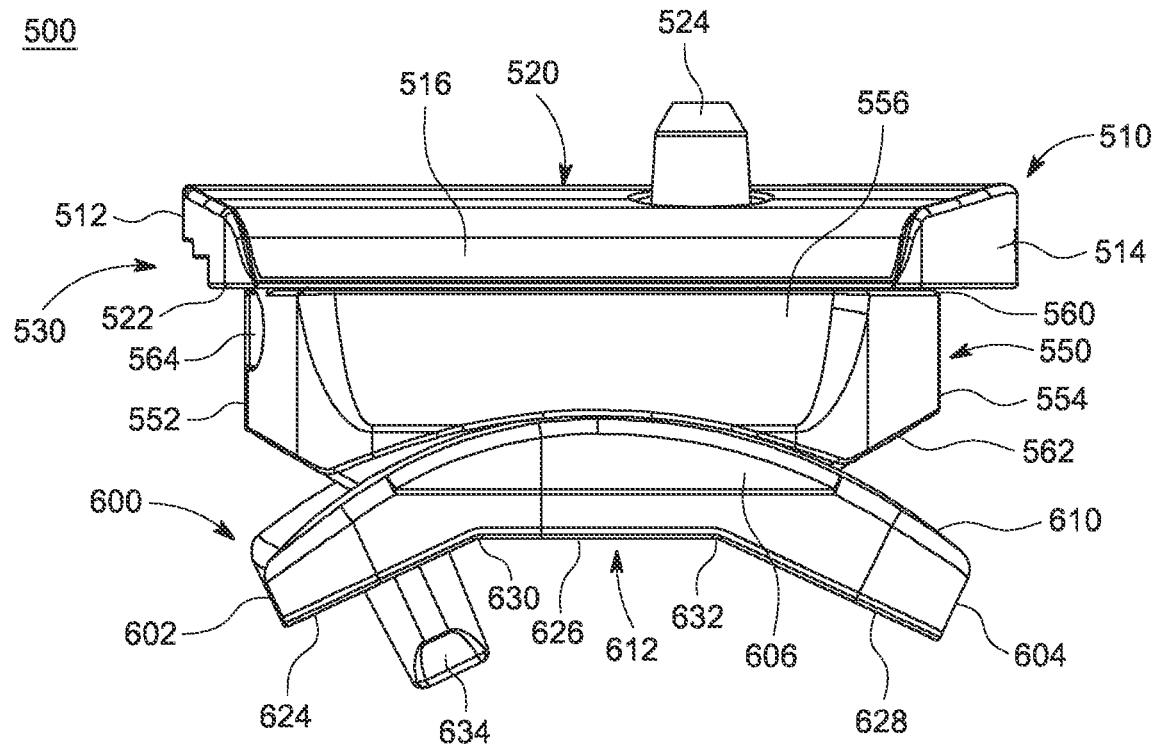
FIG. 41 is a second side view of the implant of FIG. 36, in accordance with an aspect of the present disclosure.
Figure 42:
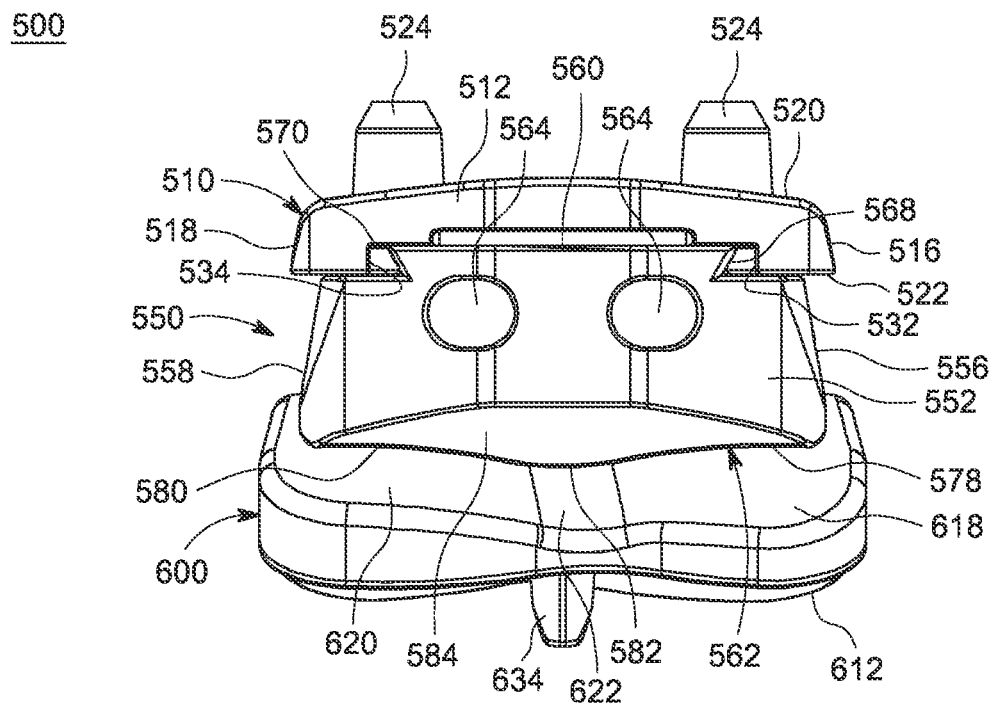
FIG. 42 is a first end view of the implant of FIG. 36, in accordance with an aspect of the present disclosure.
Figure 43:
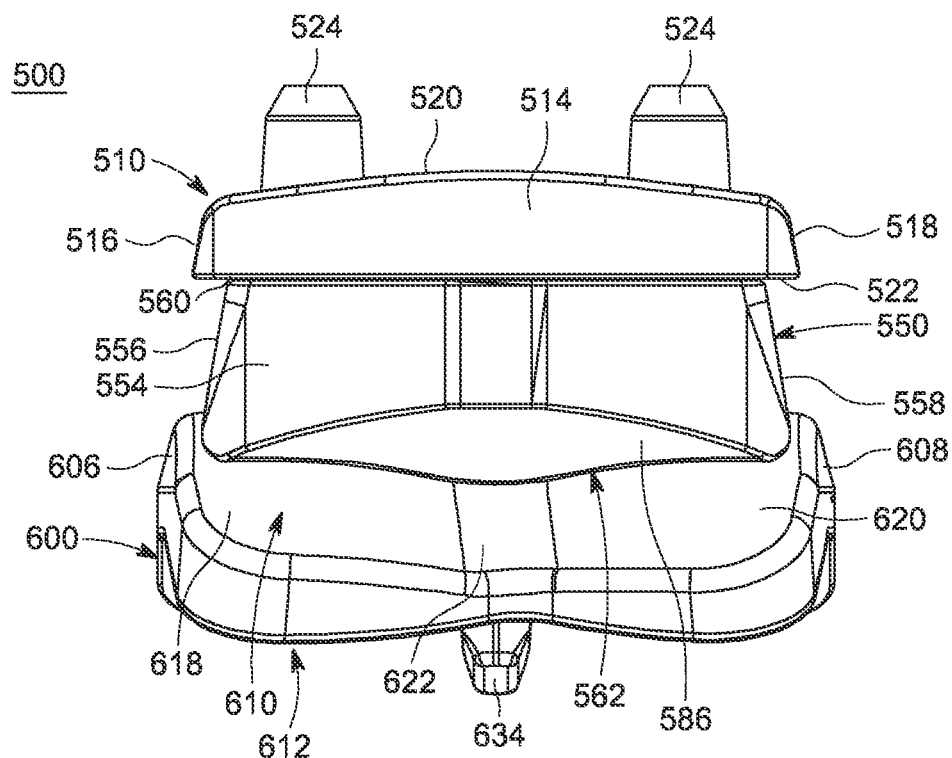
FIG. 43 is a second end view of the implant of FIG. 36, in accordance with an aspect of the present disclosure.

Referring now to FIGS. 36-51, the second member, talus component or articulating member 600 has a first end or anterior end 602 opposite a second end or posterior end 604. The second member 600 also has a first side or medial side 606 opposite a second side or lateral side 608. In addition, the second member 600 has a top surface or articulating surface 610 opposite a bottom surface or bone engagement surface 612. The second member 600 may have, for example, a trapezium shape, as shown in FIGS. 50 and 51. The first side 606 and second side 608 may be angled as they extend from the top surface 610 to the bottom surface 612 and the angle may be, for example, approximately 15° to 20° and more preferably approximately 10°. The first side 606 may be, for example, shorter than the second side 608. As shown in FIGS. 40, 41, and 43, at least a portion of the first and second sides 606, 608 may be, for example, angled or tapered from the top surface 610 toward the bottom surface 612. The second member 600 includes an anterior recess 614 extending into the first end 602. The anterior recess 614 may be, for example, positioned near a midpoint of a lateral axis of the second member 600 or, alternatively may be medially biased. The second member 600 also includes a posterior recess 616 extending into the second end 604. The posterior recess 616 may be, for example, positioned near a midpoint of the lateral axis of the second member 600 or, alternatively may be medially biased.

As shown in FIGS. 44 and 46-50, the top surface 610 of the second member 600 includes a medial articulating surface 618 extending from the first side 606 of the second member 600 toward the second side 608. The top surface 610 may also include a lateral articulating surface 620 extending from the second side 608 of the second member 600 toward the first side 606. In addition, the top surface 610 also includes a central articulating portion 622 positioned at a point where the medial articulating surface 618 contacts the lateral articulating surface 620.

The medial articulating surface 618 may include at least one first curvature along a longitudinal axis and at least one second curvature perpendicular to the longitudinal axis, as shown in FIG. 49. The lateral articulating surface 620 has at least one third curvature along the longitudinal axis and at least one fourth curvature perpendicular to the longitudinal axis. In addition, the central articulating portion 622 may have a concave curvature on the top surface 610 of the second member 600 and the medial and lateral articulating surfaces 618, 620 may have convex curvatures on the top surface 610 of the second member 600. The articulating surface 610 of the second member 600 may include, for example, at least one coronal radii and the at least one coronal radii may have, for example, a range of approximately 12 mm to 26 mm for a size 1 second member 600, a range of approximately 14 mm to 30 mm for a size 3 second member 600, and a range of approximately 17 mm to 34 mm for a size 5 second member 600. The articulating surface 610 of the second member 600 may include, for example, at least one sagittal radii and the at least one sagittal radii may have, for example, a range of approximately 18 mm to 25 mm for a size 1 second member 600, a range of approximately 20 mm to 28 mm for a size 3 second member 600, and a range of approximately 21 mm to 30 mm for a size 5 second member 600. In an embodiment, the anterior portion of the second member 600 may include a first sagittal radius of the lateral articulating surface 620 and a second sagittal radius of the medial articulating surface 618. The first sagittal radius may be, for example, larger than the second sagittal radius. In addition, the posterior portion of the second member 600 may include a third sagittal radius of the lateral articulating surface 620 and a fourth sagittal radius of the medial articulating surface 618. The third sagittal radius may be, for example, smaller than the fourth sagittal radius. A larger anterior lateral sagittal radius than anterior medial sagittal radius and a smaller posterior lateral sagittal radius than posterior medial sagittal radius allow for the joint axis of rotation to point distally and laterally during dorsiflexion and distally and medially during plantarflexion.

Referring now to FIGS. 37, 39-41, 45, 48, 49, and 51, the bottom surface 612 of the second member 600 may include a first portion 624, a second portion 626, and a third portion 628. The first portion 624, the second portion 626, and the third portion 628 may each have, for example, planar surfaces. The second portion 626 may be positioned between the first portion 624 and the third portion 628. The first portion 624 may extend, for example, from the first end 602 to a first transition point 630. The second portion 626 may extend, for example, from the first transition point 630 to a second transition point 632. The third portion 628 may extend, for example, from the second transition point 632 to the second end 604. The first portion 624 may extend away from the second portion 626 at a first angle and the third portion 628 may extend away from the second portion 626 at a second angle. The first angle may be, for example, approximately 25° to 35°, and the second angle may be, for example, approximately 25° to 35°. The bottom surface 612 of the second member 600 may be, for example, coated or textured with a biocompatible material. The texture or coating may be, for example, a plasma sprayed material, such as, a commercially-pure titanium or other biocompatible material, as known by one of ordinary skill in the art.

The bottom surface 612 of the second member 600 may also include at least one fin or stem 634 extending away from the first portion 624 of the bottom surface 612, as shown in FIGS. 36, 37, 39-49 and 51. The at least one fin 634 may be, for example, one fin 634, although other numbers of fins 634 are also contemplated. As depicted, the first fin 634 is positioned on the first portion 624 aligned with the anterior recess 614, as shown in FIGS. 45 and 51. The fin 634 may be, for example, tapered at the distal end. The at least one fin 634 may not be, for example, textured or coated, rather the at least one fin 634 may be smooth to decrease bone resorption at the resection level. The at least one fin 634 may have, for example, a cylindrical, round, oval or other like shape.

Referring to FIGS. 36-51, the insert, bearing insert, polyethylene insert, or articulating insert 550 is shown. The insert 550 includes a first end or anterior end 552 opposite a second end or posterior end 554. The insert 550 also includes a first side or medial side 556 opposite a second side or lateral side 558. In addition, the insert 550 includes a top surface 560 opposite a bottom surface 562. The first end 552 of the insert 550 includes at least one opening or cylinder 564 extending into the insert 550 from the first end 552 toward the second end 554. The at least one opening 564 may be sized and shaped or configured to receive an instrument or member, for example, a fastener or instrument to engage the insert 550 and remove the insert 550 from the first member 510. The first and second sides 556, 558 may be, for example, angled or tapered along at least a portion of the sides 556, 558 as the sides 556, 558 extend from the top surface 560 toward the bottom surface 562, as shown in FIGS. 42, 43, 46 and 47.

With continued reference to FIGS. 44 and 46-50, the top surface 560 of the insert 550 includes an engagement member or protrusion 566. The engagement member 566 includes a first engagement feature or first male dovetail 568 near the first side 556, a second engagement feature or second male dovetail 570 near the second side 558, and a third engagement feature or third male dovetail 572 near the second end 554. When the insert 550 is coupled to the first member 510, the first engagement feature 568 of the insert 550 may be configured or sized and shaped to engage the first engagement feature 532 of the first member 510, the second engagement feature 570 of the insert 550 may be configured or sized and shaped to engage the second engagement feature 534 of the first member 510, and the third engagement feature 572 of the insert 550 may be configured or sized and shaped to engage the third engagement feature 536 of the first member 510. The top surface 560 also includes a locking tab or protrusion 576. The locking tab 576 may, for example, extend away from the top surface 560 of the insert 550. The locking tab 576 may form, for example, a ramped portion extending from the top surface 560 of the insert 550 on the side positioned toward the second end 554 to a side positioned toward the first end 552. The side of the locking tab 576 positioned toward the first end 552 may have a height taller than the height of the side of the locking tab 576 positioned toward the second end 554. The locking tab 576 may be configured or sized and shaped to engage the locking groove 540 of the bottom surface 522 of the first member 510.

Referring now to FIGS. 45-49 and 51, the bottom surface 562 of the insert 550 includes a first contact surface or medial contact surface 578, a second contact surface or lateral contact surface 580, and a central contact surface 582. The first contact surface 578 extends along at least a portion of the bottom surface 562 in a medial-lateral direction from the first side 556 toward the second side 558. The first contact surface 578 also extends along at least a portion of the bottom surface 562 in an anterior-posterior direction from a position near the first end 552 toward a position near the second end 554. The second contact surface 580 extends along at least a portion of the bottom surface 562 from the second side 558 toward the first side 556. The second contact surface 580 also extends along at least a portion of the bottom surface 562 in an anterior-posterior direction from a position near the first end 552 toward a position near the second end 554. The central contact surface or central sulcus 582 is positioned between the first contact surface 578 and the second contact surface 580. The central contact surface 582 also extends along at least a portion of the bottom surface 562 in an anterior-posterior direction from a position near the first end 552 toward a position near the second end 554. The first and second contact surfaces 578, 580 form a bi-condylar surface, as shown in FIGS. 42, 43, and 45-47. The centers of the radii of the bi-condylar surface may be, for example, spaced between approximately 18 mm and 26 mm for all sizes of the insert 550. More specifically, the centers of radii of the bi-condylar surface may be, for example, approximately 20 mm for a size 1 insert 550, approximately 22 mm for a size 3 insert 550, and approximately 24 mm for a size 5 insert 550.

With continued reference to FIGS. 45-49 and 51, the first contact surface 578 includes at least one first curvature along a longitudinal axis and at least one second curvature along a lateral axis. The second contact surface 580 includes at least one third curvature along a longitudinal axis and at least one fourth curvature along a lateral axis. The central contact surface 582 includes at least one curvature. The curvatures of the first and second contact surfaces 578, 580 may be, for example, concave curvatures and the at least one curvature of the central contact surface 582 may be, for example, a convex curvature. The central contact surface 582 may provide, for example, stability in a medial-lateral direction. The central contact surface 582 may have, for example, a height ranging from approximately 1.5 mm and 2 mm. The insert 550 may also have a coronal radii and the coronal radii may be, for example, approximately 1.10 times the coronal radii of the talus. In addition, the insert 550 may have at least one sagittal radii. The at least one sagittal radii of the insert 550 may be, for example, multiple tangent and/or continuous radii, which may include varying levels of conformity with the sagittal radii of the second member 600. The sagittal radii may have, for example, a range of approximately 25 mm to 34 mm for all sizes of the insert 550. More specifically, the sagittal radii may be, for example, approximately 25 mm to 26 mm for the size 1 insert 550 and approximately 33 mm to 34 mm for the size 5 insert 550.

Referring now to FIGS. 37, 39-43, 45-49 and 51, the bottom surface 562 may also include, for example, a first angled or tapered portion 584 and a second angled or tapered portion 586. The first angled portion 584 may be, for example, positioned to extend from the first end 552 to the anterior portion of the contact surfaces 578, 580, 582 of the bottom surface 562 of the insert 550. The second angled portion 586 may be, for example, positioned to extend from the second end 554 to the posterior portion of the contact surfaces 578, 580, 582 of the bottom surface 562 of the insert 550. The first angled portion 584 and the second angled portion 586 may alternatively be, for example, non-planar surfaces including at least one concave or convex curvature. The non-planar surfaces may, for example, still be angled or tapered between the ends 552, 554 and the contact surfaces 578, 580, 582 of the insert 550.

As shown in FIGS. 36-43, when assembled and/or implanted, the top surface 560 of the insert 550 couples to a bottom surface 522 of the first member 510. In addition, the top surface 610 of the second member 600 is configured or sized and shaped to articulate with the bottom surface 562 of the insert 550. Specifically, the medial articulating surface 618 of the second member 600 is configured to articulate with the first contact surface 578 of the insert 550, the lateral articulating surface 620 of the second member 600 is configured to articulate with the second contact surface 580 of the insert 550, and the central portion 622 of the second member 600 is configured to articulate with the third contact surface 582 of the insert 550.

Referring now to FIGS. 52-63, an implant 650 is shown. The implant 650 includes a first member or tibia base 510, an insert 660, and a second member, talus component, or articulating member 600. The first member 510 and the second member 600 may be of the type described above with reference to implant 500 and FIGS. 36-51. The insert 660 includes a top surface 670 and a bottom surface 672. The top surface 670 of the insert 660 couples to the first member 510 and the bottom surface 672 engages the second member 600.

With continued reference to FIGS. 52-63, the insert, bearing insert, polyethylene insert, or articulating insert 660 is shown. The insert 660 includes a first end or anterior end 662 opposite a second end or posterior end 664. The insert 660 also includes a first side or medial side 666 opposite a second side or lateral side 668. In addition, the insert 660 includes a top surface 670 opposite a bottom surface 672. The first end 662 of the insert 660 includes at least one opening or cylinder 674 extending into the insert 660 from the first end 662 toward the second end 664. The at least one opening 674 may be sized and shaped or configured to receive an instrument or member, for example, a fastener or instrument to engage the insert 660 and remove the insert 660 from the first member 510. The first and second sides 666, 668 may be, for example, angled or tapered along at least a portion of the sides 666, 668 as the sides 666, 668 extend from the top surface 670 toward the bottom surface 672, as shown in FIGS. 52, 53, 58 and 59.

With continued reference to FIGS. 56 and 58-62, the top surface 670 of the insert 660 is the same or similar to the top surface 560 of the insert 550. The top surface 670 includes an engagement member or protrusion 676, which is the same or similar to the engagement member or protrusion 566. The engagement member 676 includes a first engagement feature or first male dovetail 678 near the first side 666, which is the same or similar to the first engagement feature or first male dovetail 568 and which will not be described again here in detail for brevity sake. The engagement member 676 also includes a second engagement feature or second male dovetail 680 near the second side 668, which is the same or similar to the second engagement feature or second male dovetail 570 and which will not be described again here in detail for brevity sake. The engagement member 676 may further include a third engagement feature or third male dovetail 682 near the second end 664, which is the same or similar to the third engagement feature or third male dovetail 572 and which will not be described again here in detail for brevity sake. When the insert 660 is coupled to the first member 510, the first engagement feature 678 of the insert 660 may be configured or sized and shaped to engage the first engagement feature 532 of the first member 510, the second engagement feature 680 of the insert 660 may be configured or sized and shaped to engage the second engagement feature 534 of the first member 510, and the third engagement feature 682 of the insert 660 may be configured or sized and shaped to engage the third engagement feature 536 of the first member 510. The top surface 670 also includes a locking tab or protrusion 686. The locking tab 686 may be the same or similar to the locking tab 576 of insert 550 as described in greater detail above and which will not be described again here for brevity sake. The locking tab 686 may be configured or sized and shaped to engage the locking groove 540 of the bottom surface 522 of the first member 510.

Referring now to FIGS. 57, 60, 61 and 63, the bottom surface 672 of the insert 660 includes a first contact surface or medial contact surface 688, a second contact surface or lateral contact surface 690, and a central contact surface 692. The first contact surface 688 extends along at least a portion of the bottom surface 672 in a medial-lateral direction from the first side 666 toward the second side 668. The first contact surface 688 also extends along at least a portion of the bottom surface 672 in an anterior-posterior direction from a position near the first end 662 toward a position near the second end 662. The second contact surface 690 extends along at least a portion of the bottom surface 672 from the second side 668 toward the first side 666. The second contact surface 690 also extends along at least a portion of the bottom surface 672 in an anterior-posterior direction from a position near the first end 662 toward a position near the second end 664. The central contact surface or central sulcus 692 is positioned between the first contact surface 688 and the second contact surface 690. The central contact surface 692 also extends along at least a portion of the bottom surface 672 in an anterior-posterior direction from a position near the first end 662 toward a position near the second end 664. The first and second contact surfaces 688, 690 form a bi-condylar surface, as shown in FIGS. 52, 53, and 57-59. The centers of the radii of the bi-condylar surface may be, for example, spaced between approximately 18 mm and 26 mm for all sizes of the insert 660. More specifically, the centers of radii of the bi-condylar surface may be, for example, approximately 20 mm for a size 1 insert 660, approximately 22 mm for a size 3 insert 660, and approximately 24 mm for a size 5 insert 660.

With continued reference to FIGS. 57-61 and 63, the first contact surface 688 includes at least one first curvature along a longitudinal axis and at least one second curvature along a lateral axis. The second contact surface 690 includes at least one third curvature along a longitudinal axis and at least one fourth curvature along a lateral axis. The central contact surface 692 includes at least one curvature. The curvatures of the first and second contact surfaces 688, 690 may be, for example, concave curvatures and the at least one curvature of the central contact surface 692 may be, for example, a convex curvature. The central contact surface 692 may provide, for example, stability in a medial-lateral direction. The central contact surface 692 may have, for example, a height ranging from approximately 1.5 mm and 2 mm. The insert 660 may also have a coronal radii and the coronal radii may be, for example, approximately 1.10 times the coronal radii of the talus. In addition, the insert 660 may have at least one sagittal radii. The at least one sagittal radii of the insert 660 may be, for example, multiple tangent and/or continuous radii, which may include varying levels of conformity with the sagittal radii of the second member 600. The sagittal radii may have, for example, a range of approximately 25 mm to 34 mm for all sizes of the insert 660. More specifically, the sagittal radii may be, for example, approximately 25 mm to 26 mm for the size 1 insert 660 and approximately 33 mm to 34 mm for the size 5 insert 660.

Referring now to FIGS. 53, 54, 55, 57-61 and 63, the bottom surface 672 may also include, for example, a first angled or tapered portion 694 and a second angled or tapered portion 696. The first angled portion 694 may be, for example, positioned to extend from the first end 662 to the anterior portion of the contact surfaces 688, 690, 692 of the bottom surface 672 of the insert 660. The first angled portion 694 may be, for example, longer than the first angled portion 584 of the insert 550. The second angled portion 696 may be, for example, positioned to extend from the second end 664 to the posterior portion of the contact surfaces 688, 690, 692 of the bottom surface 672 of the insert 660. The second angled portion 696 may be, for example, shorter than the second angled portion 586 of the insert 550. The first angled portion 694 and the second angled portion 696 may alternatively be, for example, non-planar surfaces including at least one concave or convex curvature. The non-planar surfaces may, for example, still be angled or tapered between the ends 662, 664 and the contact surfaces 688, 690, 692 of the insert 660.

Figure 54:
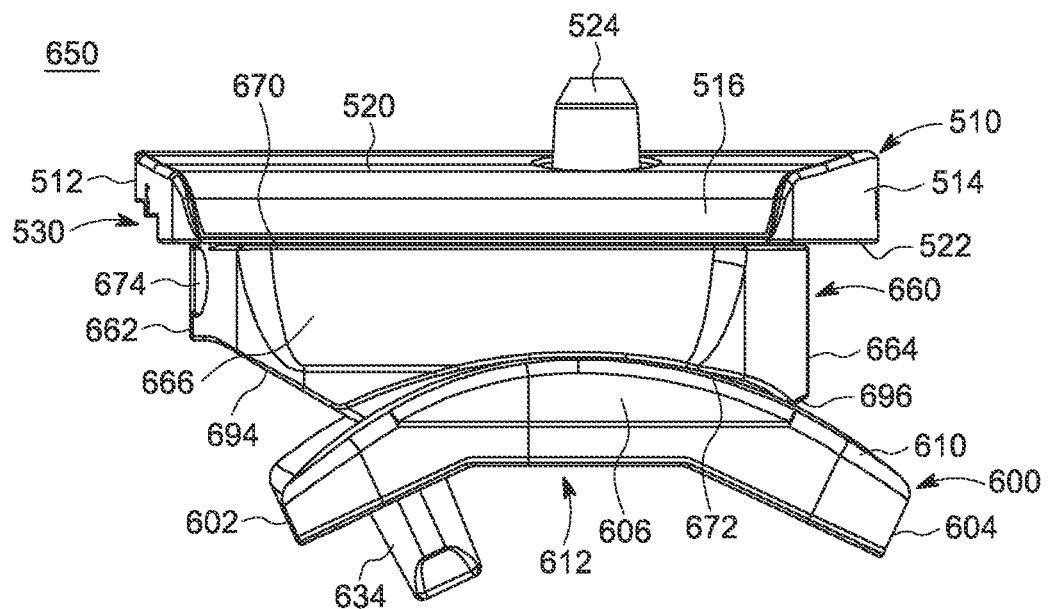
FIG. 54 is a first side view of the implant of FIG. 52, in accordance with an aspect of the present disclosure.
Figure 55:
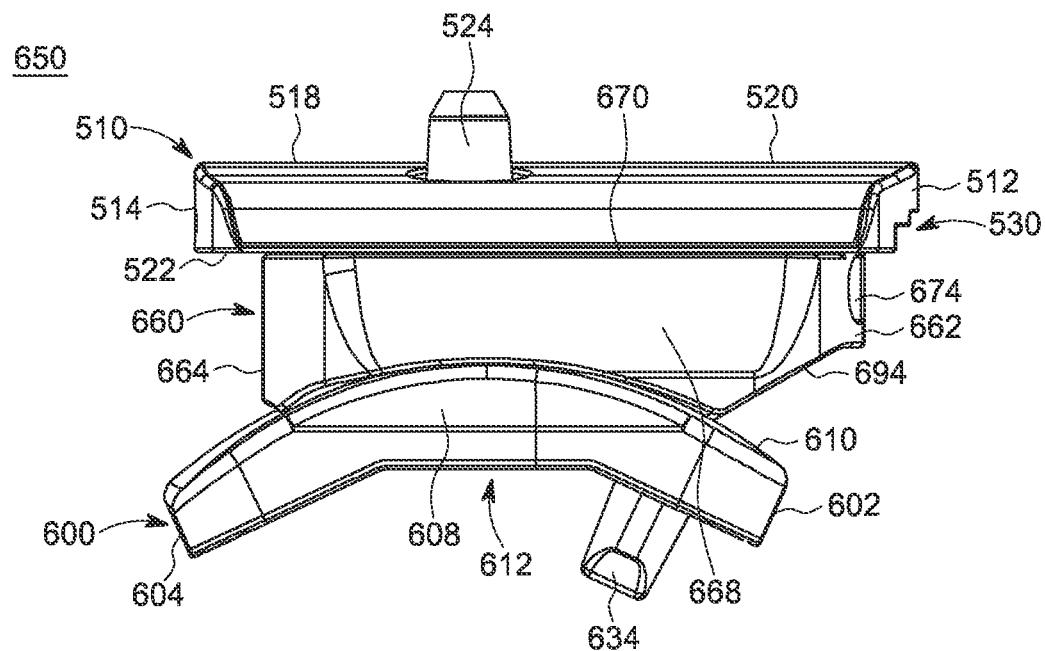
FIG. 55 is a second side view of the implant of FIG. 52, in accordance with an aspect of the present disclosure.
Figure 56:
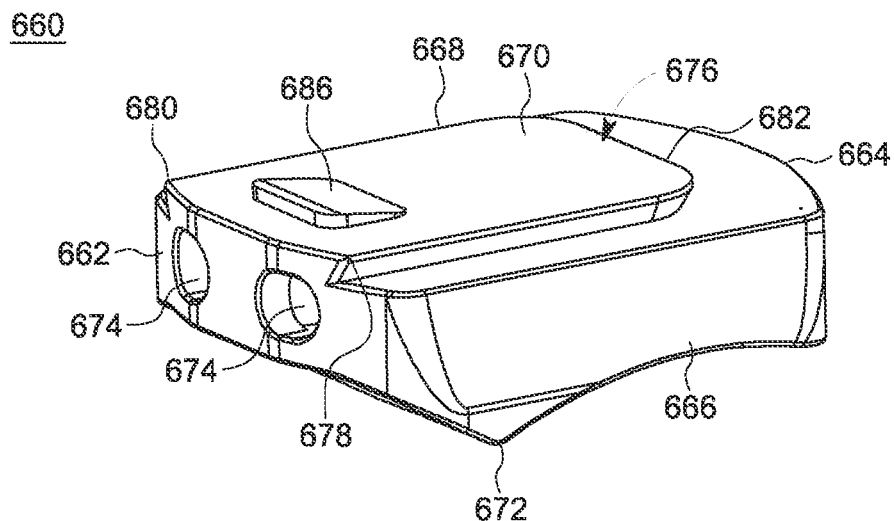
FIG. 56 is an exploded, first perspective view of an insert of the implant of FIG. 52, in accordance with an aspect of the present disclosure.
Figure 57:
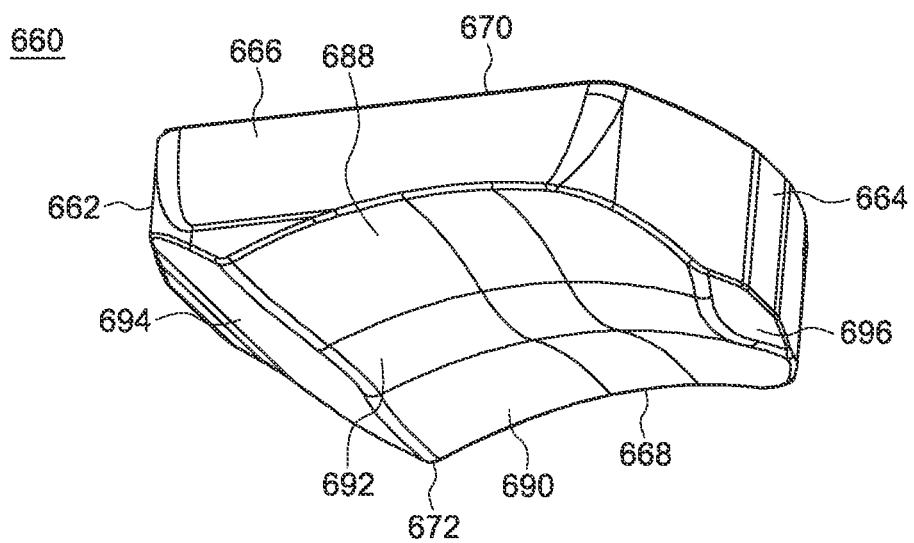
FIG. 57 is an exploded, second perspective view of the insert of FIG. 56, in accordance with an aspect of the present disclosure.
Figure 58:
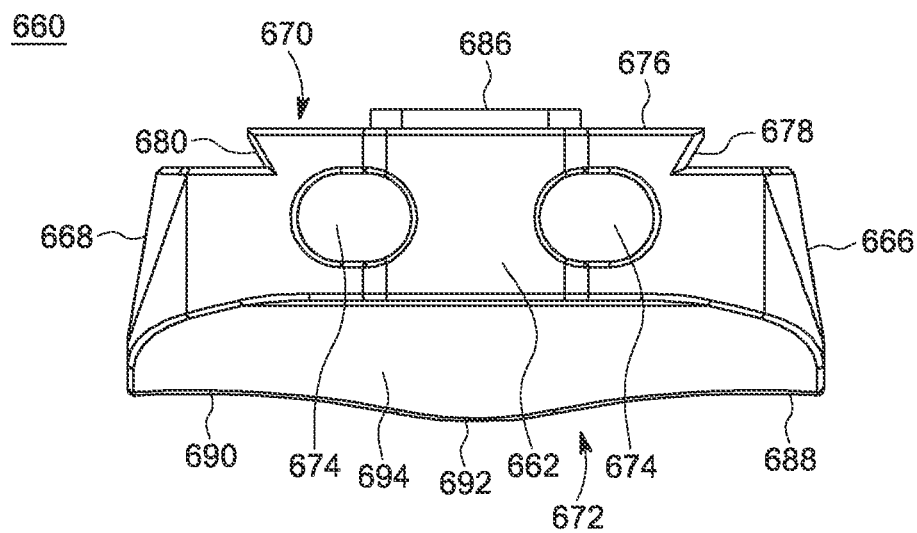
FIG. 58 is a first end view of the insert of FIG. 56, in accordance with an aspect of the present disclosure.
Figure 59:
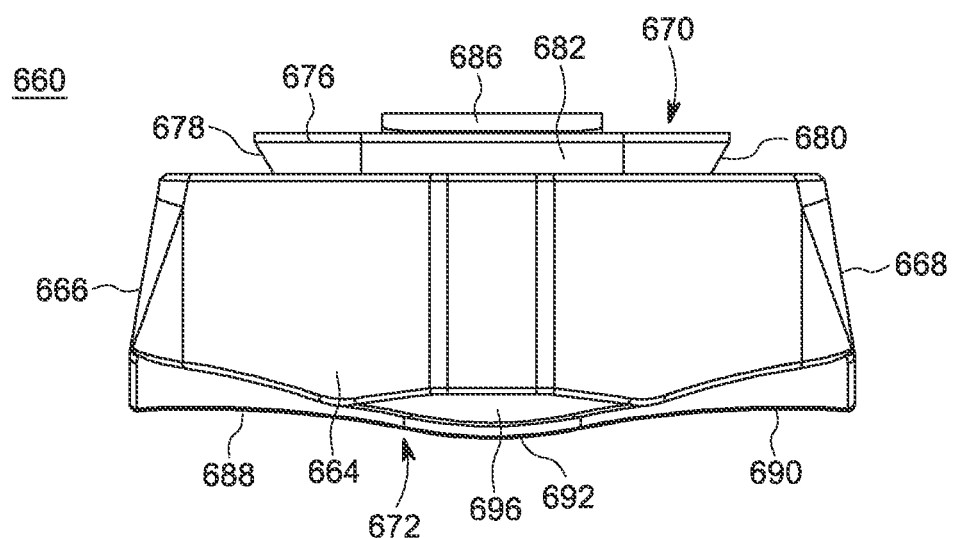
FIG. 59 is a second end view of the insert of FIG. 56, in accordance with an aspect of the present disclosure.
Figure 60:
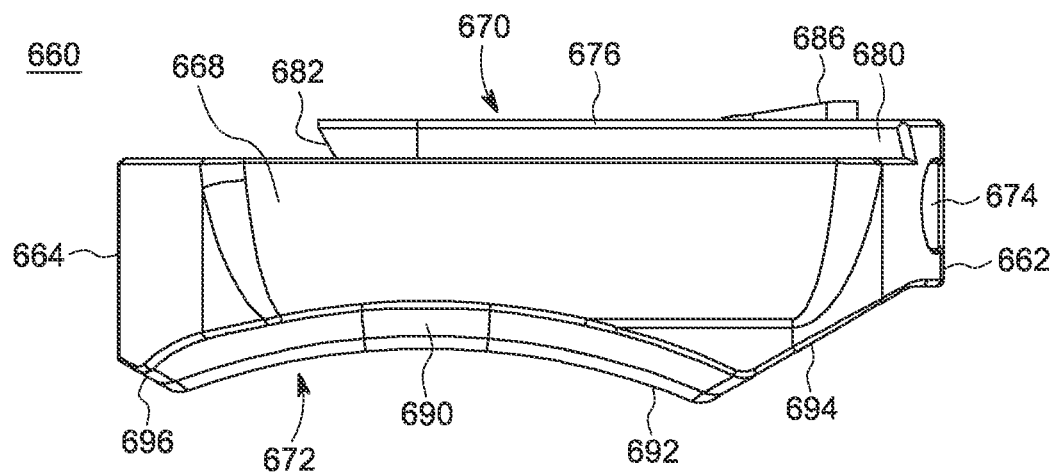
FIG. 60 is a first side view of the insert of FIG. 56, in accordance with an aspect of the present disclosure.
Figure 61:
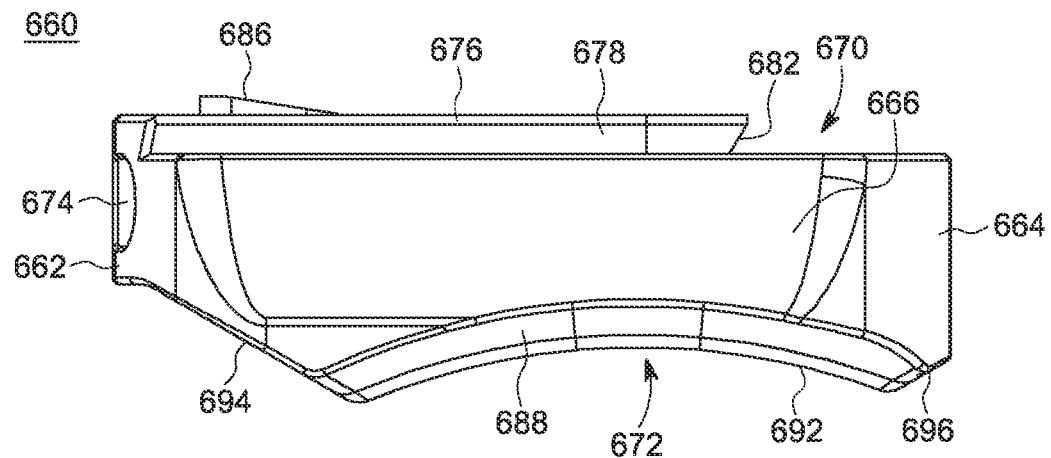
FIG. 61 is a second side view of the insert of FIG. 56, in accordance with an aspect of the present disclosure.
Figure 63:
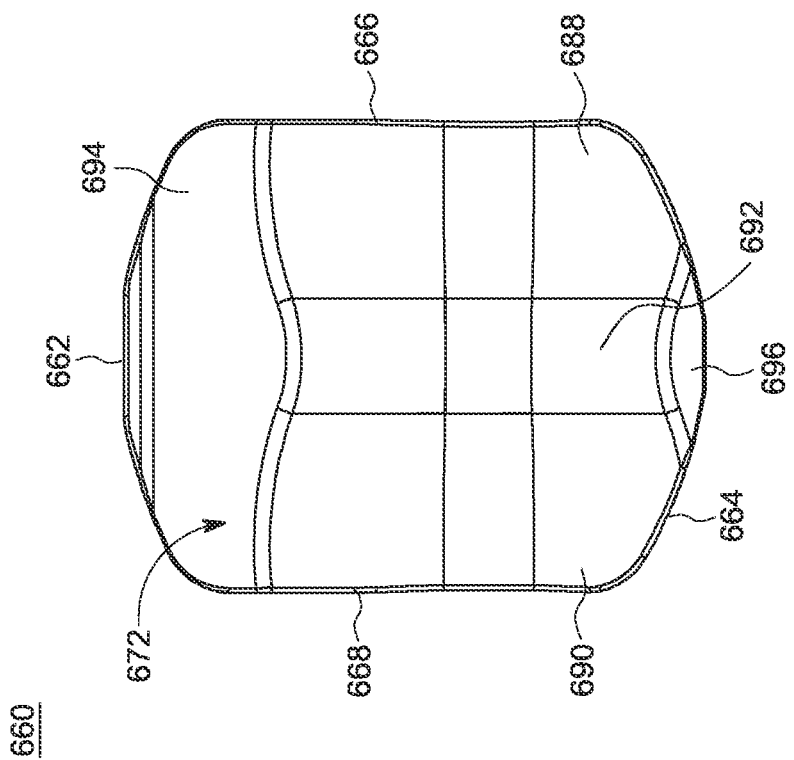
FIG. 63 is a bottom view of the insert of FIG. 56, in accordance with an aspect of the present disclosure.
Figure 62:
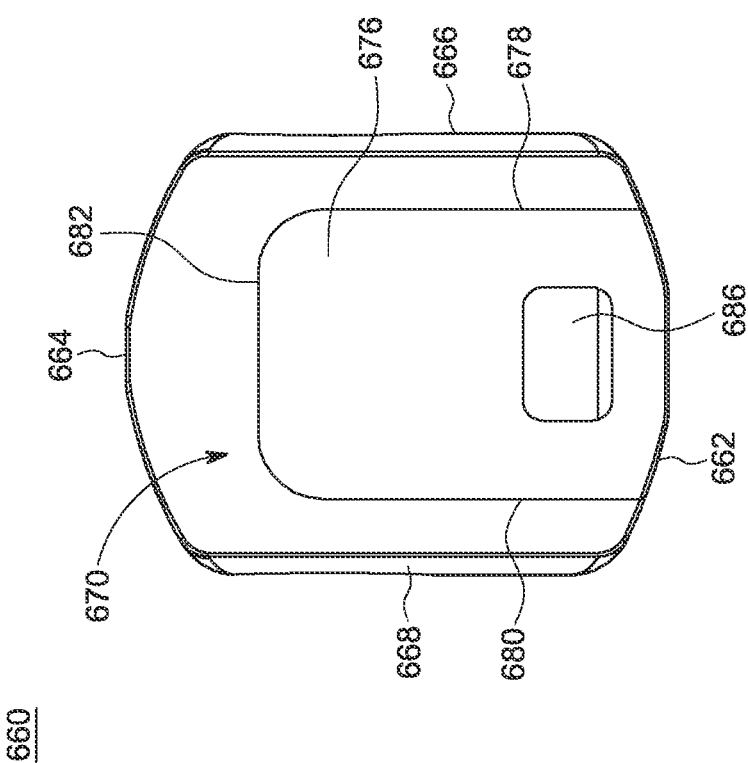
FIG. 62 is a top view of the insert of FIG. 56, in accordance with an aspect of the present disclosure.
Figure 64:
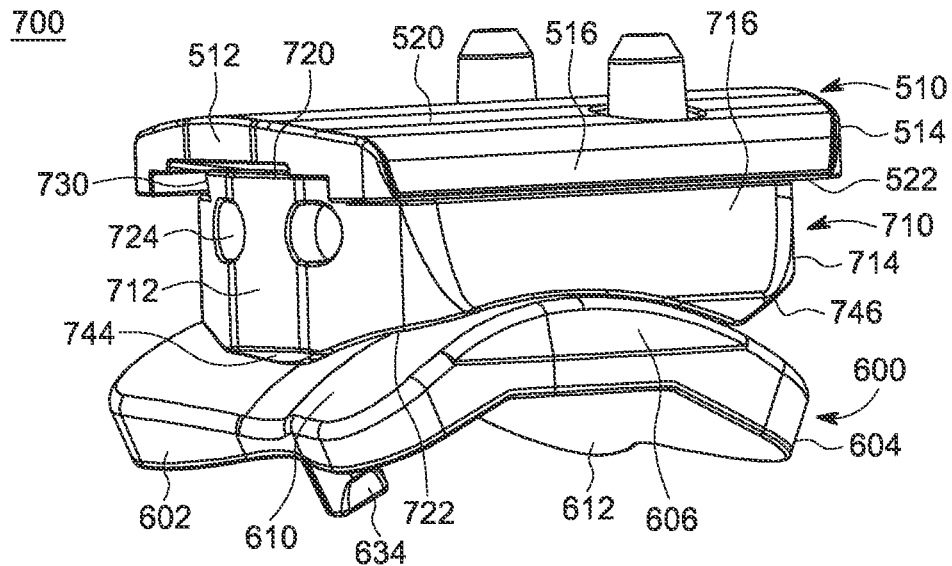
FIG. 64 is a first perspective view of an implant, in accordance with an aspect of the present disclosure.
Figure 65:
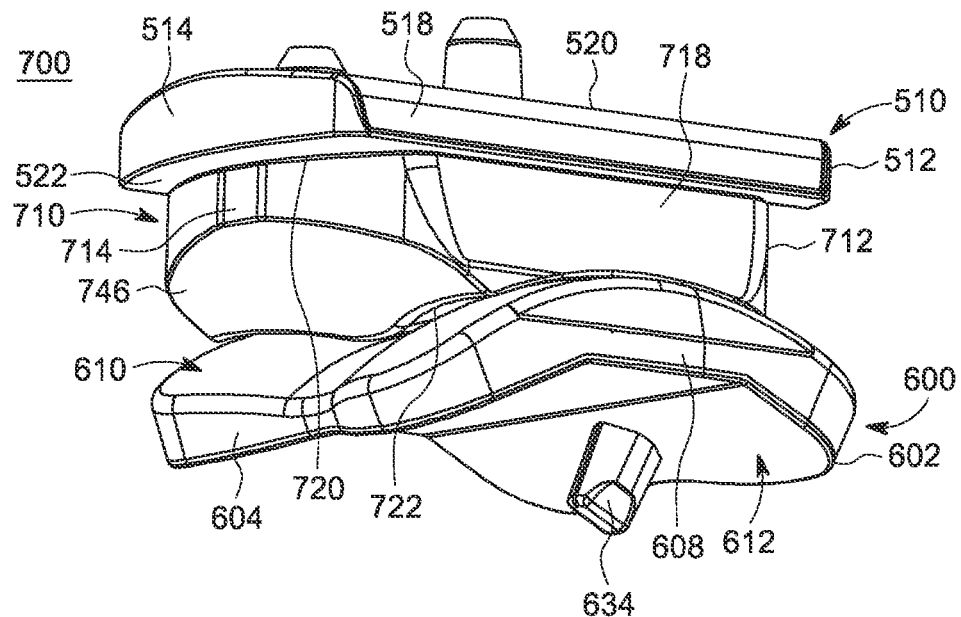
FIG. 65 is a second perspective view of the implant of FIG. 64, in accordance with an aspect of the present disclosure.

As shown in FIGS. 52-55, when assembled and/or implanted, the top surface 670 of the insert 660 couples to a bottom surface 522 of the first member 510. In addition, the top surface 610 of the second member 600 is configured or sized and shaped to articulate with the bottom surface 672 of the insert 660. Specifically, the medial articulating surface 618 of the second member 600 is configured to articulate with the first contact surface 688 of the insert 660, the lateral articulating surface 620 of the second member 600 is configured to articulate with the second contact surface 690 of the insert 660, and the central portion 622 of the second member 600 is configured to articulate with the third contact surface 692 of the insert 660. As shown in FIGS. 54 and 55, the first member 510 and coupled insert 660 are positioned on the second member 600 such that the first member 510 and insert 660 are shifted in an anterior direction on the second member 600. The implant 650 includes an insert 660 to anteriorly shift the first member 510 relative to the second member 600 and the neutral positioning of implant 500.

Referring now to FIGS. 64-75, an implant 700 is shown. The implant 700 includes a first member or tibia base 510, an insert 710, and a second member, talus component, or articulating member 600. The first member 510 and the second member 600 may be of the type described above with reference to implant 500 and FIGS. 36-51. The insert 710 includes a top surface 720 and a bottom surface 722. The top surface 720 of the insert 710 couples to the first member 510 and the bottom surface 722 engages the second member 600.

With continued reference to FIGS. 64-75, the insert, bearing insert, polyethylene insert, or articulating insert 710 is shown. The insert 710 includes a first end or anterior end 712 opposite a second end or posterior end 714. The insert 710 also includes a first side or medial side 716 opposite a second side or lateral side 718. In addition, the insert 710 includes a top surface 720 opposite a bottom surface 722. The first end 712 of the insert 710 includes at least one opening or cylinder 724 extending into the insert 710 from the first end 712 toward the second end 714. The at least one opening 724 may be sized and shaped or configured to receive an instrument or member, for example, a fastener or instrument to engage the insert 710 and remove the insert 710 from the first member 510. The first and second sides 716, 718 may be, for example, angled or tapered along at least a portion of the sides 716, 718 as the sides 716, 718 extend from the top surface 720 toward the bottom surface 722, as shown in FIGS. 64, 65, 70 and 71.

With continued reference to FIGS. 68 and 70-74, the top surface 720 of the insert 710 is the same or similar to the top surface 560 of the insert 550 and the top surface 670 of the insert 660. The top surface 720 includes an engagement member or protrusion 726, which is the same or similar to the engagement member or protrusion 566, 676. The engagement member 726 includes a first engagement feature or first male dovetail 728 near the first side 716, which is the same or similar to the first engagement feature or first male dovetail 568, 678 and which will not be described again here in detail for brevity sake. The engagement member 726 also includes a second engagement feature or second male dovetail 730 near the second side 718, which is the same or similar to the second engagement feature or second male dovetail 570, 680 and which will not be described again here in detail for brevity sake. The engagement member 676 may further include a third engagement feature or third male dovetail 732 near the second end 714, which is the same or similar to the third engagement feature or third male dovetail 572, 682 and which will not be described again here in detail for brevity sake. When the insert 710 is coupled to the first member 510, the first engagement feature 728 of the insert 710 may be configured or sized and shaped to engage the first engagement feature 532 of the first member 510, the second engagement feature 730 of the insert 710 may be configured or sized and shaped to engage the second engagement feature 534 of the first member 510, and the third engagement feature 732 of the insert 710 may be configured or sized and shaped to engage the third engagement feature 536 of the first member 510. The top surface 720 also includes a locking tab or protrusion 736. The locking tab 736 may be the same or similar to the locking tab 576, 686 of insert 550, 660, respectively, as described in greater detail above and which will not be described again here for brevity sake. The locking tab 736 may be configured or sized and shaped to engage the locking groove 540 of the bottom surface 522 of the first member 510.

Referring now to FIGS. 69, 72, 73 and 75, the bottom surface 722 of the insert 710 includes a first contact surface or medial contact surface 738, a second contact surface or lateral contact surface 740, and a central contact surface 742. The first contact surface 738 extends along at least a portion of the bottom surface 722 in a medial-lateral direction from the first side 716 toward the second side 718. The first contact surface 738 also extends along at least a portion of the bottom surface 722 in an anterior-posterior direction from a position near the first end 712 toward a position near the second end 714. The second contact surface 740 extends along at least a portion of the bottom surface 722 from the second side 718 toward the first side 716. The second contact surface 740 also extends along at least a portion of the bottom surface 722 in an anterior-posterior direction from a position near the first end 712 toward a position near the second end 714. The central contact surface or central sulcus 742 is positioned between the first contact surface 738 and the second contact surface 740. The central contact surface 742 also extends along at least a portion of the bottom surface 722 in an anterior-posterior direction from a position near the first end 712 toward a position near the second end 714. The first and second contact surfaces 738, 740 form a bi-condylar surface, as shown in FIGS. 64, 65, and 69-71. The centers of the radii of the bi-condylar surface may be, for example, spaced between approximately 18 mm and 26 mm for all sizes of the insert 710. More specifically, the centers of radii of the bi-condylar surface may be, for example, approximately 20 mm for a size 1 insert 710, approximately 22 mm for a size 3 insert 710, and approximately 24 mm for a size 5 insert 710.

With continued reference to FIGS. 69-73 and 75, the first contact surface 738 includes at least one first curvature along a longitudinal axis and at least one second curvature along a lateral axis. The second contact surface 740 includes at least one third curvature along a longitudinal axis and at least one fourth curvature along a lateral axis. The central contact surface 742 includes at least one curvature. The curvatures of the first and second contact surfaces 738, 740 may be, for example, concave curvatures and the at least one curvature of the central contact surface 742 may be, for example, a convex curvature. The central contact surface 742 may provide, for example, stability in a medial-lateral direction. The central contact surface 742 may have, for example, a height ranging from approximately 1.5 mm and 2 mm. The insert 710 may also have a coronal radii and the coronal radii may be, for example, approximately 1.10 times the coronal radii of the talus. In addition, the insert 710 may have at least one sagittal radii. The at least one sagittal radii of the insert 710 may be, for example, multiple tangent and/or continuous radii, which may include varying levels of conformity with the sagittal radii of the second member 600. The sagittal radii may have, for example, a range of approximately 25 mm to 34 mm for all sizes of the insert 710. More specifically, the sagittal radii may be, for example, approximately 25 mm to 26 mm for the size 1 insert 710 and approximately 33 mm to 34 mm for the size 5 insert 710.

Referring now to FIGS. 65-67, 69-73 and 75, the bottom surface 722 may also include, for example, a first angled or tapered portion 744 and a second angled or tapered portion 746. The first angled portion 744 may be, for example, positioned to extend from the first end 712 to the anterior portion of the contact surfaces 738, 740, 742 of the bottom surface 722 of the insert 710. The first angled portion 744 may be, for example, shorter than the first angled portion 584 of the insert 550 and the first angled portion 694 of the insert 660. The second angled portion 746 may be, for example, positioned to extend from the second end 714 to the posterior portion of the contact surfaces 738, 740, 742 of the bottom surface 722 of the insert 710. The second angled portion 746 may be, for example, longer than the second angled portion 586 of the insert 550 and the second angled portion 696 of the insert 660. The first angled portion 744 and the second angled portion 746 may alternatively be, for example, non-planar surfaces including at least one concave or convex curvature. The non-planar surfaces may, for example, still be angled or tapered between the ends 744, 746 and the contact surfaces 738, 740, 742 of the insert 710.

Figure 66:
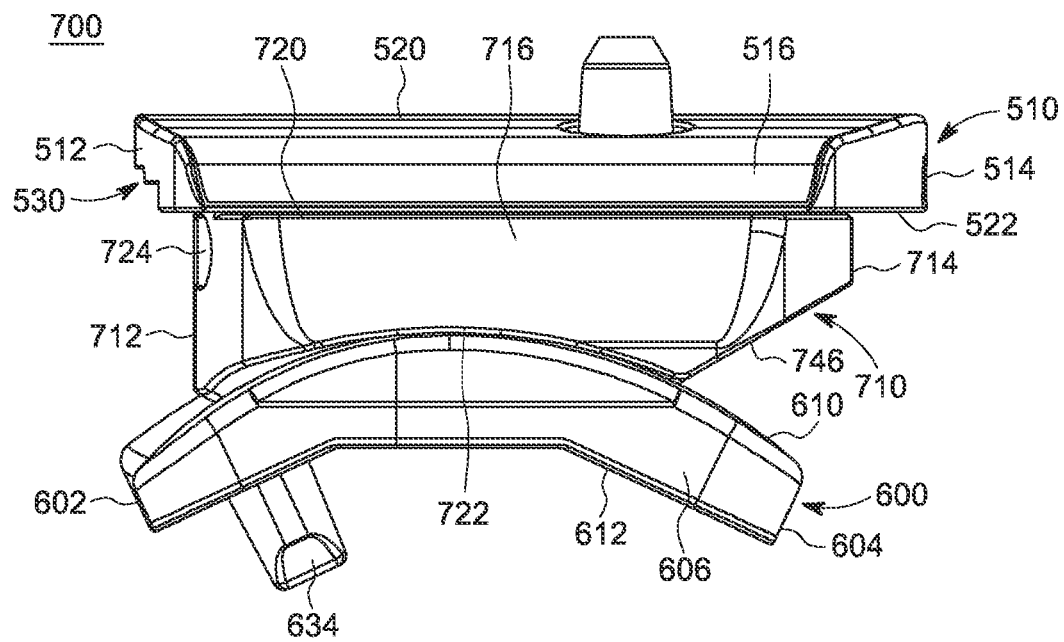
FIG. 66 is a first side view of the implant of FIG. 64, in accordance with an aspect of the present disclosure.
Figure 67:
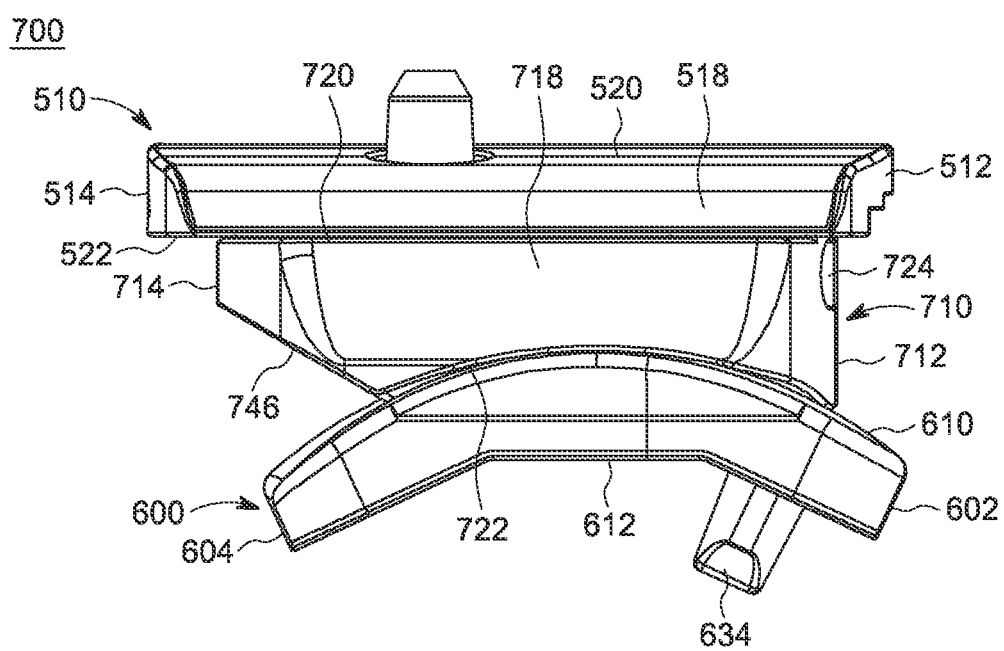
FIG. 67 is a second side view of the implant of FIG. 64, in accordance with an aspect of the present disclosure.
Figure 68:
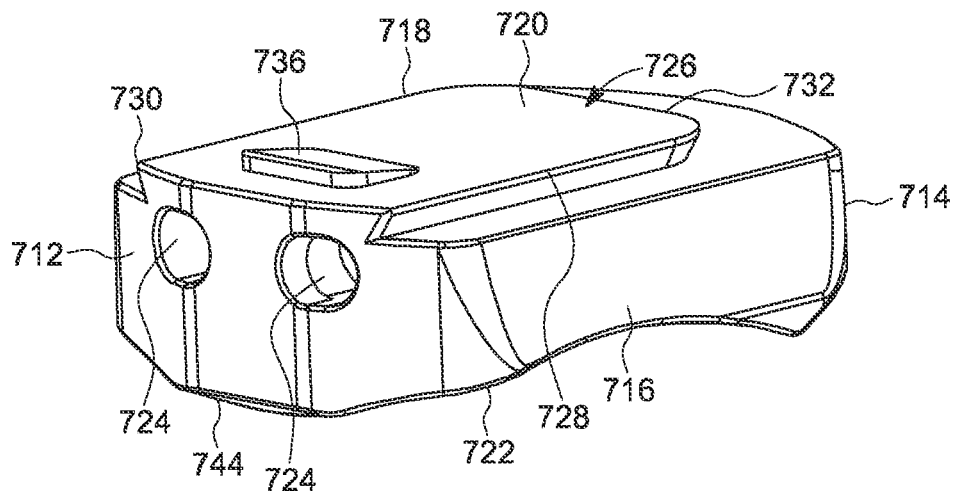
FIG. 68 is a first perspective view of another insert of the implant of FIG. 64, in accordance with an aspect of the present disclosure.
Figure 69:
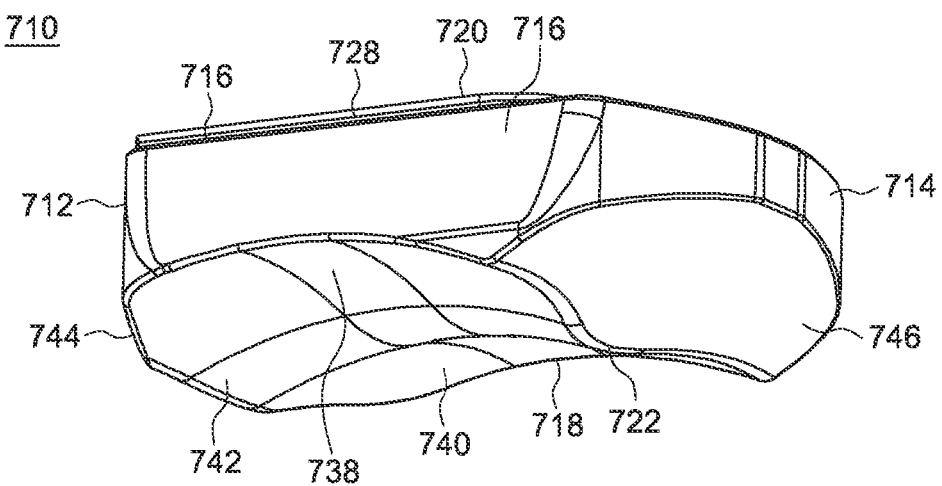
FIG. 69 is a second perspective view of another insert of the implant FIG. 64, in accordance with an aspect of the present disclosure.
Figure 70:
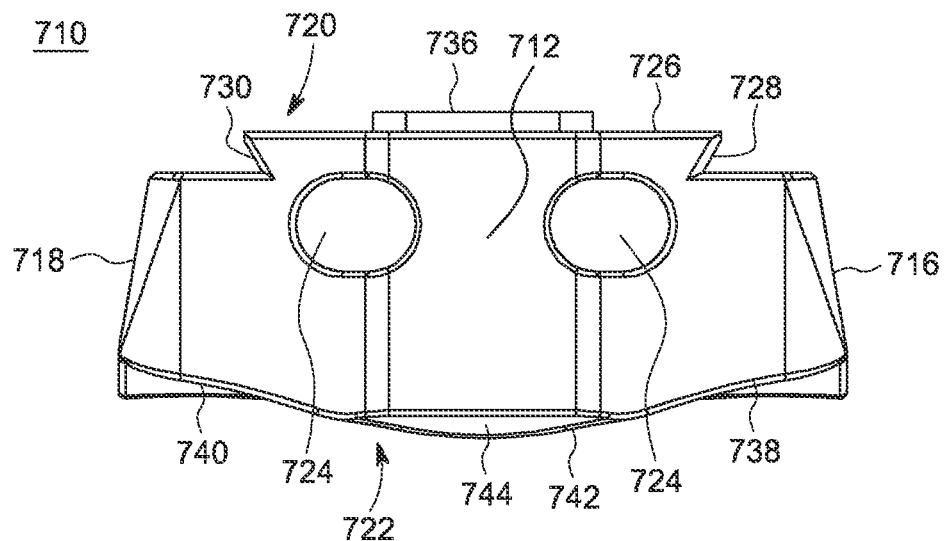
FIG. 70 is a first end view of the insert of FIG. 69, in accordance with an aspect of the present disclosure.
Figure 71:
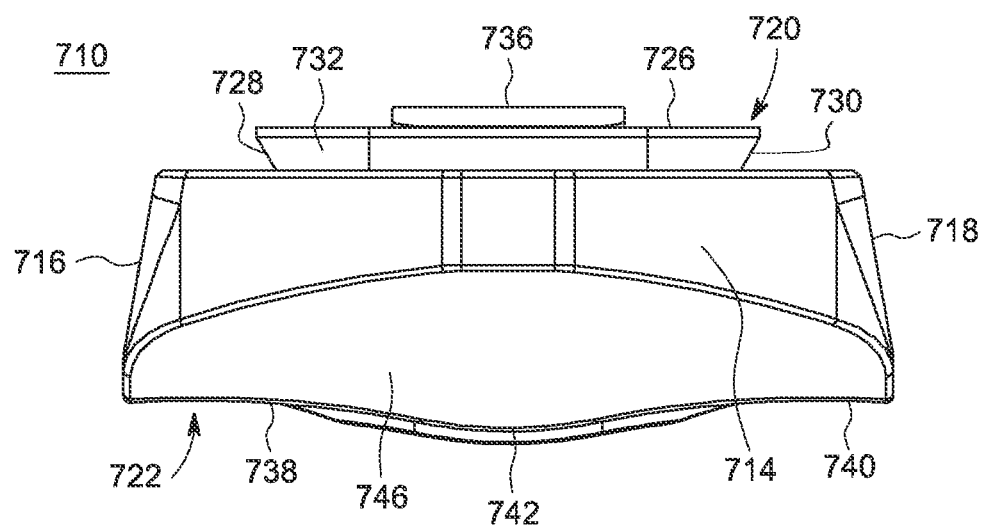
FIG. 71 is a second end view of the insert of the implant of FIG. 64, in accordance with an aspect of the present disclosure.
Figure 72:
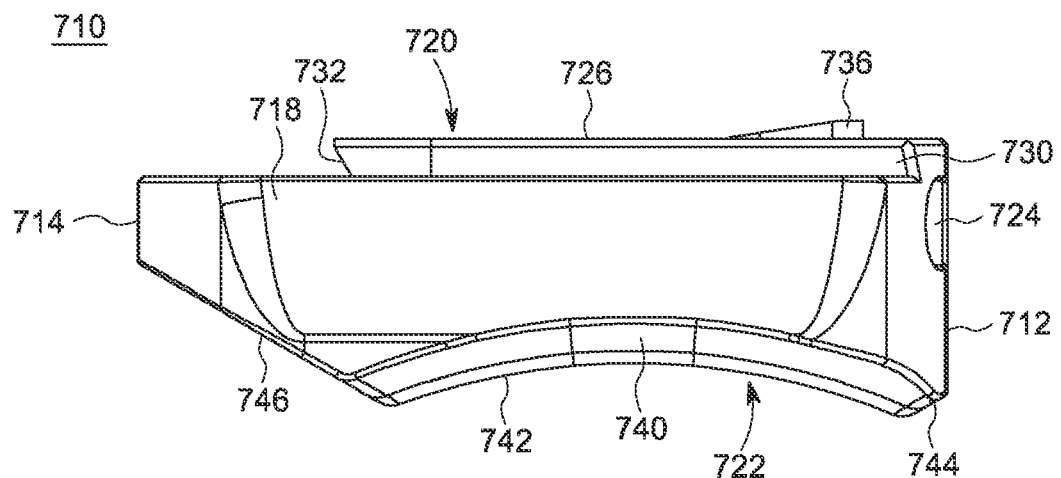
FIG. 72 is a first side view of the insert of the implant of FIG. 64, in accordance with an aspect of the present disclosure.
Figure 73:
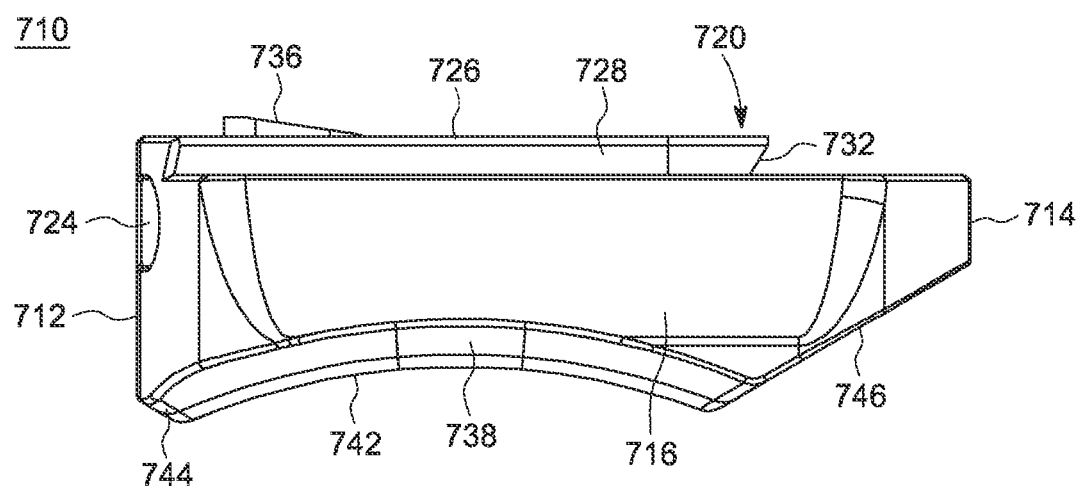
FIG. 73 is a second side view of the insert of the implant of FIG. 64, in accordance with an aspect of the present disclosure.
Figure 75:
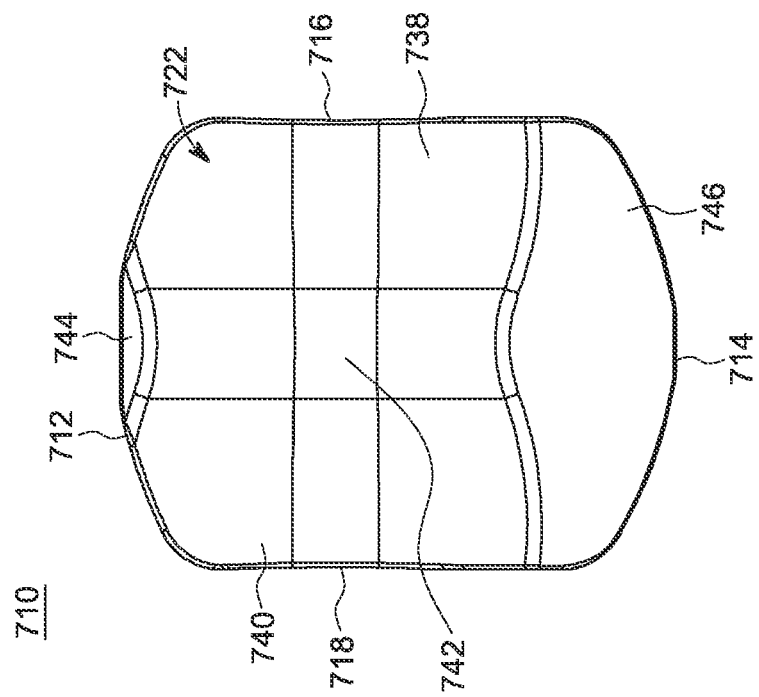
FIG. 75 is a bottom view of the insert of the implant of FIG. 64, in accordance with an aspect of the present disclosure.
Figure 74:
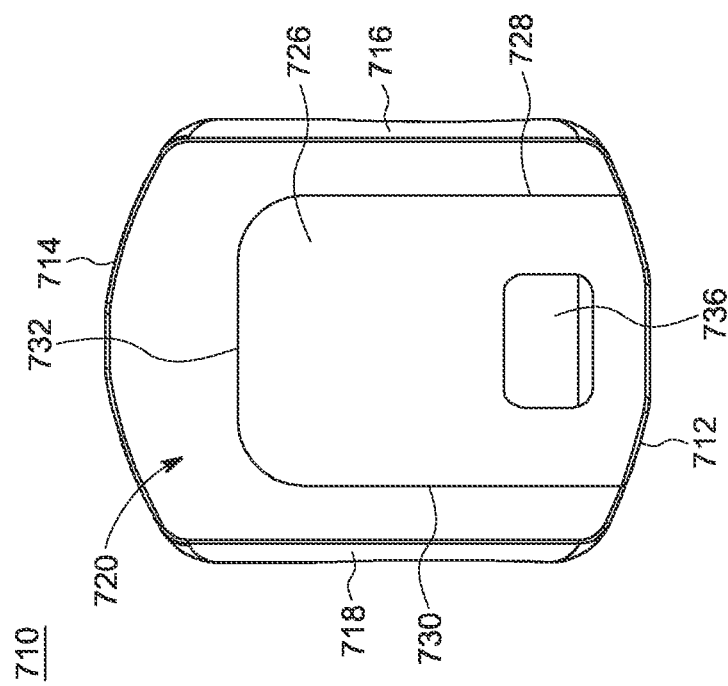
FIG. 74 is a top view of the insert of the implant of FIG. 64, in accordance with an aspect of the present disclosure.
Figure 76:
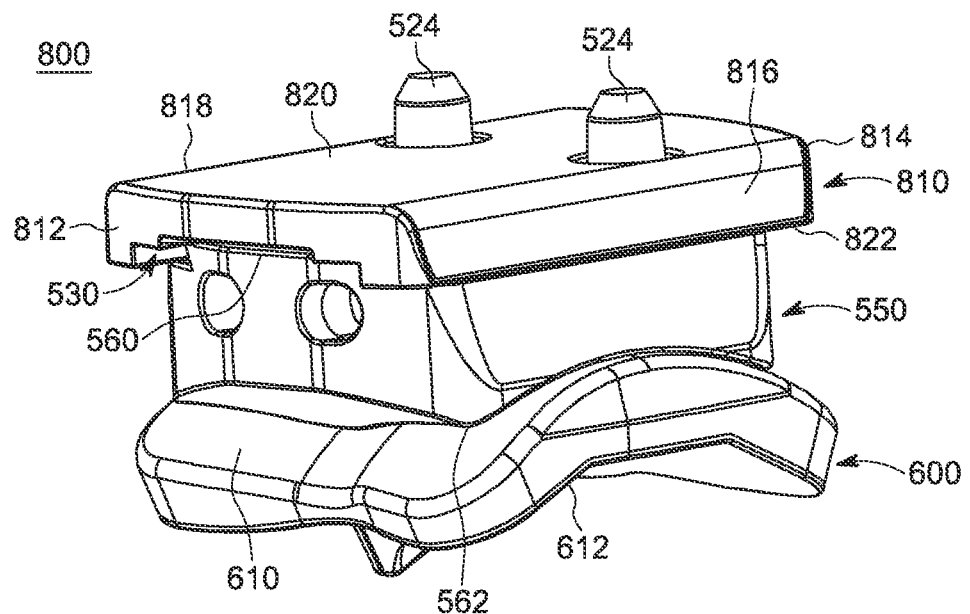
FIG. 76 is a first perspective view of an implant, in accordance with an aspect of the present disclosure.
Figure 77:
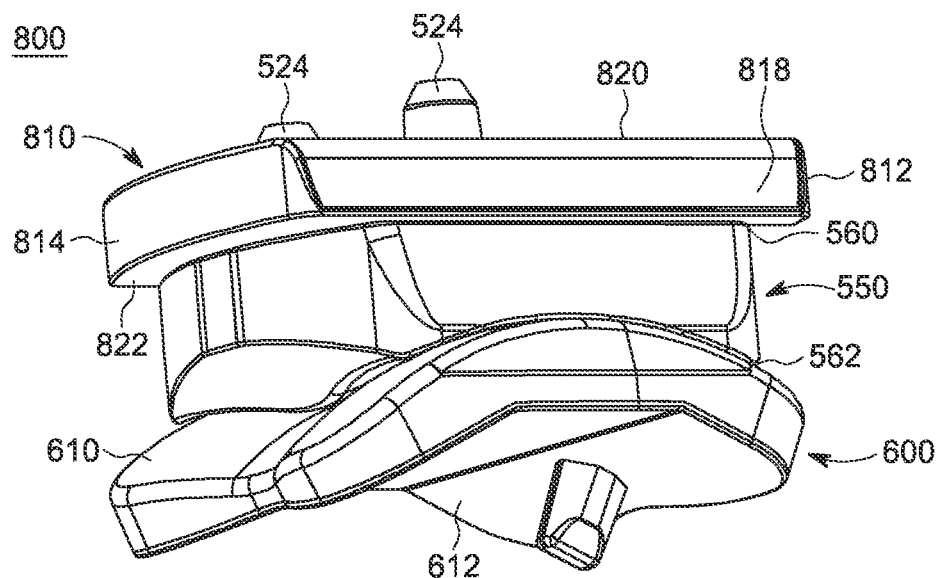
FIG. 77 is a second perspective view of the implant of FIG. 76, in accordance with an aspect of the present disclosure.
Figure 79:
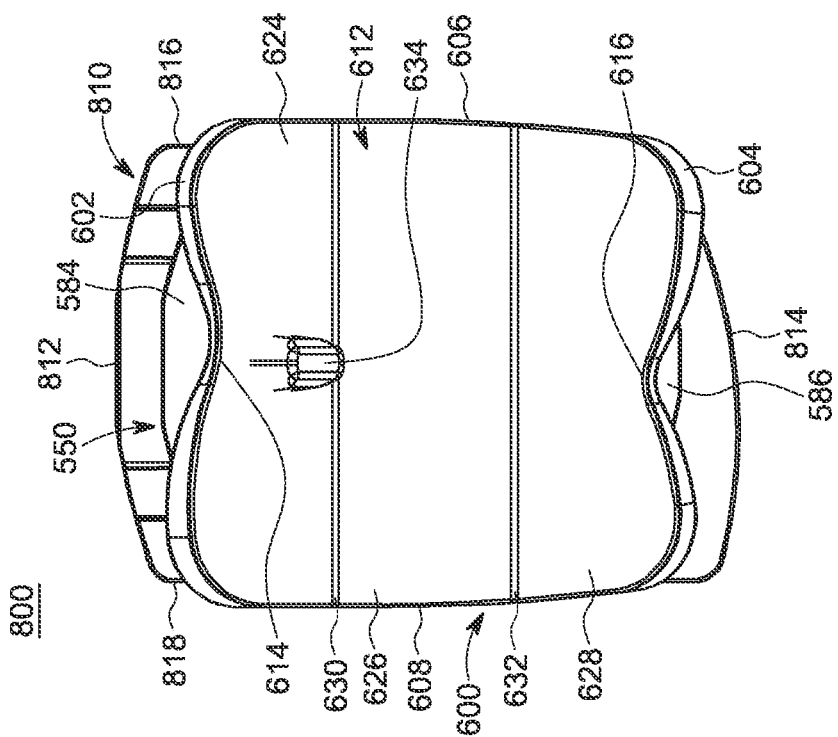
FIG. 79 is a bottom view of the implant of FIG. 76, in accordance with an aspect of the present disclosure.

As shown in FIGS. 64-67, when assembled and/or implanted, the top surface 720 of the insert 710 couples to a bottom surface 522 of the first member 510. In addition, the top surface 610 of the second member 600 is configured or sized and shaped to articulate with the bottom surface 722 of the insert 710. Specifically, the medial articulating surface 618 of the second member 600 is configured to articulate with the first contact surface 738 of the insert 710, the lateral articulating surface 620 of the second member 600 is configured to articulate with the second contact surface 740 of the insert 710, and the central portion 622 of the second member 600 is configured to articulate with the third contact surface 742 of the insert 710. As shown in FIGS. 66 and 67, the first member 510 and coupled insert 710 are positioned on the second member 600 such that the first member 510 and insert 710 are shifted in a posterior direction on the second member 600. The implant 700 includes an insert 710 to posteriorly shift the first member 510 relative to the second member 600 and the neutral positioning of implant 500.

Referring now to FIGS. 76-91, another implant 800 is shown. The implant 800 includes a first member or tibia base 810, an insert 550, and a second member, talus component, or articulating member 600. The insert 550 and second member 600 are as described in greater detail above and will not be described again here for brevity sake. The top surface 560 of the insert couples to the first member 810 and the bottom surface 562 engages the second member 600.

As shown in FIGS. 84-91, the first member 810 includes a first end or anterior end 812 opposite a second end or posterior end 814. The first member 810 also includes a first side or medial side 816 opposite a second side or lateral side 818. In addition, the first member 810 includes a top surface 820 opposite a bottom surface 822. The top surface 820 may be, for example, flat as the top surface 820 extends between the first side 816 and the second side 818, as shown in FIGS. 82, 83, 86 and 87. The top surface 820 of the first member 810 may also include, for example, sloped, tapered, or angled sides on the first side 816 and the second side 818 of the first member 810. The angle of the first and second sides 816, 818 as they extend away from the top surface 820 may be, for example, approximately 8° to 15° from vertical and more specifically approximately 10° from vertical. The edges of the first and second sides 816, 818 of the first member 810 may be, for example, rounded or curved.

As shown in the top view of FIG. 90, the first and second ends 812, 814 may include, for example, multiple arc radii as the first and second ends 812, 814 extend between the first side 816 and the second side 818. In an embodiment, the multiple arc radii of the first member 810 may be the same or similar to the multiple arc radii as described in greater detail above with reference to FIG. 35, which will not be described again here for brevity sake. In other embodiments the multiple arc radii may be different as described with respect to FIG. 35.

Figure 78:
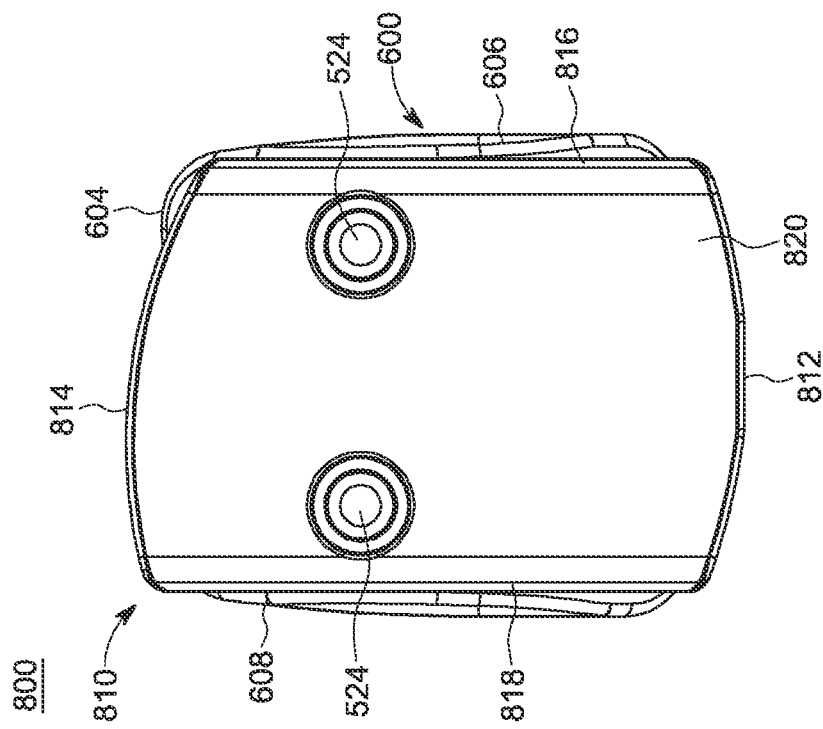
FIG. 78 is a top view of the implant of FIG. 76, in accordance with an aspect of the present disclosure.

The first member 810 may have an outer perimeter shape that may be, for example, a quadrilateral shape, such as, a generally trapezoidal from a top or bottom view, as shown in FIGS. 78, 90 and 91. The first and second sides 816, 818 may be generally parallel and the first end 812 and second end 814 may be, for example, angled or curved as they extend from the first side 816 to the second side 818. In an embodiment, the length of the first or medial side 816 may be, for example, shorter than the length of the second or lateral side 818. The angle or curvature of the first end 812 may be, for example, smaller than the angle of the second end 814. The top surface 820, first side 816 and second side 818 may be, for example, textured or coated to provide a friction-stabilization surface and to allow for bone on-growth. The textured surface may be, for example, plasma sprayed biocompatible material, such as, commercially-pure titanium, or another biocompatible material as known by one of ordinary skill in the art.

With continued reference to FIGS. 84-91, the top surface 820 of the first member 810 includes at least one peg or vertical peg 524 extending away from the top surface 820. The at least one peg 524 may be as described in greater detail above with reference to implant 500 and will not be described again here for brevity sake.

Figure 85:
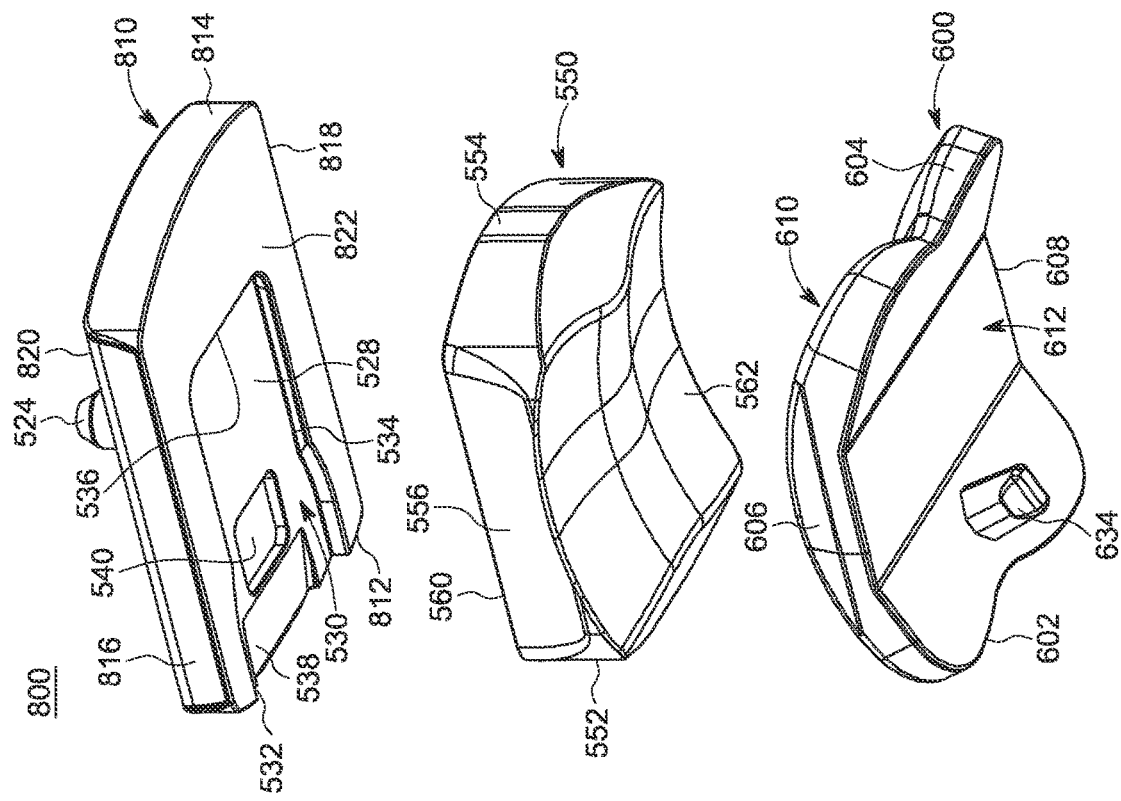
FIG. 85 is an exploded, second perspective view of the implant of FIG. 76, in accordance with an aspect of the present disclosure.
Figure 84:
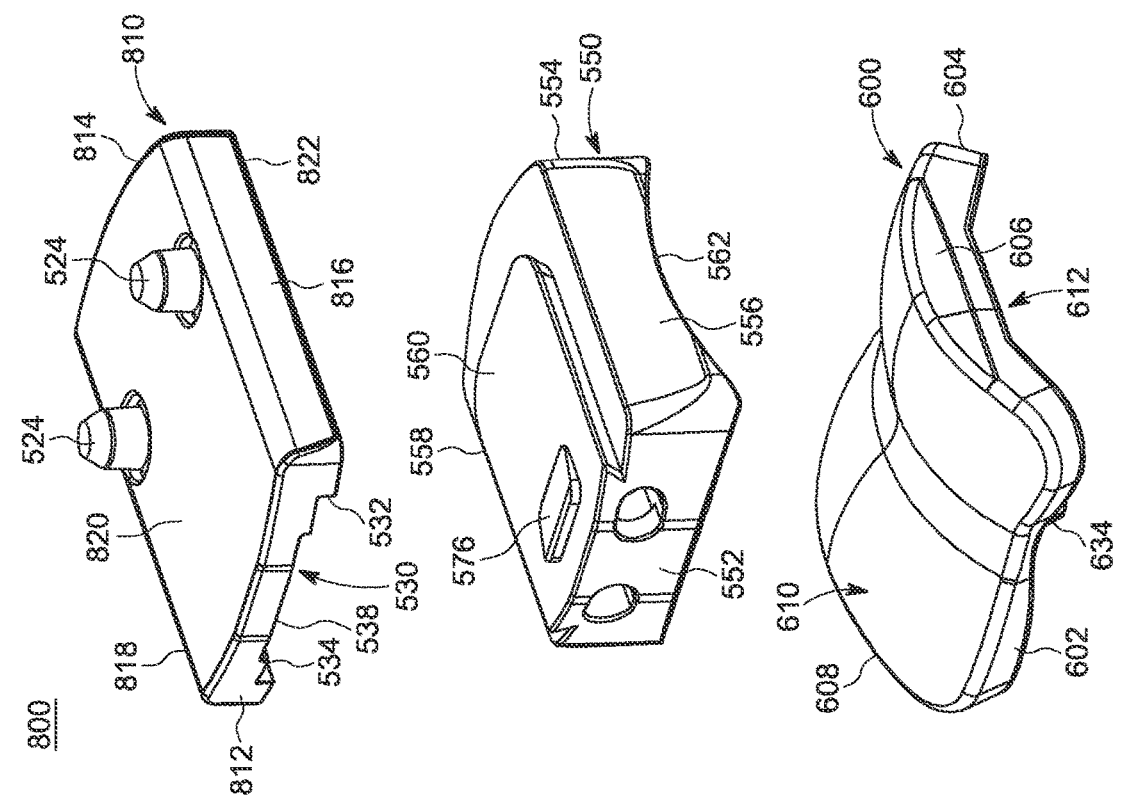
FIG. 84 is an exploded, first perspective view of the implant of FIG. 76, in accordance with an aspect of the present disclosure.

Referring now to FIGS. 85 and 91, the bottom surface 822 of the first member 810 is shown. The bottom surface 822 of the first member 810 may be the same or similar to the bottom surface 522 of first member 510. Specifically, the bottom surface 822 may include a recessed region or engagement region 528, an engagement channel 530, a first engagement feature or first female dovetail portion 532, a second engagement feature or second female dovetail portion 534, a third engagement feature or third female dovetail portion 536, a slot or removal engagement feature 538, a locking groove 540, each of which is described in greater detail above with reference to implant 500 and which will not be described again here for brevity sake.

Figure 80:
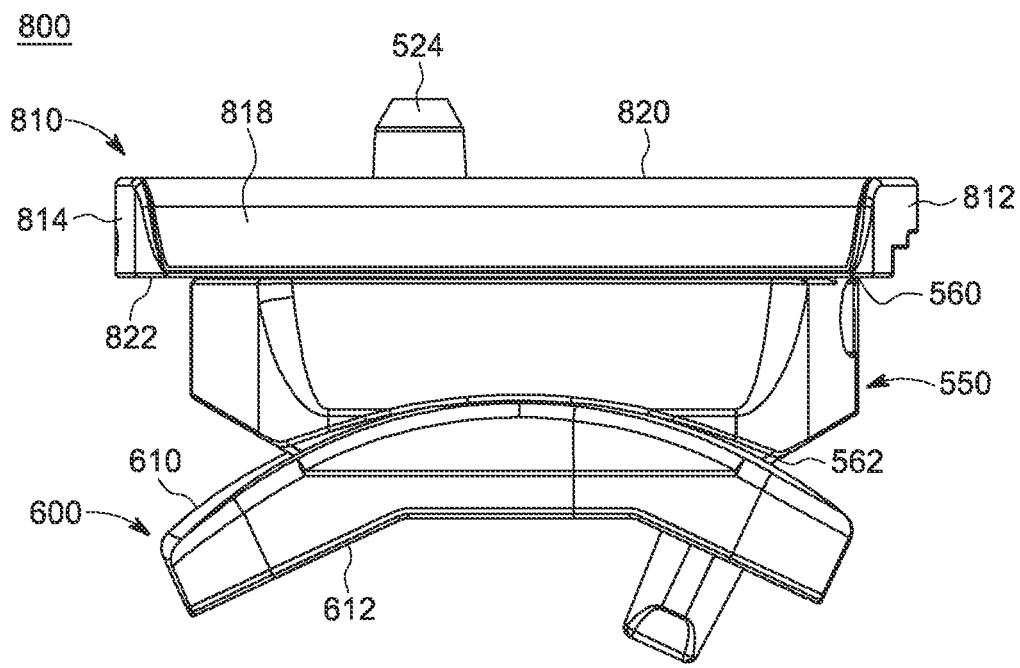
FIG. 80 is a first side view of the implant of FIG. 76, in accordance with an aspect of the present disclosure.
Figure 81:
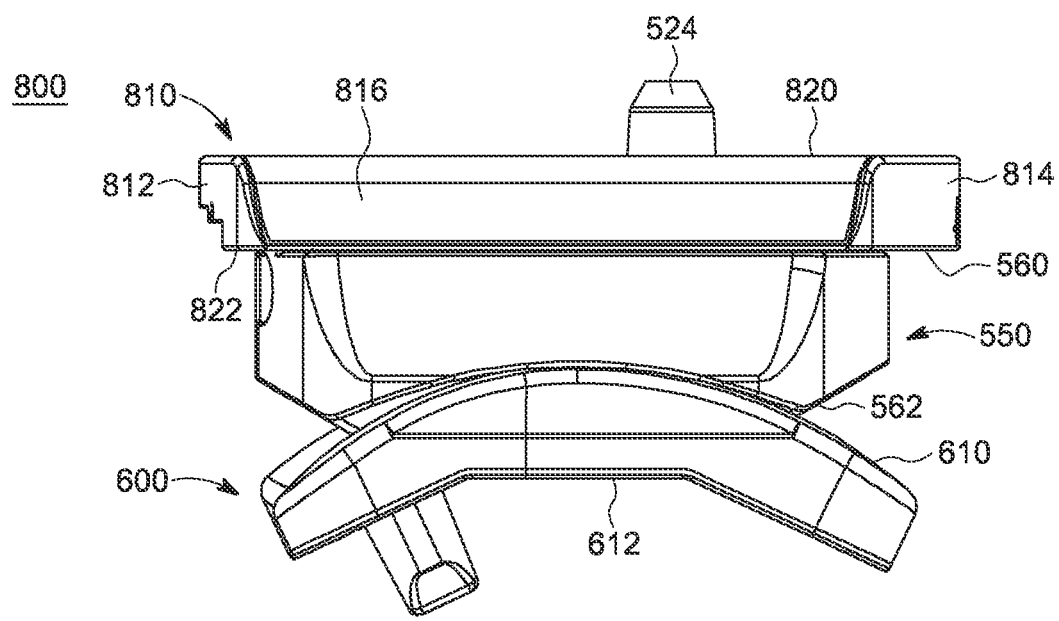
FIG. 81 is a second side view of the implant of FIG. 76, in accordance with an aspect of the present disclosure.
Figure 82:
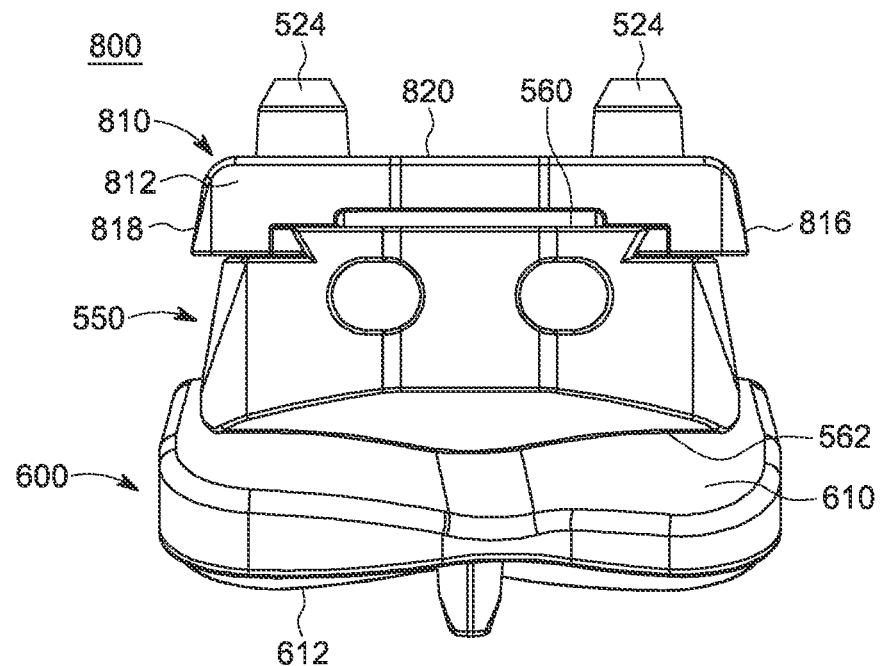
FIG. 82 is a first end view of the implant of FIG. 76, in accordance with an aspect of the present disclosure.
Figure 83:
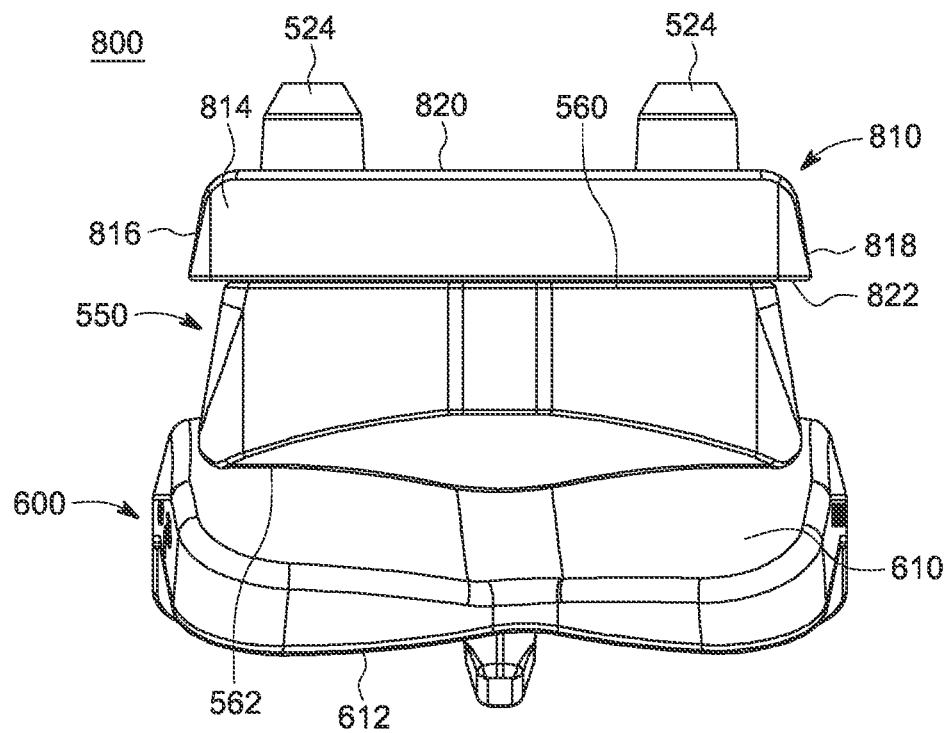
FIG. 83 is a second end view of the implant of FIG. 76, in accordance with an aspect of the present disclosure.

As shown in FIGS. 76-83, when assembled and/or implanted, the top surface 560 of the insert 550 couples to a bottom surface 822 of the first member 810. In addition, the top surface 610 of the second member 600 is configured or sized and shaped to articulate with the bottom surface 562 of the insert 550. Specifically, the medial articulating surface 618 of the second member 600 is configured to articulate with the first contact surface 578 of the insert 550, the lateral articulating surface 620 of the second member 600 is configured to articulate with the second contact surface 580 of the insert 550, and the central portion 622 of the second member 600 is configured to articulate with the third contact surface 582 of the insert 550. As shown in FIGS. 80 and 81, the first member 810 and coupled insert 550 are positioned on the second member 600 such that the first member 810 and insert 550 are in a neutral position.

Referring now to FIGS. 92-97, shows an implant kit 850. The implant kit 850 may include at least one first member 810, at least one first member 510, at least one insert 860, at least one second member 600, and at least one second member 910. Additional inserts 150, 350, 550, 660, 710 may also be included in the implant kit 850. Further, additional first members and second members described herein may be included in the kit 850 in place of or in addition to first members 510, 810 and second members 600, 910.

Figures 94, 95:
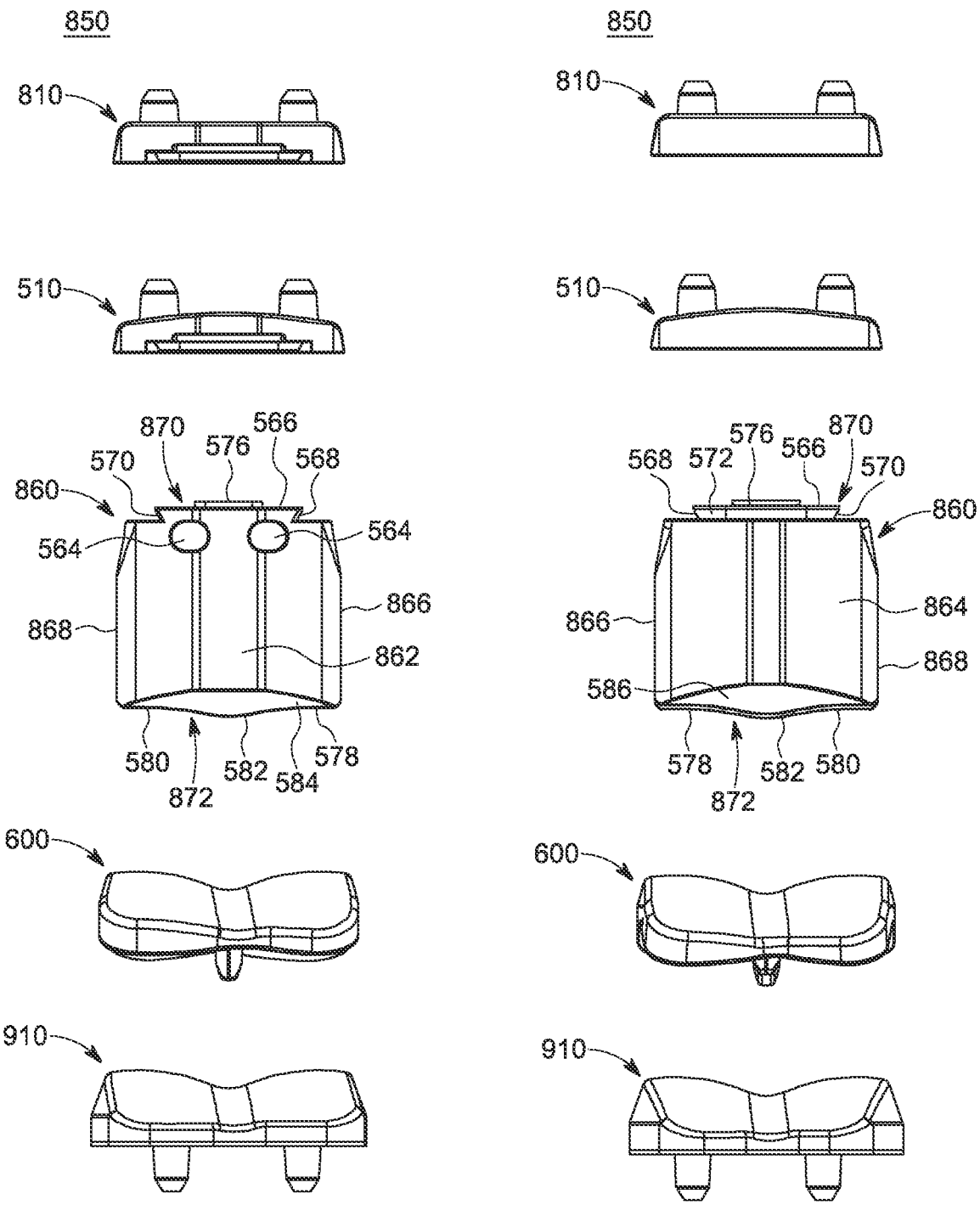
FIG. 94 is an exploded, first end view of the implant kit of FIG. 92, in accordance with an aspect of the present disclosure.
FIG. 95 is an exploded, second end view of the implant kit of FIG. 92, in accordance with an aspect of the present disclosure.
Figure 96:
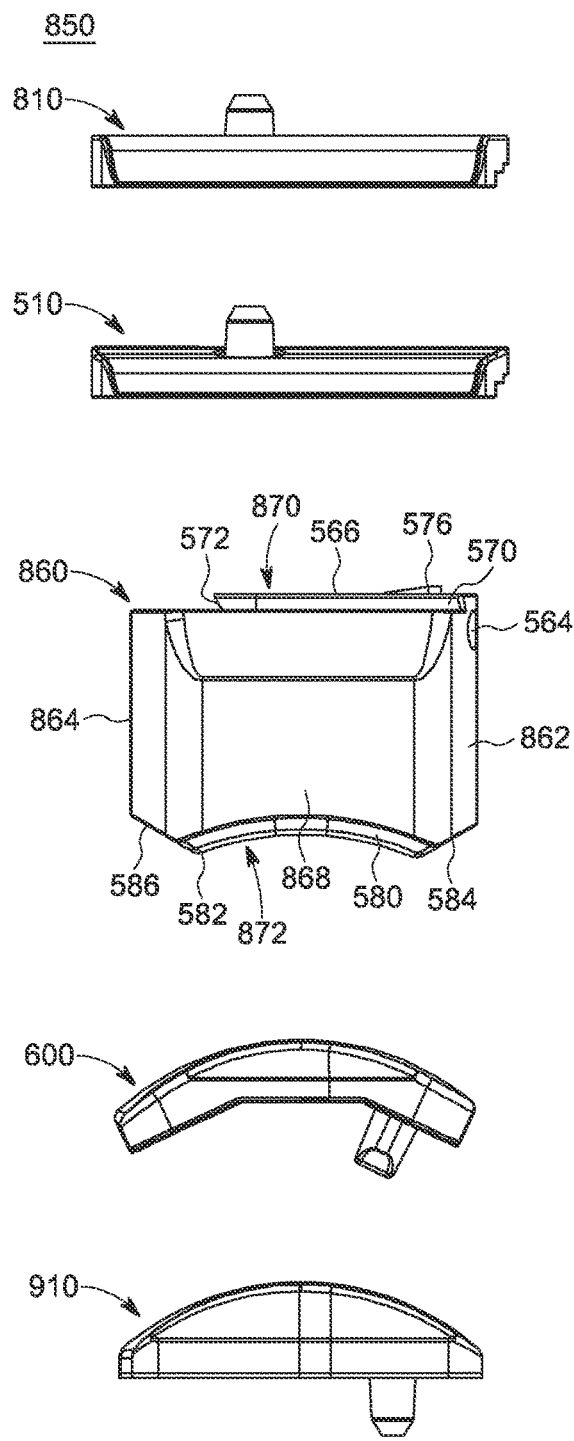
FIG. 96 is an exploded, first side view of the implant kit of FIG. 92, in accordance with an aspect of the present disclosure.
Figure 97:
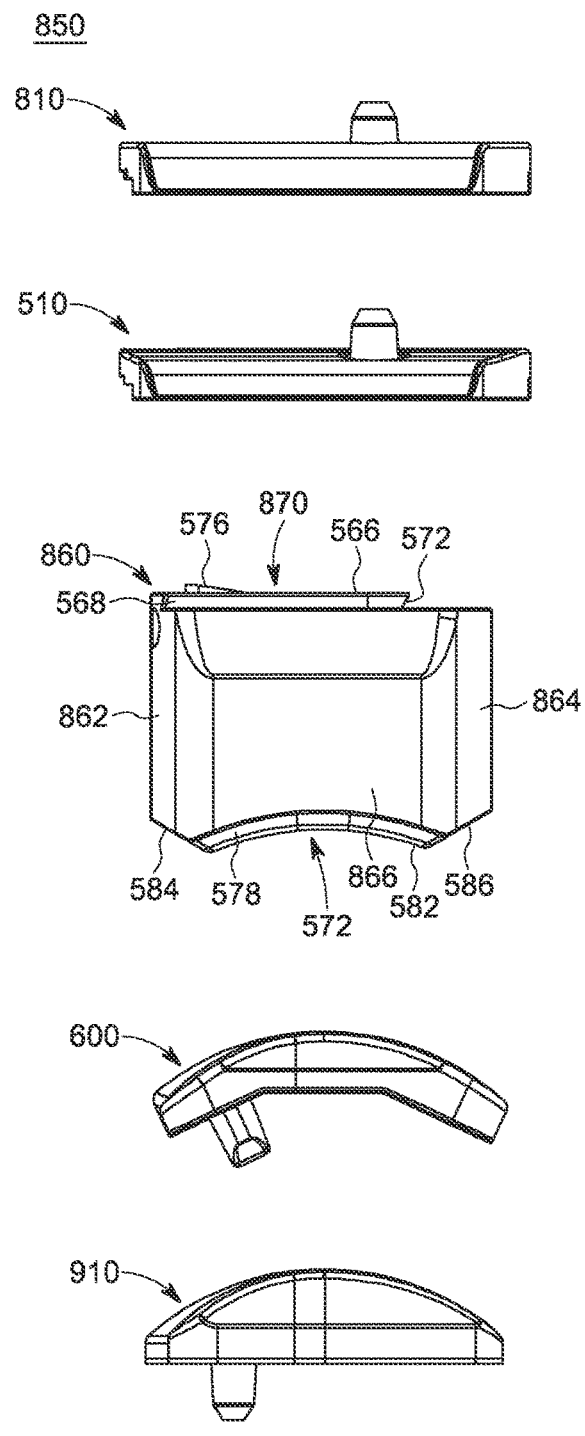
FIG. 97 is an exploded, second side view the implant kit of FIG. 92, in accordance with an aspect of the present disclosure.
Figure 98:
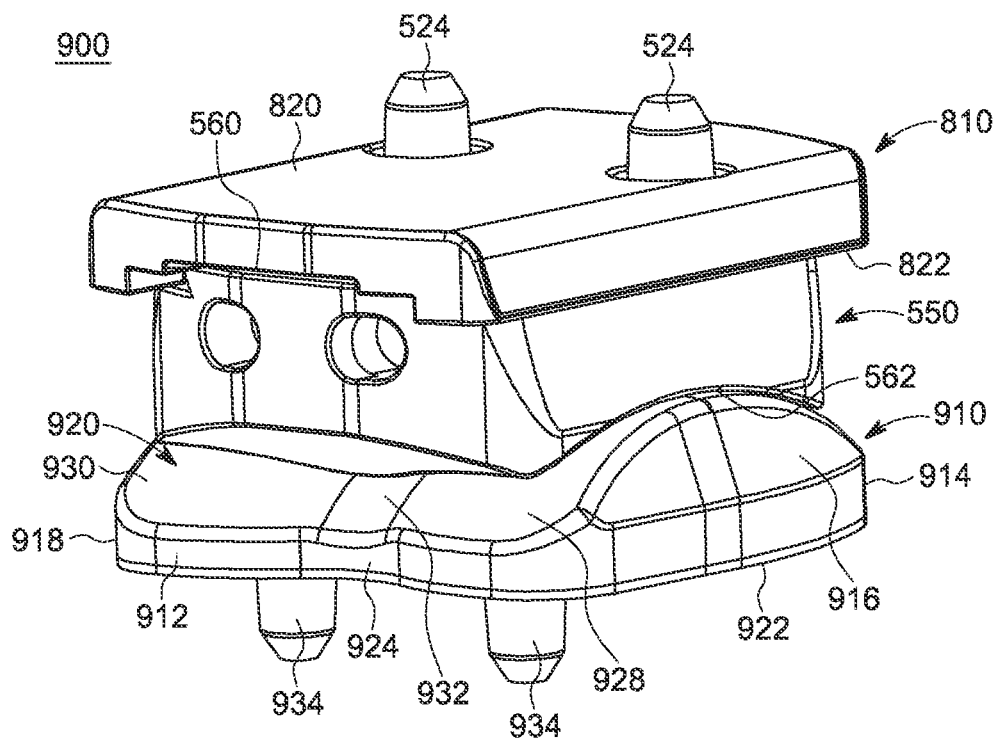
FIG. 98 is a first perspective view of an embodiment of an implant, in accordance with an aspect of the present disclosure.
Figure 99:
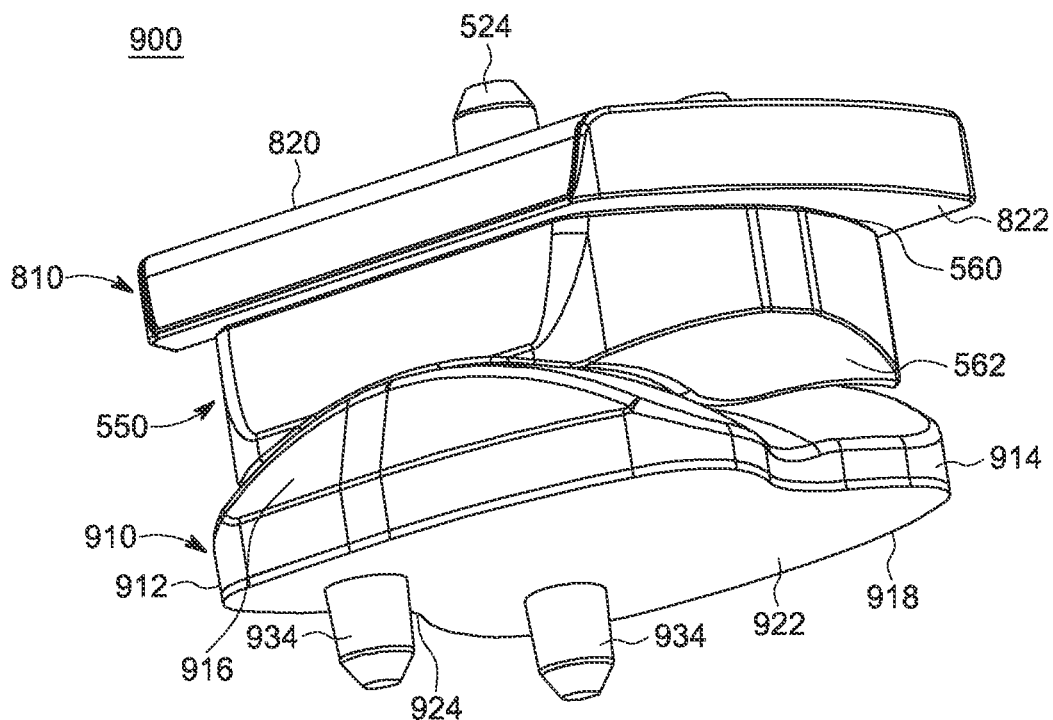
FIG. 99 is a second perspective view of the implant of FIG. 98, in accordance with an aspect of the present disclosure.

With continued reference to FIGS. 92-97, the insert, bearing insert, polyethylene insert, or articulating insert 860 may include a first end or anterior end 862 opposite a second end or posterior end 864. The insert 860 also includes a first side or medial side 866 opposite a second side or lateral side 868. In addition, the insert 860 includes a top surface 870 opposite a bottom surface 872. The first and second sides 866, 868 may be, for example, angled or tapered along at least a portion of the sides 866, 868 as the sides 866, 868 extend from the top surface 870 toward the bottom surface 872, as shown in FIGS. 94 and 95. The insert 860 may be, for example, a 20 mm insert.

The insert 860 may also include at least one opening 564 as described in greater detail above with respect to insert 550 which will not be described again here for brevity sake. The insert 860 may also include an engagement member or protrusion 566 with a first engagement feature or first male dovetail 568 near the first side 866, a second engagement feature or second male dovetail 570 near the second side 868, and a third engagement feature or third male dovetail 572 near the second end 864. The protrusion 566, first engagement feature 568, second engagement feature 570, and third engagement feature 572 are described in greater detail above with reference to insert 550 and will not be described again here for brevity sake. The top surface 870 may also include a locking tab or protrusion 576, which is also described in greater detail above with reference to insert 550 and which will not be described again here for brevity sake.

The bottom surface 872 of insert 860, as shown in FIGS. 93-97, may include the first contact surface or medial contact surface 578, the second contact surface or lateral contact surface 580, and the central contact surface 582, as described in greater detail above with reference to insert 550 and which will not be described again here for brevity sake. The bottom surface 872 may further include the first angled or tapered portion 584 and the second angled or tapered portion 586, as described in greater detail above with reference to insert 550 and which will not be described again here for brevity sake.

When assembled and/or implanted, the top surface 870 of the insert 860 couples to a bottom surface 522, 822 of a first member 510, 810. In addition, the top surface 610 of the second member 600, 910 is configured or sized and shaped to articulate with the bottom surface 872 of the insert 860. Specifically, the medial articulating surface 618, 928 of the second member 600, 910 is configured to articulate with the first contact surface 578 of the insert 810, the lateral articulating surface 620, 930 of the second member 600, 910 is configured to articulate with the second contact surface 580 of the insert 860, and the central portion 622, 932 of the second member 600, 910 is configured to articulate with the third contact surface 582 of the insert 860.

Referring now to FIGS. 98-113, another implant 900 is shown. The implant 900 includes a first member or tibia base 810, an insert 550, and a second member, talus component, or articulating member 910. The first member 810 and insert 550 are as described in greater detail above and will not be described again here for brevity sake. The top surface 560 of the insert couples to the first member 810 and the bottom surface 562 engages the second member 910.

Figure 102:
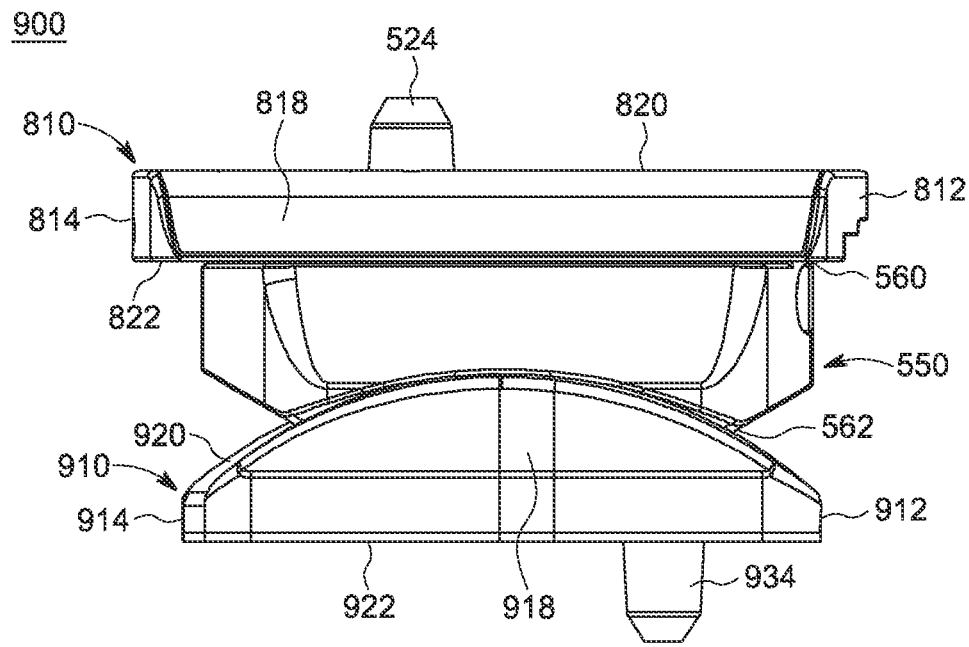
FIG. 102 is a first side view of the implant of FIG. 98, in accordance with an aspect of the present disclosure.
Figure 103:
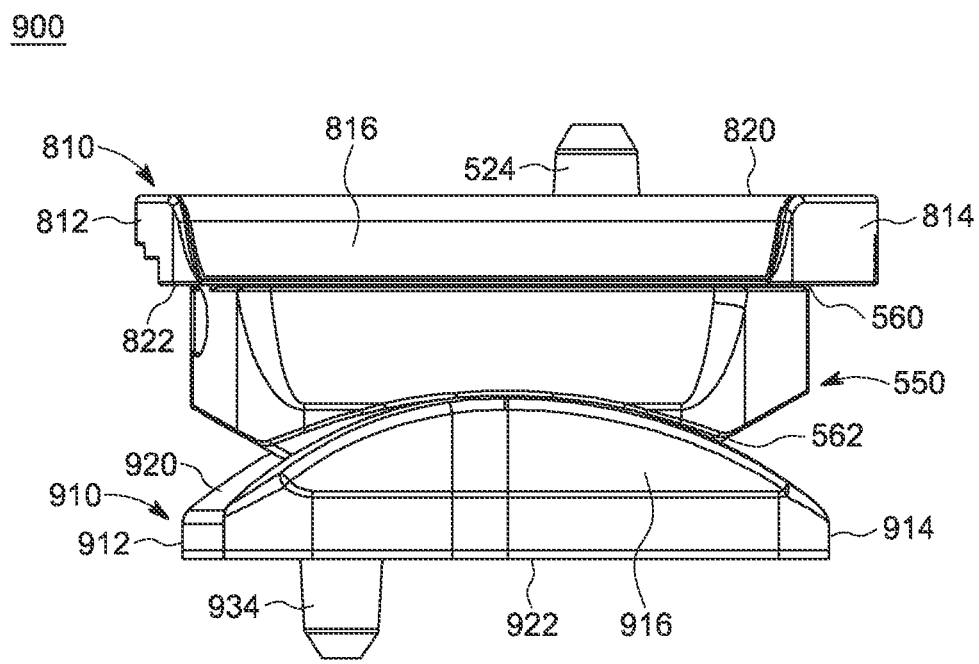
FIG. 103 is a second side view of the implant of FIG. 98, in accordance with an aspect of the present disclosure.
Figure 104:
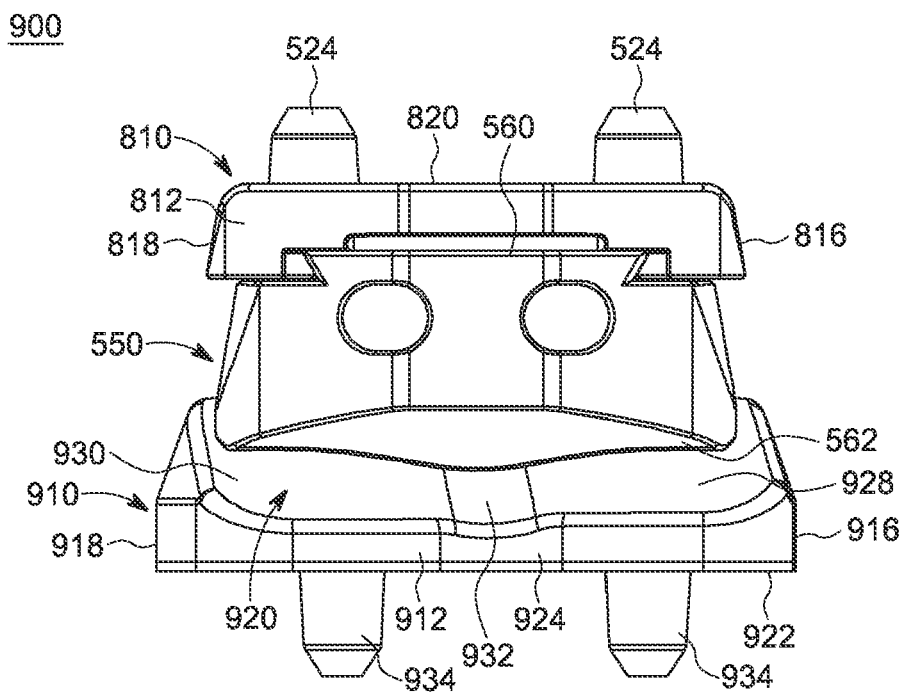
FIG. 104 is a first end view of the implant of FIG. 98, in accordance with an aspect of the present disclosure.
Figure 105:
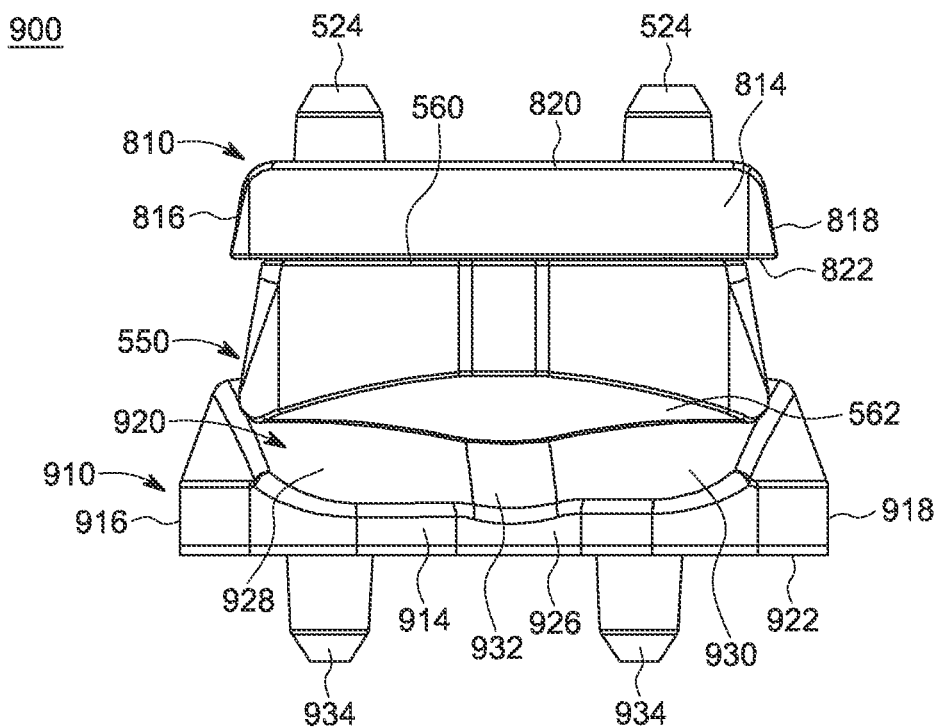
FIG. 105 is a second end view of the implant of FIG. 98, in accordance with an aspect of the present disclosure.

As shown in FIGS. 106-113, the second member, talus component or articulating member 910 has a first end or anterior end 912 opposite a second end or posterior end 914. The second member 910 also has a first side or medial side 916 opposite a second side or lateral side 918. In addition, the second member 910 has a top surface or articulating surface 920 opposite a bottom surface or bone engagement surface 922. The second member 910 may have, for example, a trapezium shape, as shown in FIGS. 100, 101, 112 and 113. The first side 916 and second side 918 may be angled as they extend from the top surface 920 to the bottom surface 922 and the angle may be, for example, approximately 15° to 20° and more preferably approximately 10°. The first side 916 may be, for example, shorter than the second side 918. As shown in FIGS. 102, 103, and 105, at least a portion of the first and second sides 916, 918 may be, for example, angled or tapered from the top surface 920 toward the bottom surface 922. The second member 910 includes an anterior recess 924 extending into the first end 912. The anterior recess 924 may be, for example, positioned near a midpoint of a lateral axis of the second member 910 or, alternatively may be medially biased. The second member 910 also includes a posterior recess 926 extending into the second end 914. The posterior recess 926 may be, for example, positioned near a midpoint of the lateral axis of the second member 910 or, alternatively, may be medially biased.

As shown in FIGS. 106 and 108-112, the top surface 920 of the second member 910 includes a medial articulating surface 928 extending from the first side 916 of the second member 910 toward the second side 918. The top surface 920 may also include a lateral articulating surface 930 extending from the second side 918 of the second member 910 toward the first side 916. In addition, the top surface 920 also includes a central articulating portion 932 positioned at a point where the medial articulating surface 928 contacts the lateral articulating surface 930.

The medial articulating surface 928 may include at least one first curvature along a longitudinal axis and at least one second curvature perpendicular to the longitudinal axis, as shown in FIG. 111. The lateral articulating surface 930 has at least one third curvature along the longitudinal axis and at least one fourth curvature perpendicular to the longitudinal axis. In addition, the central articulating portion 932 may have a concave curvature on the top surface 920 of the second member 910 and the medial and lateral articulating surfaces 928, 930 may have convex curvatures on the top surface 920 of the second member 910. The articulating surface 920 of the second member 910 may include, for example, at least one coronal radii and the at least one coronal radii may have, for example, a range of approximately 12 mm to 26 mm for a size 1 second member 910, a range of approximately 14 mm to 30 mm for a size 3 second member 910, and a range of approximately 17 mm to 34 mm for a size 5 second member 910. The articulating surface 920 of the second member 910 may include, for example, at least one sagittal radii and the at least one sagittal radii may have, for example, a range of approximately 18 mm to 25 mm for a size 1 second member 910, a range of approximately 20 mm to 28 mm for a size 3 second member 910, and a range of approximately 21 mm to 30 mm for a size 5 second member 910. In an embodiment, the anterior portion of the second member 910 may include a first sagittal radius of the lateral articulating surface 930 and a second sagittal radius of the medial articulating surface 928. The first sagittal radius may be, for example, larger than the second sagittal radius. In addition, the posterior portion of the second member 910 may include a third sagittal radius of the lateral articulating surface 930 and a fourth sagittal radius of the medial articulating surface 928. The third sagittal radius may be, for example, smaller than the fourth sagittal radius. A larger anterior lateral sagittal radius than anterior medial sagittal radius and a smaller posterior lateral sagittal radius than posterior medial sagittal radius allow for the joint axis of rotation to point distally and laterally during dorsiflexion and distally and medially during plantarflexion.

Figure 107:
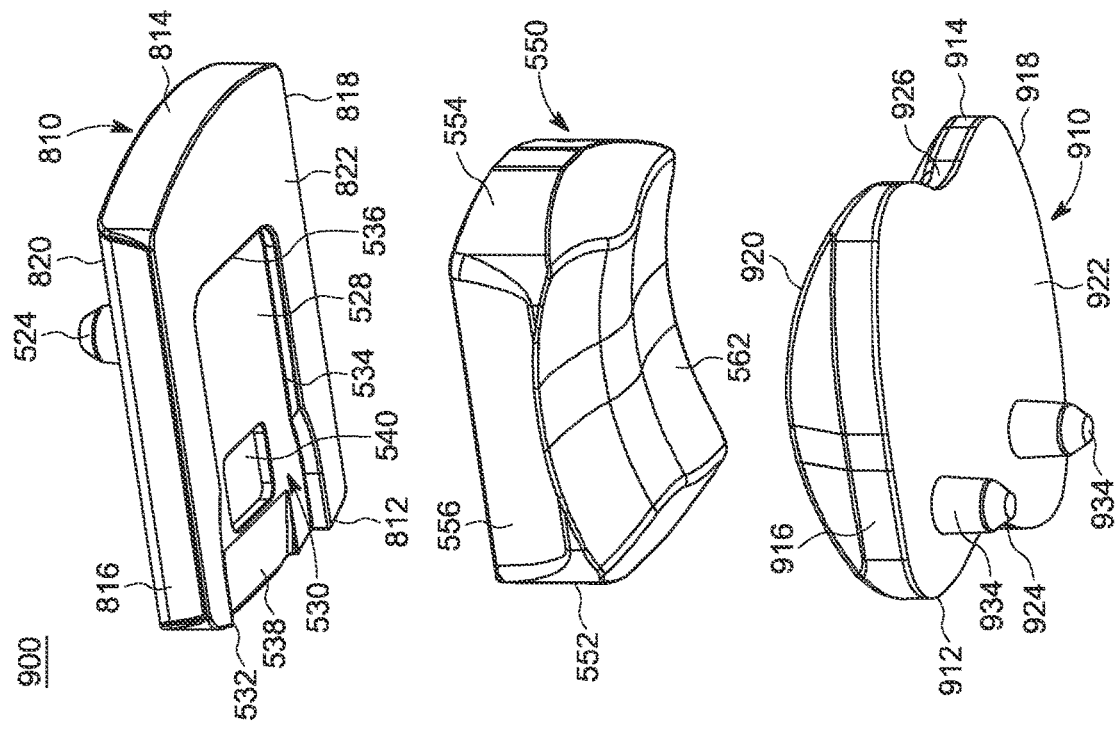
FIG. 107 is an exploded, second perspective view of the implant of FIG. 98, in accordance with an aspect of the present disclosure.
Figure 106:
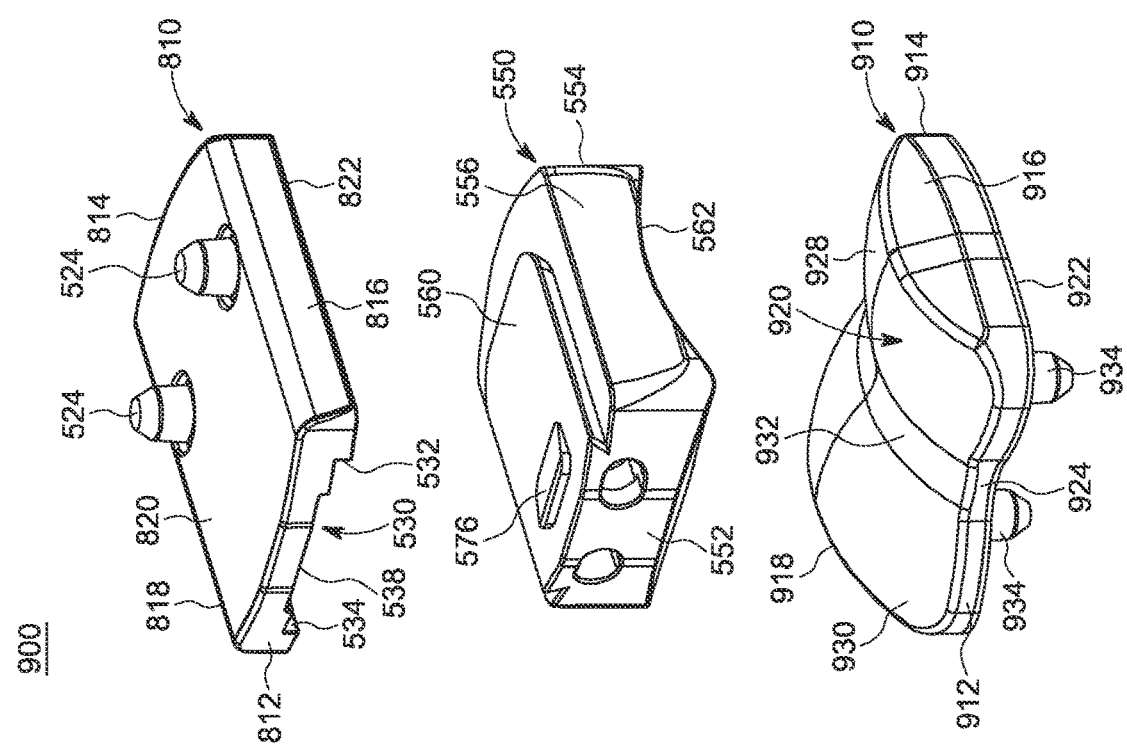
FIG. 106 is an exploded, first perspective view of the implant of FIG. 98, in accordance with an aspect of the present disclosure.

Referring now to FIGS. 99, 101-105, 107-111, and 113, the bottom surface 922 of the second member 910 may be a flat or planar surface. The bottom surface 922 of the second member 910 may be, for example, coated or textured with a biocompatible material. The texture or coating may be, for example, a plasma sprayed material, such as, a commercially-pure titanium or other biocompatible material, as known by one of ordinary skill in the art. The bottom surface 922 of the second member 910 may also include at least one stem or peg 934 extending away from the bottom surface 922, as shown in FIGS. 98, 99, 101-111 and 113. The at least one stem 934 may be, for example, two stems 934, although other numbers of stems 934 are also contemplated. As depicted, the first stem 934 is positioned between the anterior recess 924 and the first side 916 and the second stem 934 is positioned between the anterior recess 924 and the second side 918, as shown in FIGS. 107 and 113. The stems 934 may be, for example, positioned slightly medially biased and may be offset, for example, approximately 1 mm from a midpoint of the second member 910. The at least one stem 934 may not be, for example, textured or coated, rather the at least one stem 934 may be smooth to decrease bone resorption at the resection level. The at least one stem 934 may have, for example, a cylindrical, pyramidal, or other quadrilateral prism shape.

Figure 114:
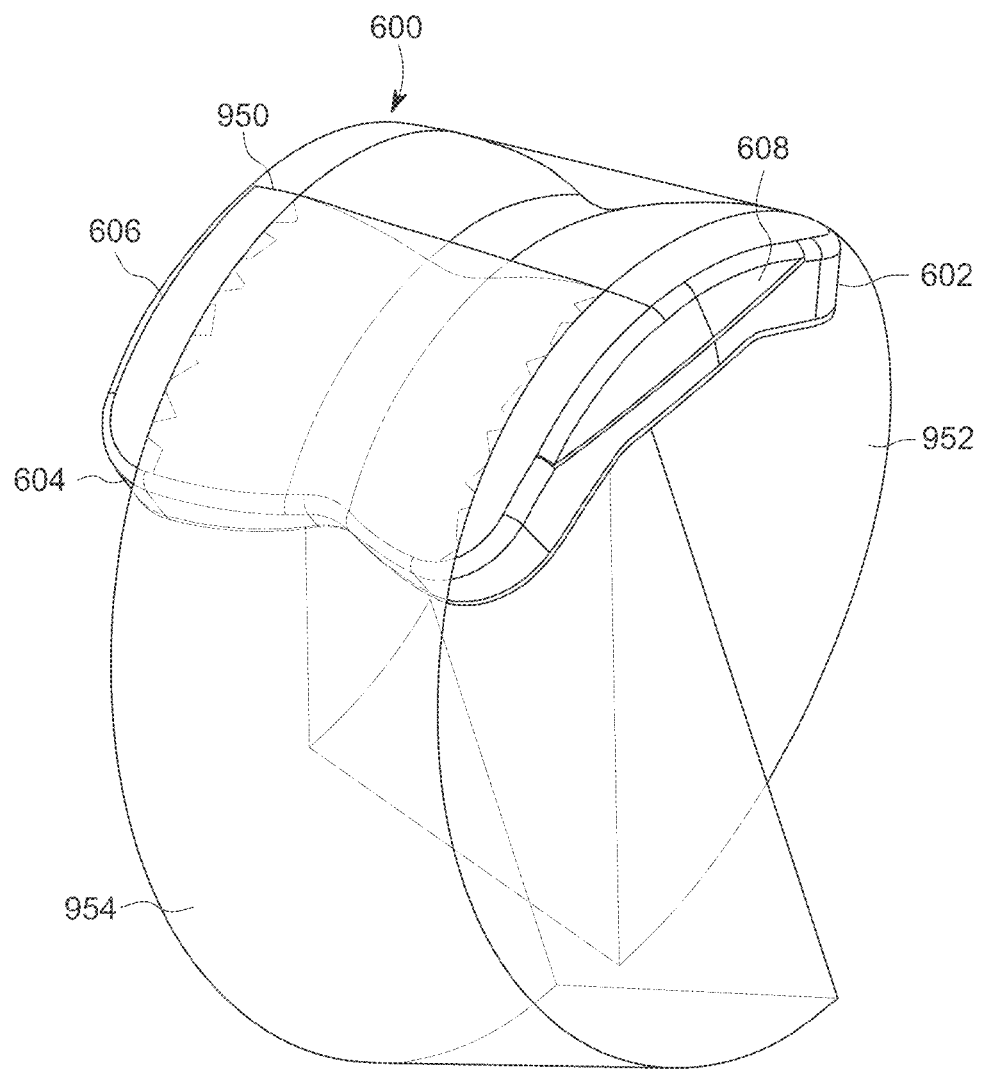
FIG. 114 is a perspective view a second member of an implant showing the articulation paths, in accordance with an aspect of the present disclosure.
Figure 115:
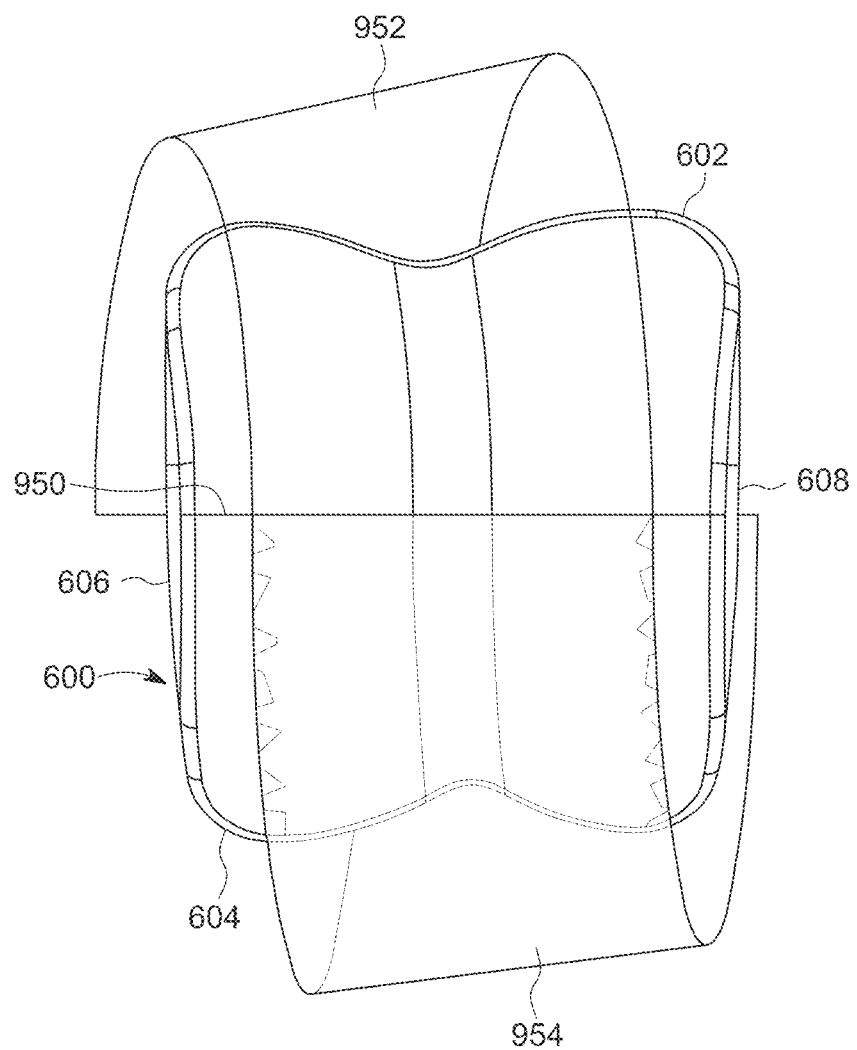
FIG. 115 is a top view of the second member of FIG. 114, in accordance with an aspect of the present disclosure.
Figure 116:
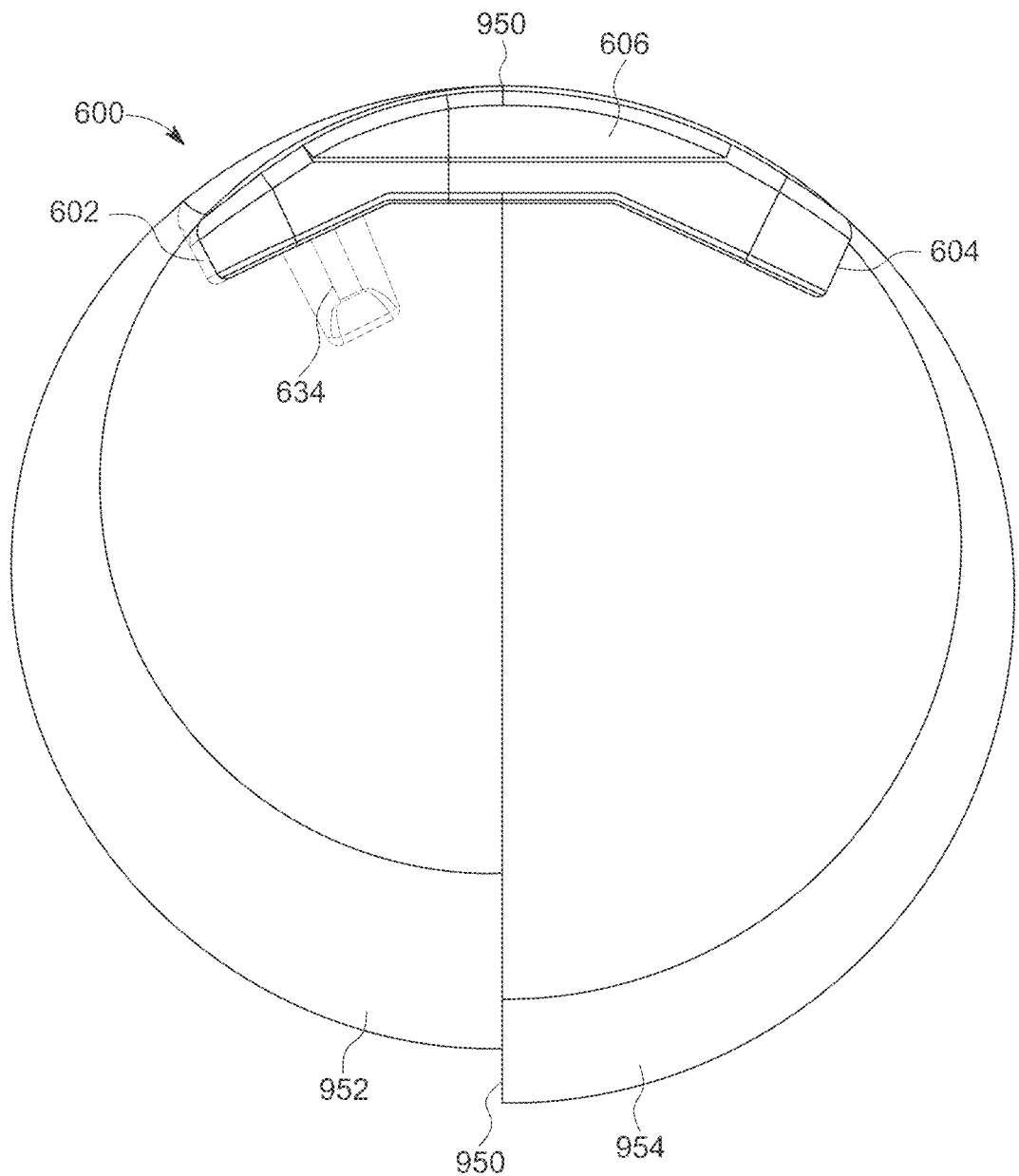
FIG. 116 is a side view of the second member of FIG. 114, in accordance with an aspect of the present disclosure.
Figure 117:
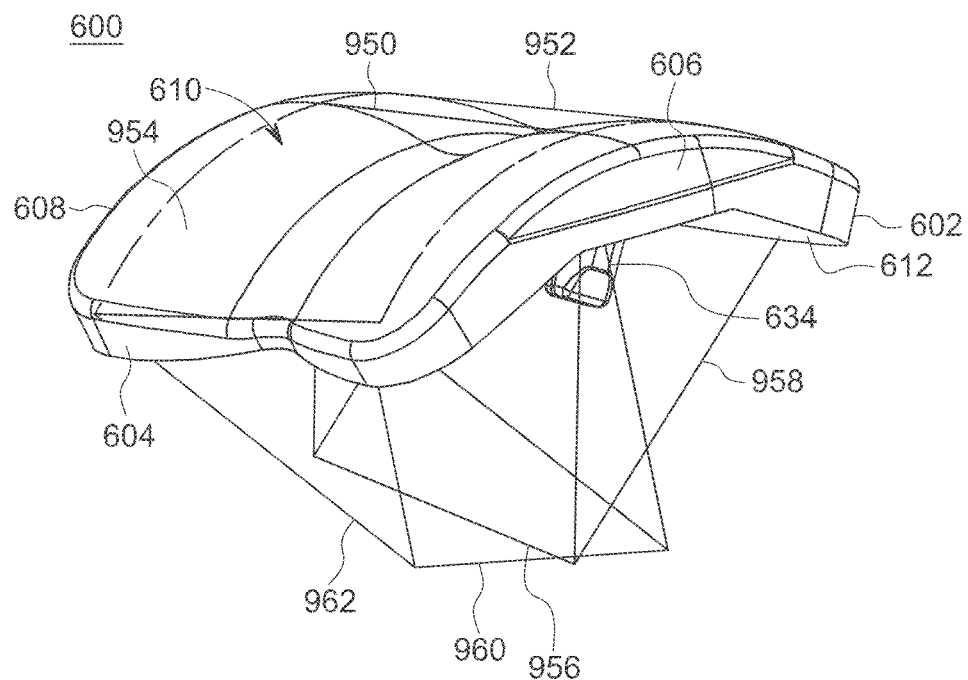
FIG. 117 is a first perspective view of the second member of FIG. 114 showing the axes of the articulation paths, in accordance with an aspect of the present disclosure.
Figure 118:
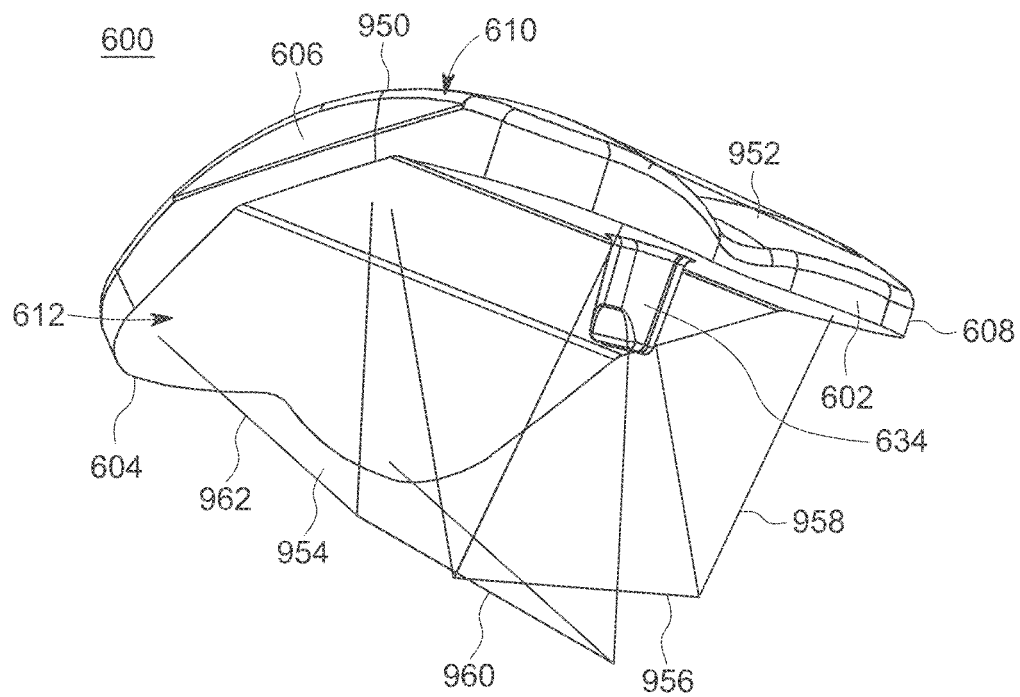
FIG. 118 is a second perspective view of the second member of FIG. 117, in accordance with an aspect of the present disclosure.
Figure 119:
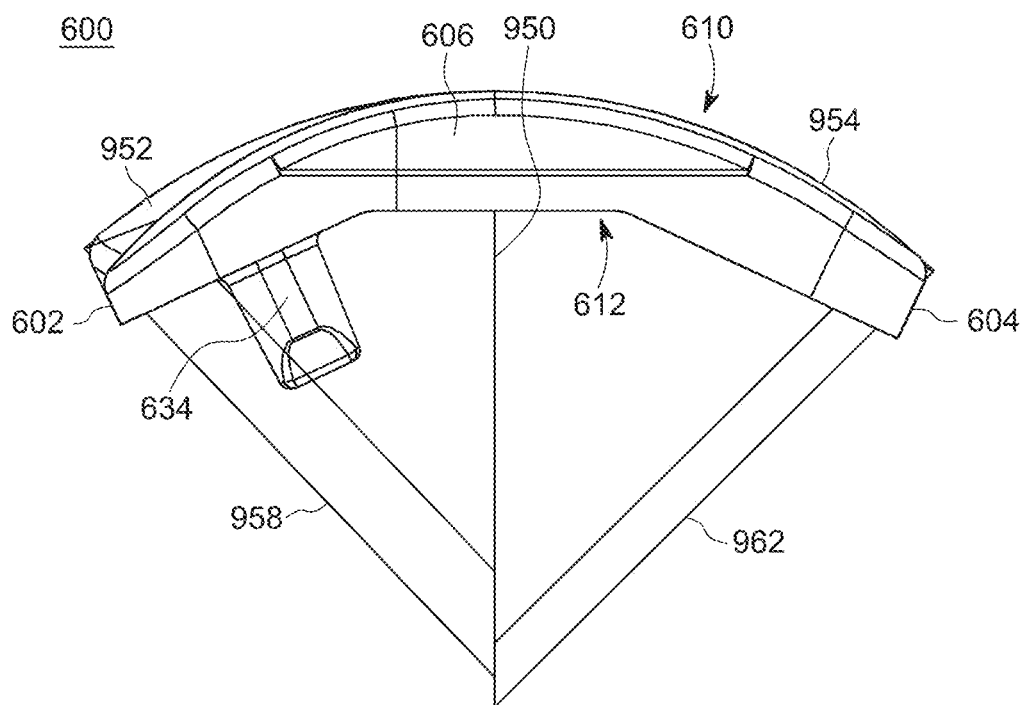
Figure 120:
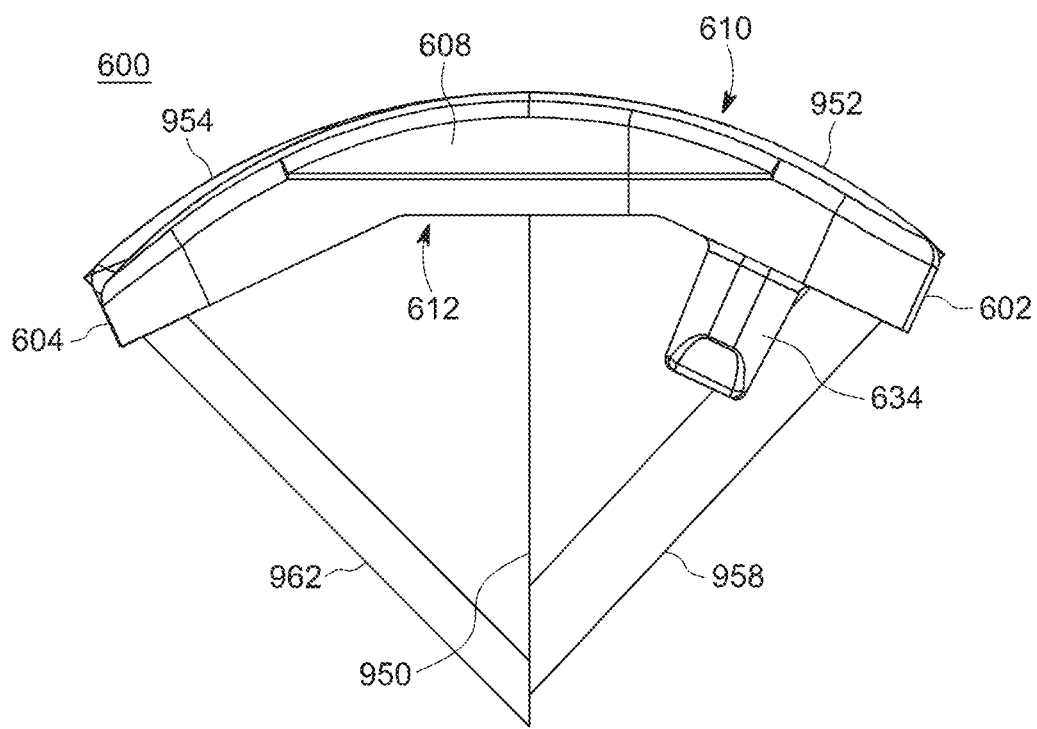
Figure 121:
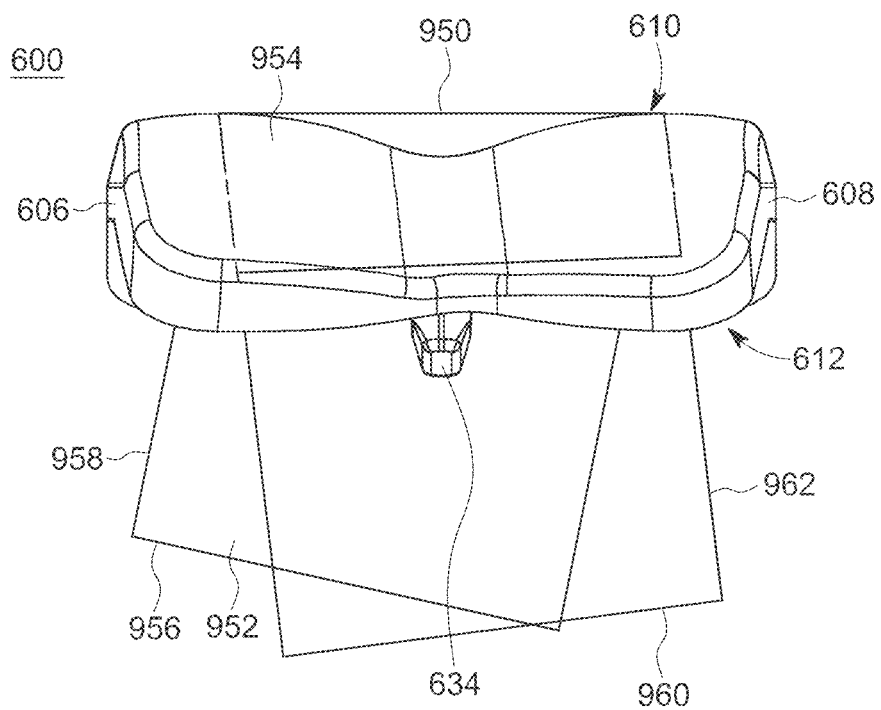
Figure 122:
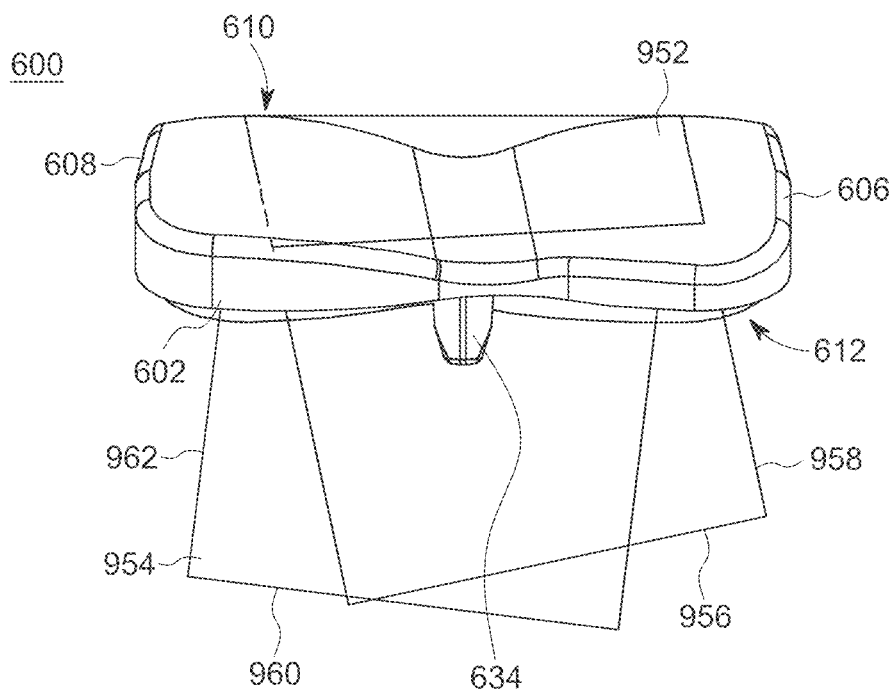

Referring now to FIGS. 114-122, the articulation paths of the second member, talus component, or articulating member 600 are shown. Although not show, the same or similar articulation paths may also be found on the second member 910. Referring now to FIGS. 114-116, a midpoint 950 extending between the first side 606 and the second side 608 separates the anterior articulation 952 and the posterior articulation 954. As shown in FIG. 115, the anterior articulation 952 curves in a medial direction and the posterior articulation 954 curves in a lateral direction. Referring now to FIG. 116, the anterior articulation 952 may have a first diameter and the posterior articulation 954 may have a second diameter. The first diameter may be smaller than the second diameter.

Referring now to FIGS. 117-122, the anterior articulation 952 extends around a first axis 956 forming a first radius 958 and the posterior articulation 954 extends around a second axis 960 forming a second radius 962. The first axis 956 may intersect the second axis 960. In addition, the first radius 958 may be, for example, smaller than the second radius 962.

The method shown in FIG. 17 may also be used to insert the implants 500, 650, 700, 800, 850, 900. Specifically, the method may include, for example, obtaining an implant 250 and making an incision to expose a joint with a first bone and a second bone 252. The implant may be, for example, an implant 500, 650, 700, 800, 850, 900 as described in greater detail above with reference to FIGS. 36-122 and which will not be described again here for brevity sake. The method may also include preparing the bones for receiving the implant 254. Next, the method may include coupling the first member to the first bone 256 and coupling the second member to the second bone 258. Then, the method may include inserting a second end of the insert into a first end of the first member 260. In addition, the method may include engaging a locking tab of the insert with a locking groove of the first member 262. In an embodiment, if the insert needs to be removed or replaced, for example, for a different size or due to wear, an instrument may be inserted into the slot of the insert to release the locking tab of the insert from the locking groove of the first member 264. Finally, the method may include closing the incision 266.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. For example, the components and features of FIGS. 1-17, FIGS. 18-35, FIGS. 36-51, FIGS. 52-63, FIGS. 64-75, FIGS. 76-91, FIGS. 92-97, and FIGS. 98-113 may be used interchangeably and in alternative combinations as would be modified or altered by one of skill in the art. Specifically, the first members 110, 310, 510, 810, the second members 200, 400, 600, 910 and the inserts 150, 350, 550, 660, 710, 860 may be used in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. An implant, comprising:
 a first member, wherein the first member comprises:
  a first end opposite a second end;
  a first side opposite a second side; and
  a top surface opposite a bottom surface, wherein the top surface comprises:
   at least one peg extending away from the top surface;
   at least one protrusion extending away from the top surface; and
   multiple arc radii as the top surface extends between the first side and the second side of the first member;
 a second member, wherein the second member comprises:
  a first end opposite a second end;
  a first side opposite a second side; and
  a top surface opposite a bottom surface, the top surface comprising:
   a medial articulating surface extending from the first side of the second member toward the second side of the second member and comprising:
    an anterior-medial sagittal radius; and a posterior-medial sagittal radius;
a lateral articulating surface extending from the second side of the second member toward the first side of the second member and comprising:
an anterior-lateral sagittal radius; and
a posterior-lateral sagittal radius; and
wherein the anterior-lateral sagittal radius is larger than the anterior-medial sagittal radius, and wherein the posterior-medial sagittal radius is larger than the posterior-lateral sagittal radius; and
an insert with a top surface and a bottom surface, wherein the top surface couples to the first member and the bottom surface engages the second member.

2. The implant of claim 1, wherein the first member comprises:
a tibia base.

3. The implant of claim 1, wherein the at the least one peg and the at least one protrusion are the same and the at least one peg is positioned near the first side of the first member and the at least one protrusion is positioned near the second side of the first member.

4. The implant of claim 1, wherein the at least one protrusion is spaced from the at least one peg.

5. The implant of claim 4, wherein the at least one protrusion is four protrusions positioned equally spaced around the at least one peg.

6. The implant of claim 4, wherein the at least one protrusion is two protrusions positioned spaced apart from each other.

7. The implant of claim 1, wherein the multiple arc radii comprise:
a first arc radius positioned near a central portion of the first member;
second arc radii, wherein one second arc radius is positioned adjacent to the first arc radius toward the first side of the first member and another second arc radius is positioned adjacent to the first arc radius toward the second side of the first member; and
third arc radii, wherein one third arc radius is positioned between one second arc radius and the first side and another third arc radius is positioned between the other second arc radius and the second side.

8. The implant of claim 1, wherein the bottom surface of the first member comprises:
a recessed region extending into the first member from the bottom surface toward the top surface; and
an engagement channel extending from the first end into the recessed region;
a first engagement feature extending from the first side into the recessed region;
a second engagement feature extending from the second side into the recessed region; and
a third engagement feature extending from a position near the second end into the recessed region.

9. The implant of claim 8, wherein the engagement features comprise:
female dovetail portions.

10. The implant of claim 8, wherein the bottom surface of the first member further comprises:
a slot; and
a locking groove positioned adjacent to the slot;
wherein the slot is angled as the slot extends from the first end toward the locking groove.

11. The implant of claim 10, wherein the second member comprises:
a talus component.

12. The implant of claim 10, wherein the second member comprises:
an anterior recess extending into the first end; and
a posterior recess extending into the second end.

13. The implant of claim 12, wherein the top surface of the second member comprises:
a central articulating portion positioned at a location between the medial articulating surface and the lateral articulating surface.

14. The implant of claim 13, wherein the medial articulating surface has at least one first curvature along a first longitudinal axis and at least one second curvature perpendicular to the first longitudinal axis.

15. The implant of claim 14, wherein the lateral articulating surface has at least one third curvature along a second longitudinal axis and at least one fourth curvature perpendicular to the second longitudinal axis.

16. The implant of claim 15, wherein the central articulating portion has a concave curvature on the top surface of the second member and the medial and lateral articulating surfaces have a convex curvature on the top surface of the second member.

17. The implant of claim 15, wherein the first longitudinal axis is parallel to the second longitudinal axis.

18. The implant of claim 13, wherein the bottom surface of the second member comprises:
a first portion extending from the first end to a first transition point;
a second portion extending from the first transition point to a second transition point;
a third portion extending from the second transition point to the second end;
at least one stem extending away from the first portion of the bottom surface; and
wherein the second portion is positioned between the first portion and the third portion.

19. The implant of claim 18, wherein the first portion, the second portion, and the third portion are substantially planar, and wherein the first portion extends away from the second portion at a first angle and the third portion extends away from the second portion at a second angle.

20. The implant of claim 19, wherein the at least one stem is a fin positioned adjacent to and spaced apart from the anterior recess.

21. The implant of claim 18, wherein the at least one stem is two stems and a first stem is positioned on the first portion between the anterior recess and the first side and a second stem is positioned on the first portion between the anterior recess and the second side.

22. The implant of claim 21, wherein the insert comprises:
a polymer insert comprising:
a first end opposite a second end;
a first side opposite a second side; and
a top surface opposite a bottom surface.

23. The implant of claim 22, wherein the first end of the insert comprises:
at least one opening extending into the insert from the first end toward the second end.

24. The implant of claim 23, wherein the top surface of the insert comprises:
an engagement member, the engagement member comprises:
a first engagement feature on a first side of the engagement member;
a second engagement feature on a second side of the engagement member; and a third engagement feature on a second end of the engagement member.

25. The implant of claim 24, wherein the first engagement feature is a first male dovetail, the second engagement feature is a second male dovetail, and the third engagement feature is a third male dovetail.

26. The implant of claim 25, wherein the top surface of the insert further comprises:
    a slot positioned near and open to the first end; and
    a locking tab positioned adjacent to the slot and extending away from the top surface of the insert, wherein the locking tab is configured to engage the locking groove of the bottom surface of the first member.

27. The implant of claim 26, wherein the bottom surface of the insert comprises:
    a first contact surface extending from the first side of the insert toward the second side;
    a second contact surface extending from the second side of the insert toward the first side; and
    a central contact surface positioned between the first contact surface and the second contact surface.

28. The implant of claim 27, wherein the first contact surface comprises at least one first curvature along a longitudinal axis and at least one second curvature along a lateral axis and the second contact surface comprises at least one third curvature along a longitudinal axis and at least one fourth curvature along a lateral axis.

29. The implant of claim 28, wherein the first contact surface includes at least one first concave curvature, the second contact surface includes at least one second concave curvature, and the central contact surface includes at least one convex curvature.

30. The implant of claim 1, wherein the second member comprises:
    an anterior articulation curved in a medial direction; and
    a posterior articulation curved in a lateral direction, wherein the anterior articulation engages the posterior articulation near a midpoint of the second member.

31. The implant of claim 30, wherein the anterior articulation has a first diameter and the posterior articulation has a second diameter, and wherein the first diameter is smaller than the second diameter.

32. The implant of claim 30, wherein the anterior articulation extends around a first axis forming a first radius and the posterior articulation extends around a second axis forming a second radius, wherein the first radius is smaller than the second radius.

33. An implant, comprising:
    a first member;
    a second member, wherein the second member comprises:
        an anterior articulation;
        a posterior articulation, wherein the anterior articulation engages the posterior articulation near a midpoint of the second member;
        a medial articulating surface extending from a first side toward a second side and comprising:
            an anterior-medial sagittal radius; and
            a posterior-medial sagittal radius; and
        a lateral articulating surface extending from the second side toward the first side and comprising:
            an anterior-lateral sagittal radius; and
            a posterior-lateral sagittal radius;
        wherein the anterior-lateral sagittal radius is larger than the anterior-medial sagittal radius, and wherein the posterior-medial sagittal radius is larger than the posterior-lateral sagittal radius; and
    an insert with a top surface and a bottom surface, wherein the top surface couples to the first member and the bottom surface engages the second member.

34. An implant, comprising:
    a first member, wherein the first member comprises:
        a first end opposite a second end;
        a first side opposite a second side; and
        a top surface opposite a bottom surface, wherein the bottom surface comprises:
            a recessed region extending into the first member from the bottom surface toward the top surface; and
            an engagement channel extending from the first end into the recessed region;
    a second member, wherein the second member comprises:
        a medial articulating surface extending from a first side of the second member toward a second side of the second member and comprising:
            an anterior-medial sagittal radius; and
            a posterior-medial sagittal radius; and
        a lateral articulating surface extending from the second side of the second member toward the first side of the second member and comprising:
            an anterior-lateral sagittal radius; and
            a posterior-lateral sagittal radius;
        wherein the anterior-lateral sagittal radius is larger than the anterior-medial sagittal radius, and wherein the posterior-medial sagittal radius is larger than the posterior-lateral sagittal radius; and
    an insert with a top surface and a bottom surface, wherein the top surface couples to the first member and the bottom surface engages the second member.

* * * * *